United States Patent
Inuki et al.

(10) Patent No.: US 10,919,926 B2
(45) Date of Patent: Feb. 16, 2021

(54) COMPOUND OR SALT THEREOF, NATURAL KILLER T CELL ACTIVATOR, AND PHARMACEUTICAL COMPOSITION

(71) Applicants: KEIO UNIVERSITY, Tokyo (JP); REGiMMUNE CORPORATION, Tokyo (JP)

(72) Inventors: Shinsuke Inuki, Yokohama (JP); Natsumi Hirata, Yokohama (JP); Emi Kashiwabara, Yokohama (JP); Junichiro Kishi, Yokohama (JP); Toshihiko Aiba, Yokohama (JP); Yukari Fujimoto, Yokohama (JP)

(73) Assignees: KEIO UNIVERSITY, Tokyo (JP); REGiMMUNE CORPORATION, Tokyo (JP)

( * ) Notice: Subject to any disclaimer, the term of this patent is extended or adjusted under 35 U.S.C. 154(b) by 165 days.

(21) Appl. No.: 16/087,545

(22) PCT Filed: Mar. 2, 2017

(86) PCT No.: PCT/JP2017/008381
§ 371 (c)(1),
(2) Date: Nov. 5, 2018

(87) PCT Pub. No.: WO2017/163808
PCT Pub. Date: Sep. 28, 2017

(65) Prior Publication Data
US 2020/0207798 A1 Jul. 2, 2020

(30) Foreign Application Priority Data
Mar. 22, 2016 (JP) .............................. JP2016-057416

(51) Int. Cl.
*C07H 15/04* (2006.01)
*C07H 15/18* (2006.01)
*C07H 15/26* (2006.01)

(52) U.S. Cl.
CPC ............ *C07H 15/04* (2013.01); *C07H 15/18* (2013.01); *C07H 15/26* (2013.01)

(58) Field of Classification Search
None
See application file for complete search history.

(56) References Cited

U.S. PATENT DOCUMENTS

| | | |
|---|---|---|
| 6,531,453 B1 | 3/2003 | Taniguchi et al. |
| 2013/0131311 A1 | 5/2013 | Garner |

FOREIGN PATENT DOCUMENTS

| | | |
|---|---|---|
| JP | H06-271598 A | 9/1994 |
| JP | H10-251287 A | 9/1998 |
| JP | 2004-131481 A | 4/2004 |
| WO | WO 2008/082156 A1 | 7/2008 |
| WO | WO 2011/052919 A2 | 5/2011 |
| WO | WO 2014/017928 A1 | 1/2014 |
| WO | WO 2014/088432 A1 | 6/2014 |

OTHER PUBLICATIONS

Sakai et al., Journal of Medicinal Chemistry, 1999, vol. 42, pp. 1836-1841 (Year: 1999).*
Database CA (Chemical Abstracts Service), Accession No. 1984:22917 (1984).
Database CA (Chemical Abstracts Service), Accession No. 2009:640700 (2009).
Faroux-Corlay et al., "Amphiphilic Anionic Analogues of Galactosylceramide: Synthesis, Anti-HIV-1 Activity, and gp120 Binding," *J. Med. Chem.*, 44(13): 2188-2203 (2001).
Inuki et al., "Isolated Polar Amino Acid Residues Modulate Lipid Binding in the Large Hydrophobic Cavity of CD1d," *ACS Chem. Biol.*, 11(11): 3132-3139 (2016).
Kamio et al., "Galactosylceramide containing ω-amino-fatty acids: preparation, characterization, and sulfotransferase acceptor," *J. Lipid Res.*, 33(8): 1227-1232 (1992).
Miermont et al., "Cowpea Mosaic Virus Capsid: A Promising Carrier for the Development of Carbohydrate Based Antitumor Vaccines," *Chem. Eur. J.*, 14(16): 4939-4947 (2008).
Molotkovsky et al., "Synthesis and characterization of new fluorescent glycolipid probes. Molecular organisation of glycosphingolipids in mixed-composition lipid bilayers," *Chemistry and Physics of Lipids*, 58(3): 199-212 (1991).
Anderson et al., "A self-adjuvanting vaccine induces cytotoxic T lymphocytes that suppress allergy," *Nat. Chem. Biol.*, 10(11): 943-949 (2014).

(Continued)

*Primary Examiner* — Traviss C McIntosh, III
(74) *Attorney, Agent, or Firm* — Leydig, Voit & Mayer, Ltd.

(57) ABSTRACT

Problems of the present invention is to provide a novel compound or a salt thereof capable of activating natural killer T cell, a natural killer T cell activating agent containing such a compound or a salt thereof, and a pharmaceutical composition.
The compound of the present invention is a compound represented by the following formula (1) or a salt thereof. It is preferable that total carbon number of the number of carbon atoms in the monovalent hydrocarbon group in $R^1$ in the formula (1) excluding a sustitutent and the number of carbon atoms in the divalent hydrocarbon group in $X^1$ is 5 to 50. The natural killer T cell activating agent contains the aforementioned compound or a salt thereof. The pharmaceutical composition contains the aforementioned compound or a pharmacologically acceptable salt thereof.

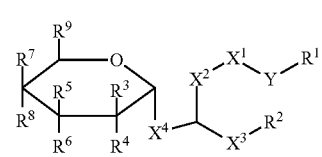

(1)

20 Claims, 10 Drawing Sheets

(56) References Cited

OTHER PUBLICATIONS

Baek et al., "Rational Design and Evaluation of a Branched-Chain-Coating Glycolipid Antigen That Binds to CD1d," *Chem. Asian J.*, 5(7): 1560-1564 (2010).

Cui et al., "4,5-Cis Unsaturated α-GalCer Analogues Distinctly Lead to CD1d-Mediated Th1-Biased NKT Cell Responses," *Chem. Res. Toxicol.*, 28(6): 1209-1215 (2015).

Deng et al., "Impact of Sugar Stereochemistry on Natural Killer T Cell Stimulation by Bacterial Glycolipids," *Org. Biomol. Chem.*, 9(22): 7659-7662 (2011).

Lee et al., "An α-GalCer analogue with branched acyl chain enhances protective immune responses in a nasal influenza vaccine," *Vaccine*, 29(3): 417-425 (2011).

Li et al., "Rapid Identification of Immunostimulatory α-Galactosylceramides Using Synthetic Combinatorial Libraries," *J. Comb. Chem.*, 9(6): 1084-1093 (2007).

Lim et al., "Design and Evaluation of ω-Hydroxy Fatty Acids Containing α-GalCer Analogues for CD1d-Mediated NKT Cell Activation," *ACS Med. Chem. Lett.*, 5(4): 331-335 (2014).

Sakai et al., "Syntheses of Biotinylated α-Galactosylceramides and Their Effects on the Immune System and CD1 Molecules," *J. Med. Chem.*, 42(10): 1836-1841 (1999).

Sakai et al., "Synthesis of NBD-α-galactosylceramide and Its Immunologic Properties," *Org. Lett.*, 1(3): 359-361 (1999).

Stocker et al., "Trehalose diesters, lipoteichoic acids and α-GalCer: using chemistry to understand immunology," *Carbohydr. Res.*, 389: 3-11 (2014).

Vo-Hoang et al., "Total Enantioselective Synthesis and In Vivo Biological Evaluation of a Novel Fluorescent BODIPY α-Galactosylceramide," *ChemBioChem.*, 4(1): 27-33 (2003).

Wojno et al., "Amide Analogues of CD1d Agonists Modulate iNKT-Cell-Mediated Cytokine Production," *ACS Chem. Biol.*, 7(5): 847-855 (2012).

Japanese Patent Office, International Search Report in International Patent Application No. PCT/JP2017/008381 (dated May 30, 2017).

\* cited by examiner

COMPOUND OR SALT THEREOF, NATURAL KILLER T CELL ACTIVATOR, AND PHARMACEUTICAL COMPOSITION

CROSS-REFERENCE TO RELATED APPLICATIONS

This patent application is the U.S. national phase of International Patent Application No. PCT/JP2017/008381, filed Mar. 2, 2017, which claims the benefit of Japanese Patent Application No. 2016-057416, filed on Mar. 22, 2016, which are incorporated by reference in their entireties herein.

TECHNICAL FIELD

The present invention relates to a compound or a salt thereof, a natural killer T cell activating agent, and a pharmaceutical composition.

BACKGROUND ART

Natural killer T cell (hereinafter, sometimes referred to as "NKT cell") has an ability to improve secretion of various cytokines, and plays an important role in the immune system. Therefore, a compound capable of activating NKT cell to modulate production amount of various cytokines is thought to be available for the treatment of various immune-related diseases.

α-galactosylceramide (α-GalCer) is known to function as a ligand for a lipid antigen receptor (CD1d) on a dentritic cell and form a complex with the receptor to activate NKT cell via T cell receptor. Patent Document 1 discloses that α-galactosylceramide and analogues thereof activate NKT cell.

Document List

Patent Document

Patent Document 1: JP2004-131481 publication

SUMMARY OF THE INVENTION

Problems to be Solved by the Invention

An object of the present invention is to provide a novel compound or a salt thereof capable of activating natural killer T cell, a natural killer T cell activating agent containing such a compound or a salt thereof, and a pharmaceutical composition.

Means of Solving the Problems

The present inventors have found that a compound obtained by introducing an amide group or a partial structure thereof into a particular position in the α-GalCer structure can increase an amount of cytokine produced by NKT cell, and completed the present invention. More specifically, the present invention provides the followings.

(1) A compound represented by the formula (1) below:

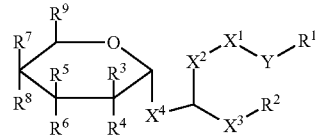

or a salt thereof,
wherein, in the formula (1),
Y is a group represented by any of the formulae (A) to (E) below,

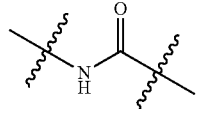

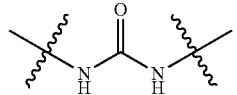

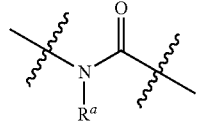

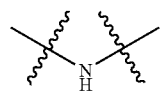

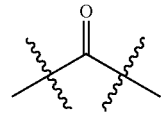

$R^1$ is a monovalent hydrocarbon group optionally having a substituent,
$R^2$ is a monovalent hydrocarbon group optionally having a substituent,
$R^a$ is a monovalent hydrocarbon group having a carbon number of 1 to 5,
$X^1$ is a divalent hydrocarbon group, wherein a part of carbon atoms constituting the hydrocarbon group is optionally substituted by a hetero atom,
$X^2$ is —NHCO—, —NMeCO—, —O—, or —OCO— (wherein, Me represents methyl group),
$X^3$ is —CH$_2$—, —CHOH—, —CHNH$_2$—, or —CONH—,
$X^4$ is —OCH$_2$—, —CH$_2$—CH$_2$—, —CH=CH—, —SCH$_2$—, or —NHCH$_2$—,
when $R^3$, $R^6$, and $R^8$ are hydrogen atoms,
$R^4$ is hydrogen atom, hydroxy group, —NH$_2$ or —NHCOCH$_3$,
$R^5$ is hydroxy group, an alkoxy group, an arylalkoxy group, or —OSO$_3$Na,
$R^7$ is hydroxy group, an alkoxy group, an arylalkoxy group, or —OSO$_3$Na,
$R^9$ is hydrogen atom, hydroxymethyl group, methyl group, an alkoxymethyl group, an arylalkoxymethyl group, —CH$_2$OSO$_3$Na, a group represented by the formula (VII), or a group represented by the formula (VIII),

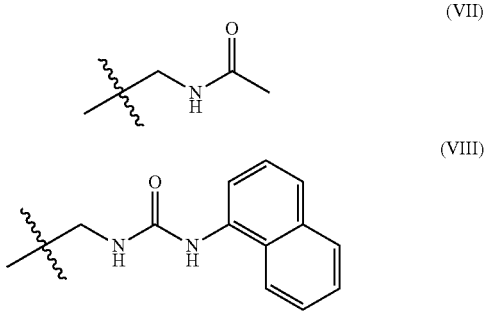

when R³, R⁶, and R⁷ are hydrogen atoms,
R⁴ is hydrogen atom, hydroxy group, —NH₂ or —NHCOCH₃,
R⁵ is hydroxy group, an alkoxy group, an arylalkoxy group, or —OSO₃Na,
R⁸ is hydroxy group, an alkoxy group, an arylalkoxy group, or —OSO₃Na,
R⁹ is hydrogen atom, hydroxymethyl group, methyl group, an alkoxymethyl group, an arylalkoxymethyl group, —CH₂OSO₃Na, a group represented by the formula (VII), or a group represented by the (VIII).
(2) The compound or a salt thereof described in (1), wherein a total carbon number of carbon(s) in the monovalent hydrocarbon group excluding substituent in R¹ and carbon (s) in the divalent hydrocarbon group in X¹ is 5 to 50.
(3) The compound or a salt thereof described in (1) or (2), wherein the monovalent hydrocarbon group in R¹ comprises a linear carbon chain having a primary carbon atom, and the primary carbon atom is substituted.
(4) A natural killer T cell activating agent which contains a compound or a salt thereof described in any of (1) to (3).
(5) A pharmaceutical composition which contains a compound described in any of (1) to (3) or a pharmacologically acceptable salt thereof.

Effect of the Invention

According to the present invention, a novel compound or a salt thereof capable of activating natural killer T cell, a natural killer T cell activating agent containing such a compound or a salt thereof, and a pharmaceutical composition can be provided.

MODE FOR CARRYING OUT THE INVENTION

Figure 1:
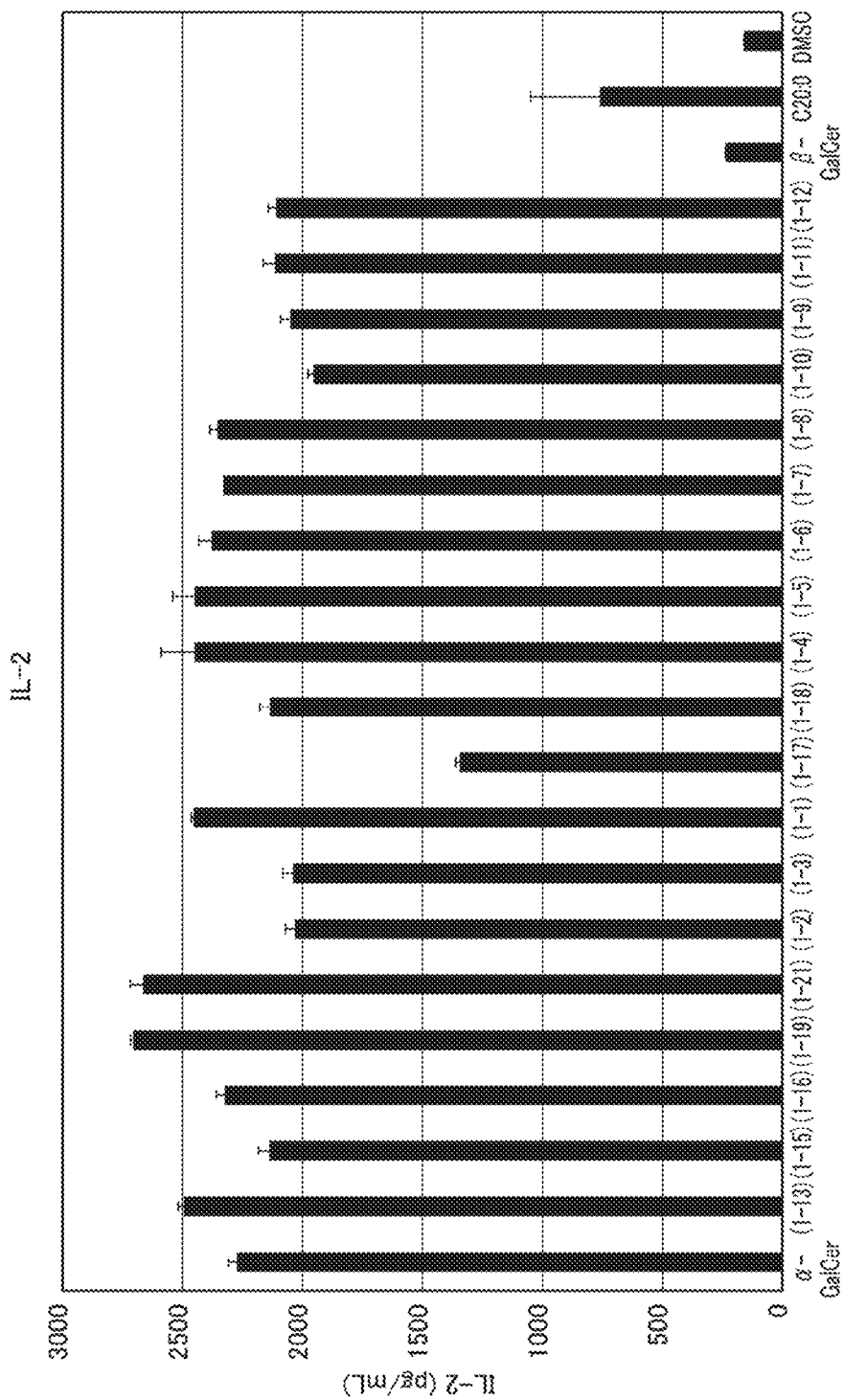
FIG. 1 is a graph illustrating the amount of IL-2 production in the experiment using hybridoma for the Example compounds and a control compound.

Although embodiments of the present invention are explained below, the present invention is not thus particularly limited.
<Compound>
The present invention is a compound represented by the formula (1) below:

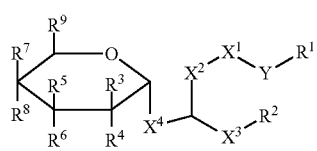

or a salt thereof; wherein
in the formula (1), Y is a group represented by any of the following formulae (A) to (E). $R^a$ is a monovalent hydrocarbon group having a carbon number of 1 to 5. In addition, in the present specification, a bond with a wavy line in each formula indicates a bond in each group to a bond destination.

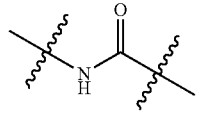

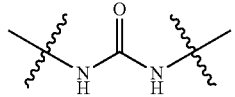

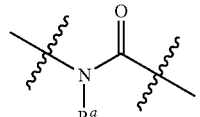

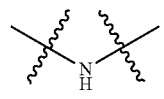

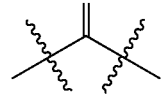

The compound of the present invention is characterized in that, the compound has a group having an amide or a partial structure thereof represented by any of the formulae (A) to (E) between $X^1$ (a divalent hydrocarbon group) and $R^1$ (a monovalent hydrocarbon group optionally having a substitutent). Although cytokine production capacity can be modulated by activating natural killer T cell, the compound of the present invention easily activates natural killer T cell due to possessing a group having an amide or a partial structure thereof bonded between $R^1$ and $X^1$, and exerts, for example, excellent effect to improve cytokine production amount. The reason for this is expected to be the fact that a group having an amide or a partial structure thereof has hydrophilic character, and when the compound of the present invention is recognized by CD1d as a ligand, the portion of the group having an amide or a partial structure thereof locates closer to a hydrophilic portion in CD1d due to the position of the group having an amide or a partial structure thereof, the compound exhibits high affinity to the hydrophilic portion in CD1d, and a complex of the compound and CD1d exerts excellent action to activate natural killer T cell.

The compound of the present invention is explained in detail below, the direction of the bond is explained by using the following symbols a to h in order to indicate the direction of bond of $X^1$, $X^2$, $X^3$, $X^4$ in the formula (1).

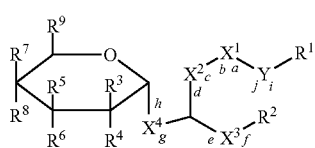
(1)

In the formula (1), Y is a group represented by any of the formulae (A) to (E). In the formula (c), $R^a$ is a monovalent hydrocarbon group having a carbon number of 1 to 5. The formulae (A) to (E) marked with i and j are shown in the formulae (a) to (e) below. The marks i and j in the formulae (A) to (E) correspond to the marks i and j in the formula (1). In other words, "i" in the following formulae (a) to (e) indicates the bond directing i side at Y in the formula (1), and "j" in the formulae (a) to (e) indicates the bond directing j side at Y in the formula (1).

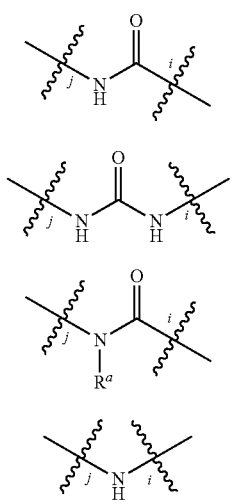

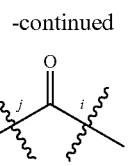
(E)

$R^a$ is a monovalent hydrocarbon group having a carbon number of 1 to 5, and is preferably methyl group.

In the formula (1), $R^1$ is a monovalent hydrocarbon group optionally having a substituent.

The monovalent hydrocarbon group in $R^1$ may be, for example, a monovalent aliphatic group or a monovalent aryl group. Examples of a monovalent aliphatic group include a substituted- or unsubstituted-alkyl group, alkenyl group, alkynyl group, cycloalkyl group, cycloalkenyl group, cycloalkynyl group and the like. The monovalent aliphatic group may be in any of linear, branched, and cyclic forms, or a form with a combination of these structures. The monovalent aliphatic group may be a saturated aliphatic group or an unsaturated aliphatic group, and may have one or more (for example, 1 to 5) unsaturated bond(s) in the molecule and/or at a terminal. When $R^1$ is a monovalent aryl group (phenyl group, naphthyl group, naphthoyl group, phenalenyl group, anthryl group, phenanthryl group, biphenyl group or the like), the monovalent aryl group may or may not have a substituent.

The carbon number of the monovalent hydrocarbon group (excluding the carbon number of the substituent) may be, for example, within the range of 1 to 50, preferably 2 to 45, more preferably 5 to 40, and still more preferably 10 to 30. It is preferable to contain a monovalent hydrocarbon group, particularly a linear carbon chain, and in such a case, the carbon number of the linear carbon chain is preferably 2 to 45, more preferably 5 to 40, and still more preferably 10 to 30.

Examples of the substituent of the monovalent hydrocarbon group in $R^1$ include, but are not particularly limited to, a halogen atom (fluorine atom and the like), hydroxy group, oxo group, carboxyl group, amino group ($-NH_2$), azido group, nitro group, thiol group, sulfo group, carbamyl group, an alkyl group, an alkenyl group, an alkynyl group, a cycloalkyl group, a cycloalkenyl group, a cycloalkynyl group, an aryl group, a hetero aryl group, a group derived from a heterocycle, an acyl group, an alkoxy group, an alkenyloxy group, an alkynyloxy group, an alkoxycarbonyl group, an acyloxy group, an aryloxy group, an alkylthio group, an alkenylthio group, an alkynylthio group, an alkylsulfonyl group, an alkenylsulfonyl group, an alkynylsulfonyl group, an alkylsulfinyl group, an alkenylsulfinyl group, an alkynylsulfinyl group, a mono- or di-alkylamino group, a carbonylamino group and the like. Among them, the substituent of the monovalent hydrocarbon group is preferably a halogen atom, hydroxy group, oxo group, carboxyl group, azido group, nitro group, thiol group, sulfo group, carbamyl group, an alkyl group, an alkenyl group, an alkynyl group, a cycloalkyl group, a cycloalkenyl group, a cycloalkynyl group, an aryl group, a hetero aryl group, a group derived from a heterocycle, an acyl group, an alkoxy group, an alkenyloxy group, an alkynyloxy group, an alkoxycarbonyl group, an acyloxy group, an aryloxy group, an alkylthio group, an alkenylthio group, an alkynylthio group, an alkylsulfonyl group, an alkenylsulfonyl group, an alkynylsulfonyl group, an alkylsulfinyl group, an alkenylsulfinyl group, an alkynylsulfinyl group, a mono- or di-alkylamino group, or a carbonylamino group. In addition, among the above substituents, an electron-donating group (a halogen atom, hydroxy group, amino group, a mono- or di-alkylamino group, an alkoxy group, an aryloxy group or the like) may be selected, or an electron withdrawing group (carboxyl group, an acyl group, carbamoyl group or the like) may be selected.

The substituent of the monovalent hydrocarbon group in $R^1$ may be a group represented by the following formula (IX). In the formula (IX), $n^1$ is an integer of 2 to 3, and $R^{10}$ is an aryl group or a group represented by the formula (X). Examples of the aryl group for $R^{10}$ are the same as the aryl group directly bonded to the monovalent hydrocarbon group. In the present specification, the numerical values in parentheses in the formulae indicate the number of carbon atoms.

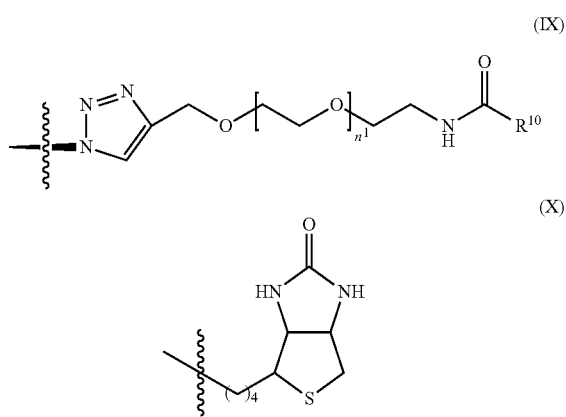

In addition, $R^1$ may by a group represented by the formula (XI) or the formula (XII) below, and may not be a group represented by the formula (XI) or the formula (XII).

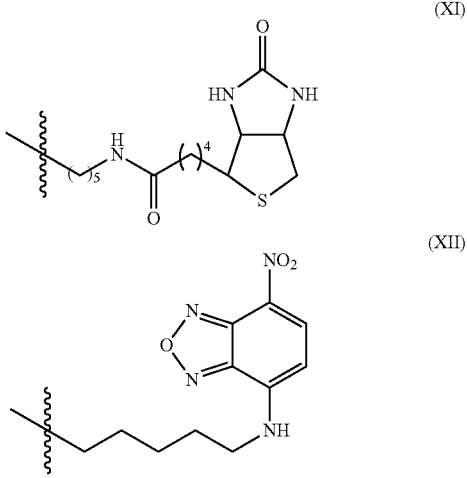

Among the substituents of the monovalent hydrocarbon group, examples of a halogen atom include fluorine atom, chlorine atom, bromine atom, iodine atom and the like, and fluorine atom and bromine atom are preferable.

Among the substituents of the monovalent hydrocarbon group, examples of an alkyl group include a linear or branched alkyl group including, for example, methyl group, ethyl group, n-propyl group, isopropyl group, n-butyl group, isobutyl group, sec-butyl group, tert-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, cyclopentyl group, cyclohexyl group and the like. Among the substituents of the monovalent hydrocarbon group, examples of an alkenyl group include a linear or branched alkenyl group including, for example, vinyl group, propenyl group, butenyl group, pentenyl group and the like. Among the substituents of the monovalent hydrocarbon group, examples of an alkynyl group include a linear or branched alkynyl group including, for example, ethynyl group, propargyl group, butynyl group, pentynyl group and the like. Among the substituents of the monovalent hydrocarbon group, examples of a cycloalkyl group include, for example, cyclopropyl group, cyclobutyl group, cyclopentyl group, cyclohexyl group, cycloheptyl group, cyclooctyl group, norbornyl group and the like. Among the substituents of the monovalent hydrocarbon group, examples of a cycloalkenyl group include, for example, 1-cyclobutenyl group, 1-cyclopentenyl group, 3-cyclopentenyl group, 1-cyclohexenyl group, 3-cyclohexenyl group, 3-cycloheptenyl group, or 4-cyclooctenyl group. Among the substituents of the monovalent hydrocarbon group, examples of a cycloalkynyl group include, for example, 1-cyclobutenyl group, 1-cyclopentenyl group, 3-cyclopentenyl group, 1-cyclohexenyl group, 3-cyclohexenyl group, 3-cycloheptenyl group, 4-cyclooctenyl group and the like.

Among the substituents of the monovalent hydrocarbon group, an aryl group is preferably a monocyclic to tricyclic aromatic group (e.g., phenyl group, naphthyl group, naphthoyl group, phenalenyl group, anthryl group, phenanthryl group and the like).

Among the substituents of the monovalent hydrocarbon group, examples of a hetero atom contained in the hetero aryl group or a group derived from a heterocycle include oxygen atom, sulfur atom, nitrogen atom and the like. The hetero aryl group indicates, for example, a group derived from three- to ten-membered hetelo ring, and may be an unsaturated ring or saturated cyclic. In addition, the hetero aryl group may be a monocycle or a fused ring (for example, condensed with 2 to 8 rings). Specific examples of the hetero aryl group include, for example, epoxy group, thienyl group, benzothienyl group, furyl group, benzofuranyl group, isobenzofuranyl group, isothiazolyl group, imidazolyl group, pyrazolyl group, pyrrolyl group, pyridyl group, pyrazinyl group, pyrimidinyl group, pyridazinyl group, indolyl group, isoindole group, quinolyl group, quinoxalyl group, isoquinolyl group, isoxazolyl group, tetrazolyl group, phthalazyl group, imidazopyridyl group, naphthyridyl group, quinazolyl group, acridinyl group and the like.

Among the substituents of the monovalent hydrocarbon group, an acyl group indicates, for example, formyl group, an alkyl (or cycloalkyl)-carbonyl group (for example, acetyl group, propionyl group, butyryl group, isobutyryl group, valeryl group, pivaloyl group, hexanoyl group and the like), an alkenyl (or cycloalkenyl)-carbonyl group (for example, acryloyl group, methacryloyl group and the like), an aryl (for example, a monocyclic to tricyclic aromatic group (e.g., phenyl group, naphthyl group, naphthoyl group, phenalenyl group, anthryl group, phenanthryl group, biphenyl group and the like))-carbonyl group or the like. The alkyl-carbonyl group may be, for example, linear or branched one with a carbon number of 1 to 12, and a carbon number of the cycloalkyl-carbonyl group may be, for example, 3 to 10. The alkenyl-carbonyl group may be, for example, linear or branched one with a carbon number of 2 to 12, and the cycloalkenyl-carbonyl group may have, for example, a carbon number of 3 to 10. The aryl-carbonyl group may have, for example, a carbon number of 6 to 14.

Among the substituents of the monovalent hydrocarbon group, examples of an alkoxy group include, for example, a linear or branched alkoxy group such as methoxy group, ethoxy group, propoxy group, isopropoxy group, butoxy group, tert-butoxy group or the like.

Among the substituents of the monovalent hydrocarbon group, the alkoxy in the alkoxycarbonyl group may be exemplified by the above-mentioned alkoxy group. Among the substituents of the monovalent hydrocarbon group, the acyl in the acyloxy group may be exemplified by the above-mentioned acyl group. Among the substituents of the monovalent hydrocarbon group, the aryl in the aryloxy group may be exemplified by the above-mentioned aryl group. Among the substituents of the monovalent hydrocarbon group, the alkyl in the alkylthio group, alkylsulfonyl group, alkylsulfinyl group and mono- or di-alkylamino group may be exemplified by the above-mentioned alkyl group. Among the substituents of the monovalent hydrocarbon group, the alkenyl in the alkenylthio group, alkenylsulfonyl group and alkenylsulfinyl group may be exemplified by the above-mentioned alkenyl group. Among the substituents of the monovalent hydrocarbon group, the alkynyl in the alkynylthio group, alkynylsulfonyl group and alkynylsulfinyl group may be exemplified by the above-mentioned alkynyl group.

The total number of carbon atom(s) in a substituent having carbon atom(s) among the substituents of the monovalent hydrocarbon group is preferably 1 to 30, more preferably 4 to 25, still more preferably 6 to 20. In addition, when the monovalent hydrocarbon group has a substituent, the total number of carbon atom(s) of the monovalent hydrocarbon group including the substituent may be within the range of 1 to 50, preferably 2 to 45, still more preferably 5 to 40, and further preferably 10 to 30.

Among the substituents of the monovalent hydrocarbon group, an alkyl group, an alkenyl group, an alkynyl group, a cycloalkyl group, a cycloalkenyl group, a cycloalkynyl group, an aryl group, a hetero aryl group, an acyl group, an alkoxy group, an alkenyloxy group, an alkynyloxy group, an alkoxycarbonyl group, an acyloxy group, an aryloxy group, an alkylthio group, an alkenylthio group, an alkynylthio group, an alkylsulfonyl group, an alkenylsulfonyl group, an alkynylsulfonyl group, an alkylsulfinyl group, an alkenylsulfinyl group, an alkynylsulfinyl group, a mono- or di-alkylamino group and a carbonylamino group may or may not be substituted. When substituted, they are preferably substituted by one or more groups selected from the substituent group constituting of a halogen atom, hydroxy group, amino group, an alkyl group, an alkylamino group, an alkenyl group, an alkynyl group, an aryl group, a hetero aryl group and an alkoxy group. These substituent groups may be the same substituents as the above-mentioned substituents of $R^1$. Particularly, among the substituents of the monovalent hydrocarbon group, an optionally substituted carbonylamino group is preferably a group represented by the following formula (XIII). In the formula (XIII), $R^{11}$ may be one or more among the above-mentioned substituent groups (the substituent groups selected from the group constituting of a halogen atom, hydroxy group, amino group, an alkyl group, an alkylamino group, an alkenyl group, an alkynyl group, an aryl group, a hetero aryl group and an alkoxy group), and particularly preferably hydrogen atom, an alkyl group (for example, a carbon number of 1 to 3), an alkynyl group (for example, a carbon number of 2 to 4).

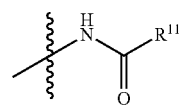

(XIII)

The number of the substituent of the monovalent hydrocarbon group is not particularly limited and may be appropriately selected in the range of, for example, 1 to 4. When the number of the substituent is two or more, each of the substituents may be the same or different. In addition, the substituents of the monovalent hydrocarbon group may be bonded to each other to form a ring, or a carbon atom in the structure of the monovalent hydrocarbon group and a substituent may be bonded to form a ring.

When the monovalent hydrocarbon group in $R^1$ contains a linear carbon chain, it is preferable that the linear carbon chain contains a primary carbon atom and the primary carbon atom is substituted. When the primary carbon atom is substituted, it is particularly preferably substituted by a hydrophobic group (a halogen atom, an alkyl group, an alkenyl group, an alkynyl group, an aryl group, a cycloalkyl group, a cycloalkenyl group, a cycloalkynyl group or the like) among the above-mentioned substituents. In addition, when the monovalent hydrocarbon group has two or more primary carbon atoms, the two or more primary carbon atoms may be substituted. Further, 2 to 3 hydrogen atoms may be substituted per one primary carbon atom contained in the monovalent hydrocarbon group.

In the formula (1), $R^2$ is a monovalent hydrocarbon group optionally having a substituent. Although $R^2$ can be exemplified by, for example, the same groups as those described above for $R^1$, it is particularly preferably an alkyl group, an alkoxy group optionally having a substituent, an acyloxy group optionally having a substituent, an alkenyl group optionally having a substituent, or an aryl group optionally having a substituent.

When $R^2$ is an alkyl group, the alkyl group may be either linear form or branched form, which is substituted or unsubstituted. The number of carbon atoms of the alkyl group (excluding the carbon number of the substituent) may be, for example, within the range of 1 to 50, but is preferably 2 to 40, more preferably 4 to 32, further preferably 6 to 25. When $R^2$ is an alkenyl group, the alkenyl group may be either linear form or branched form, which is substituted or unsubstituted. The number of carbon atoms of the alkenyl group (excluding the carbon number of the substituent) may be, for example, within the range of 2 to 50, but is preferably 2 to 40, more preferably 4 to 32, and further preferably 6 to 25. When $R^2$ is an alkoxy group, the alkoxy group may be either linear form or branched form, which is substituted or unsubstituted. The number of carbon atoms of the alkoxy group (excluding the carbon number of the substituent) may be, for example, within the range of 1 to 50, but is preferably 2 to 40, more preferably 4 to 32, and further preferably 6 to 25. When $R^2$ is an acyloxy group, the acyloxy group may be either linear form or branched form, which is substituted or unsubstituted, and can be exemplified by the same acyloxy groups as those described above for $R^1$. The number of carbon atoms of the acyloxy group (excluding the carbon number of the substituent) may be, for example, within the range of 1 to 50, but is preferably 2 to 40, more preferably 4 to 32, and further preferably 6 to 25. The "acyl" in the acyloxy group for $R^2$ is preferably an "alkyl-carbonyl group". When $R^2$ is an aryl group, the aryl group may be, substituted or unsubstituted, phenyl group, naphthyl group, naphthoyl group, phenalenyl group, anthryl group, phenanthryl group, biphenyl group or the like. The number of carbon atoms of the aryl group (excluding the carbon number of the substituent) may be, for example, within the range of 1 to 50, but is preferably 2 to 40, more preferably 4 to 32, and further preferably 6 to 25.

When $R^2$ is an alkyl group, an alkoxy group, an acyloxy group, an alkenyl group or an aryl group, substituents of each group is not particularly limited but exemplified by the same group as the substituent described above for $R^1$. When $R^2$ is an alkyl group, an alkoxy group, an acyloxy group, an alkenyl group or an aryl group, the total number of the carbon atoms of the substituent having a carbon atom among the respective substituents is preferably 1 to 30, more preferably 4 to 25, still more preferably 6 to 20. When $R^2$ is an alkyl group, an alkoxy group, an acyloxy group, an alkenyl group or an aryl group and each group has a substituent, the total number of carbon atoms contained in the alkyl group, the alkoxy group, the acyloxy group, the alkenyl group or the aryl group and the substituent thereof may be within the range of 1 to 50, but is preferably 2 to 40, more preferably 4 to 32, and further preferably 6 to 25. When $R^2$ is an alkyl group, an alkoxy group, an acyloxy group, alkenyl group or an aryl group, the number of the substituent thereof is not particularly limited and may be appropriately selected in the range of, for example, 1 to 4. When the number of the substituent is two or more, each of the substituents may be the same or different. In addition, the substituents of each group may be bonded to each other to form a ring. Alternatively, when $R^2$ is an alkyl group, an alkoxy group, an acyloxy group, alkenyl group or an aryl group, a carbon atom and a substituent in each group may be bonded to form a ring.

$R^2$ is preferably a group represented by the formulae (XIV) to (XVI).

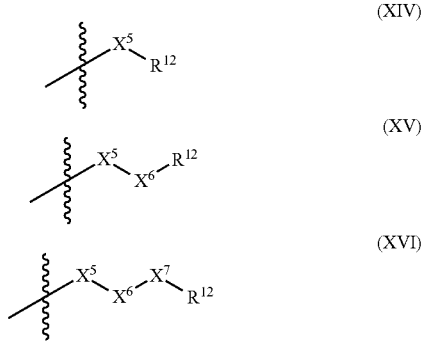

In the formulae (XIV) to (XVI), $X^5$ is represented by $-CR^{13}R^{14}-$, and each of $R^{13}$ and $R^{14}$ is independently hydrogen atom, a halogen atom or hydroxy group. $R^{12}$ represents an alkyl group optionally having a substituent, an alkenyl group optionally having a substituent, an acyloxy group optionally having a substituent, an alkoxy group optionally having a substituent or an aryl group optionally having a substituent, and the alkyl group, the alkenyl group, the acyloxy group, the alkoxy group, the aryl group and respective substituents thereof can be exemplified by the same groups as those of the alkyl group, the alkenyl group, the acyloxy group, the alkoxy group, the aryl group and respective substituents thereof described for $R^2$. In the formulae (XV) to (XVI), $X^6$ can be exemplified by the same groups as those of $X^5$. In the formula (XVI), $X^7$ can be exemplified by the same groups as those of $X^5$.

In the formula (1), $X^1$ is a divalent hydrocarbon group, and a carbon atom constituting the hydrocarbon group may be substituted with a hetero atom or may be unsubstituted.

A divalent hydrocarbon group in $X^1$ may be, for example, a divalent aliphatic group, or may be a divalent aryl group. In addition, the divalent aliphatic group may be any of linear, branched, or cyclic form, or a form with a combination of these structures. More specifically, it may be an alkylene group, an alkenylene group, an alkynylene group, a cycloalkylene group, a cycloalkenylene group, a cycloalkynylene group or the like, and may have a structure in which they are bonded to each other. The divalent aliphatic group may be a saturated aliphatic group or an unsaturated aliphatic group, and may have one or more (for example, 1 to 5) unsaturated bond(s) in the molecule and/or at a terminal. Examples of the divalent aryl group include, but are not limited to, phenyl group, naphthyl group, naphthoyl group, phenalenyl group, anthryl group, phenanthryl group, biphenyl group and the like. Examples of the optionally substituted hetero atom include oxygen atom, sulfur atom, nitrogen atom and the like, and as a mode of being substituted with a hetero atom, those substituted with a heteroaryl group may be substituted. The heteroaryl group may be exemplified by the same group as described above for the heteroaryl group which is a substituent in $R^1$.

The number of carbon atom(s) of the divalent hydrocarbon group in $X^1$ may be, for example, within the range of 1 to 50, but is preferably 2 to 45, more preferably 3 to 40, further preferably 4 to 30, and still more preferably 5 to 15. The number of carbon atom(s) of the divalent hydrocarbon group particularly preferably contains a linear carbon chain. The number of carbon atoms of the linear carbon chain is preferably 2 to 45, more preferably 5 to 40, and further preferably 10 to 30. Particularly, it is preferable that the divalent hydrocarbon group in $X^1$ has a linear carbon chain between N atom directly bonded to the a-side of $X^1$ and an atom in $X^2$ directly bonded to the b-side of $X^1$, as a continuous linear chain. The number of carbon atoms of such linear chain is preferably 2 to 45, more preferably 3 to 40, further preferably 4 to 30, and still more preferably 5 to 15.

The total carbon number of the number of carbon atoms of the monovalent hydrocarbon group in $R^1$ excluding the substituent and the number of carbon atoms of the divalent hydrocarbon group in $X^1$ is preferably 2 to 50 (3 to 50, 4 to 50, 5 to 50 or the like), preferably 3 to 40 (4 to 40, 5 to 40 or the like), further preferably 4 to 35 (5 to 35 or the like), still more preferably 5 to 30, and particularly preferably 6 to 27. Examples of such combination of a carbon number of the monovalent hydrocarbon group of $R^1$ excluding the substituent and a carbon number of the divalent hydrocarbon group of $X^1$ include, for example, a case where the carbon number of the monovalent hydrocarbon group in $R^1$ excluding the substituent is 1 to 25, and the carbon number of the divalent hydrocarbon group in $X^1$ is 1 to 25, a case where the carbon number of the monovalent hydrocarbon group in $R^1$ excluding the substituent is 2 to 20, and the carbon number of the divalent hydrocarbon group in $X^1$ is 2 to 20, a case where the carbon number of the monovalent hydrocarbon group in $R^1$ excluding the substituent is 3 to 15, and the carbon number of the divalent hydrocarbon group in $X^1$ is 3 to 15, and the like.

In general, a compound having α-GalCer structure tends to show decrease in its activity when the number of carbon atoms of the acyl group is short. However, the compound of the present invention does not easily show decrease in its activity even when the total carbon number of the number of carbon atoms of the monovalent hydrocarbon group of $R^1$ excluding the substituent and the number of carbon atoms of the divalent hydrocarbon group of $X^1$ is small (for example, 15 or less and the like), since the compound has a structure having amide bound between R, and $X^1$.

In the formula (1), $X^2$ is —NHCO—, —NMeCO—, —O—, or —OCO—. As used herein, Me represents methyl group. The following formulae (I) to (IV) represent —NHCO—, —NMeCO—, —O—, and —OCO— marked with the symbols c and d. The symbols c and d in the formulae (I) to (IV) correspond to the symbols c and d in the formula (1). That is, c in the following formulae (I) to (IV) indicates a bond of c-side direction in $X^2$ in the formula (1), and d in the following formulae (I) to (IV) indicates the bond of d-side direction in $X^2$ in the formula (1).

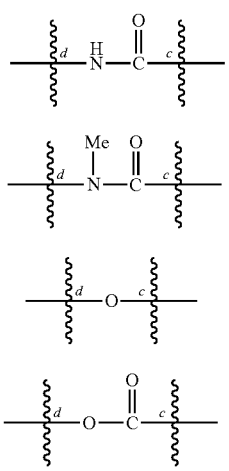

It is particularly preferable that $X^2$ is a group represented by —NHCO—.

In the formula (1), $X^3$ is —CH$_2$—, —CHOH—, —CHNH$_2$—, or —CONH—. The carbon atoms in —CHOH— and —CHNH$_2$— may be either S- or R-configuration. The following formulae (XVII) to (XX) show —CH$_2$—, —CHOH—, —CHNH$_2$—, and —CONH— marked with the symbols e and f. The symbols e and f in the formulae (XVII) to (XX) correspond to the symbols e and f in the formula (1). That is, e in the following formulae (XVII) to (XX) indicates a bond of e-side direction in $X^3$ in the formula (1), and f in the following formulae (XVII) to (XX) indicates the bond of f-side direction in $X^3$ in the formula (1).

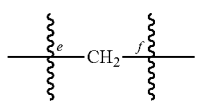

(XVII)

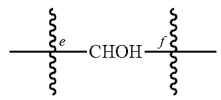

(XVIII)

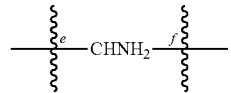

(XIX)

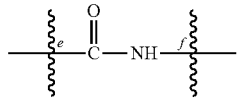

(XX)

When $X^3$ is —CH$_2$—, it is particularly preferable that $R^2$ is an acyloxy group optionally having a substituent, $X^2$ is a group represented by —OCO—, and $X^4$ described below is —OCH$_2$—.

In the formula (1), $X^4$ is —OCH$_2$—, —CH$_2$—CH$_2$—, —CH═CH— (cis-form or trans-form), —SCH$_2$—, or —NHCH$_2$—. $X^4$ is preferably —OCH$_2$— among them. The following formulae (XXI) to (XXV) show —OCH$_2$—, —CH$_2$—CH$_2$— and —CH═CH— marked with the symbols h and g. The symbols h and g in the formulae (XXI) to (XXV) correspond to the symbols h and g in the formula (1). That is, h in the following formulae (XXI) to (XXV) indicates a bond of h-side direction in $X^4$ in the formula (1), and g in the following formulae (XXI) to (XXV) indicates the bond of g-side direction in $X^4$ in the formula (1).

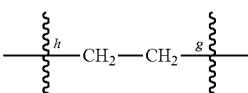

(XXI)

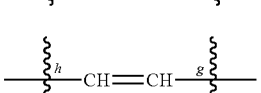

(XXII)

(XXIII)

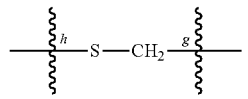

(XXIV)

(XXV)

In the formula (1), when $R^3$, $R^6$ and $R^8$ are hydrogen atom, $R^4$ is hydrogen atom, hydroxy group, —NH$_2$ or —NHCOCH$_3$, $R^5$ is hydroxy group, an alkoxy group, an arylalkoxy group or —OSO$_3$Na, $R^7$ is hydroxy group, an alkoxy group, an arylalkoxy group or —OSO$_3$Na, and $R^9$ is hydrogen atom, hydroxymethyl group, methyl group, an alkoxymethyl group, an arylalkoxymethyl group, —CH$_2$OSO$_3$Na, a group represented by the formula (VII), or a group represented by the formula (VIII).

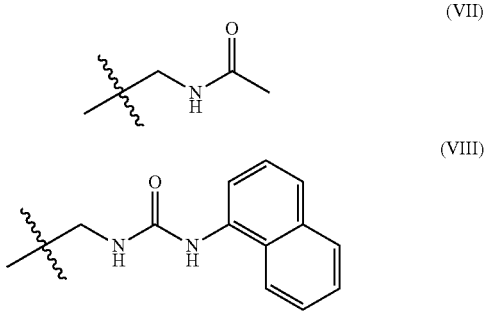

(VII)

(VIII)

In the formula (1), when $R^3$, $R^6$ and $R^7$ are hydrogen atom, $R^4$ is hydrogen atom, hydroxy group, —$NH_2$ or —$NHCOCH_3$, $R^5$ is hydroxy group, an alkoxy group, an arylalkoxy group or —$OSO_3Na$, $R^8$ is hydroxy group, an alkoxy group, an arylalkoxy group or —$OSO_3Na$, and $R^9$ is hydrogen atom, hydroxymethyl group, methyl group, alkoxymethyl group, an arylalkoxymethyl group, —$CH_2OSO_3Na$, a group represented by the above-mentioned formula (VII), or a group represented by the above-mentioned (VIII).

The "alkoxy" in an alkoxy group and an arylalkoxy group for $R^4$, $R^5$, $R^7$ and $R^8$ and an alkoxymethyl group and an arylalkoxymethyl group for $R^9$ can be, each independently, exemplified by the same groups as those described-above for the alkoxy group in a substituent of the monovalent hydrocarbon for $R^1$. The "aryl" in an arylalkoxy group for $R^4$, $R^5$, $R^7$ and $R^8$ and an arylalkoxymethyl group for $R^9$ can be, each independently, exemplified by the same groups as those described-above for the aryl group in a substituent of the monovalent hydrocarbon for R.

As a salt of the compound represented by the above-mentioned formula (1), a pharmacologically acceptable salt is preferable, but not particularly limited, and for example, a salt with an inorganic acid (hydrochloric acid, hydrobromic acid, hydroiodic acid, sulfuric acid, nitric acid, phosphoric acid or the like), a salt with an organic acid (formic acid, acetic acid, propionic acid, citric acid, tartaric acid, fumaric acid, butyric acid, oxalic acid, succinic acid, malonic acid, maleic acid, lactic acid, malic acid, carbonic acid, glutamic acid, aspartic acid, methanesulfonic acid, benzenesulfonic acid, p-toluenesulfonic acid or the like), a salt with an alkali metal (sodium, potassium or the like), a salt with an alkaline-earth metal (calcium, magnesium or the like), a salt with a metal (iron, zinc or the like) and the like are included. One kind of them may be used alone, or two or more of them may be used in combination. Those pharmacologically acceptable salts can be prepared according to a conventional method.

In the present invention, the compound represented by the above-mentioned formula (1) or a salt thereof may be in a form of hydrate or solvate.

<Production Method of the Compound>

An example of the production method of the compound represented by the above-mentioned formula (1) is explained below, but the production method of the compound of the present invention is not limited to this and can be appropriately modified according to a purpose. Specifically, the followings describe a production method of the compound represented by the formula (1-a) or the formula (1-b) among the compounds represented by the formula (1). The following sugar backbone in the compound represented by the formula (1-a) or the formula (1-b) means α-D-galactopyranosyl group among aldopyranose residues (residual groups obtained by removing hydroxyl group at a reducing terminal of an aldopyranose, and including, for example, α-D-galactopyranosyl, α-D-glucopyranosyl, β-D-galactopyranosyl, β-D-glucopyranosyl and the like).

In the formula (1-a), the monovalent hydrocarbon group in $R^1$ is a substituted or unsubstituted monovalent aliphatic group. The compound represented by the formula (1-a) below can be synthesized via steps (a) to (d).

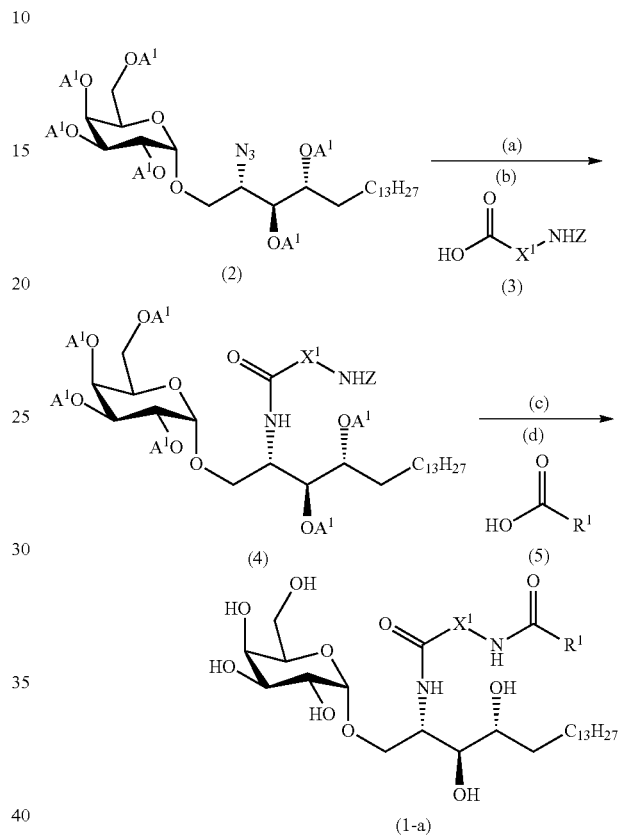

Step (a) is a step of obtaining a compound represented by the formula (6) from a compound represented by the formula (2), and can be carried out by, for example, Staudinger reaction using triphenylphosphine. In the formula, $A^1$ means a protecting group for hydroxyl group (e.g. benzyl group and the like).

Step (b) is a step of reacting a compound represented by the formula (6) and a compound represented by the formula (3) to obtain a compound represented by the formula (4). The reaction in step (b) can be carried out by using a dehydration condensing agent (for example, water-soluble carbodiimide). Detailed scheme of step (a) and step (b) is shown below.

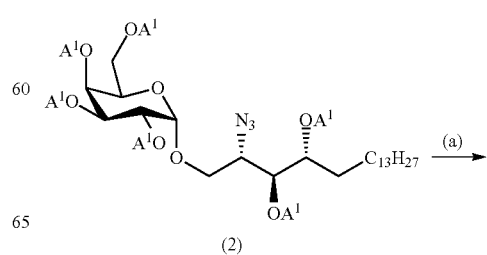

-continued

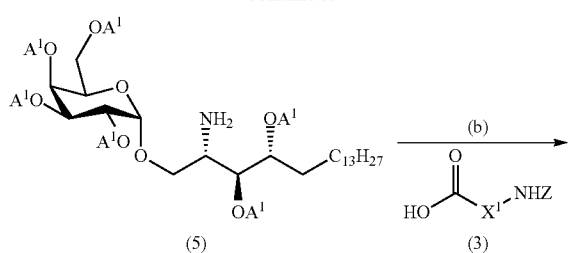

(5) (3)

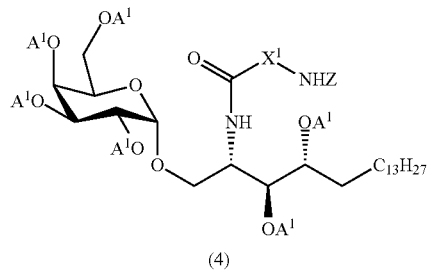

(4)

Step (c) is a step of deprotecting $A^1$ in a compound represented by the formula (4) to obtain a compound represented by the formula (7). For the deprotection reaction, a known method for deprotecting hydroxyl group may be used according to the kind of protecting group.

Step (d) is a step of subjecting a compound represented by the formula (7) and a compound represented by the formula (5) to the dehydration condensation reaction to obtain a compound represented by the formula (1-a). The dehydration condensation reaction can be carried out by using a known dehydration condensing agent. Detailed scheme of step (c) and step (d) is shown below.

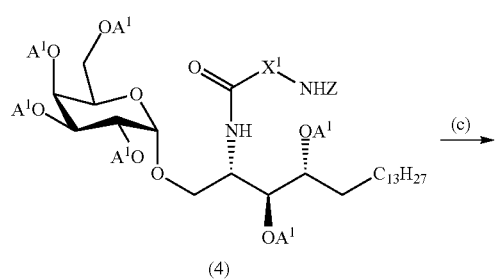

(4)

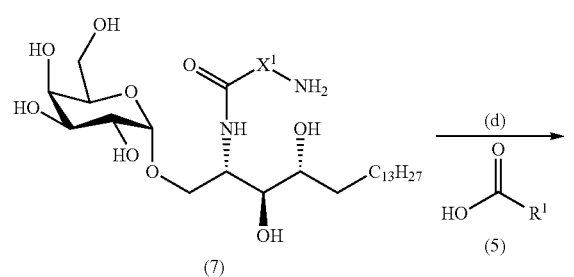

(7) (5)

-continued

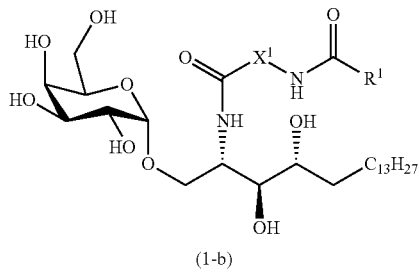

(1-a)

In a compound represented by the formula (1-b), the monovalent hydrocarbon group in R is a substituted or unsubstituted aryl group. A compound represented by the formula (1-b) can be synthesized via steps (e) to (i).

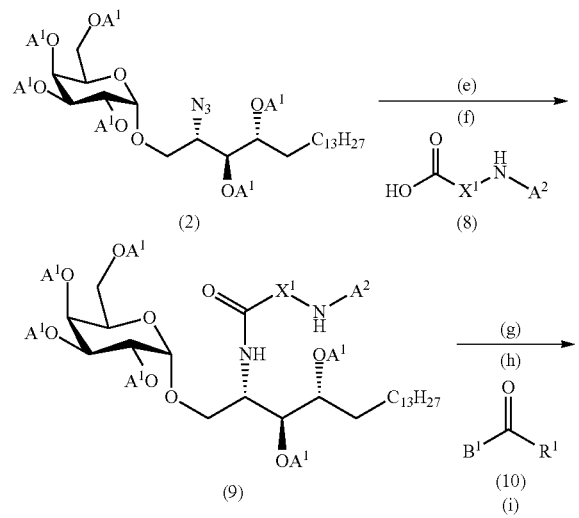

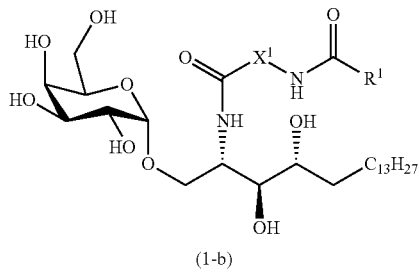

(1-b)

Step (e) is a step of obtaining a compound represented by the formula (11) from a compound represented by the formula (2) and can be carried out by the same method as the above step (a). In the formula, $A^2$ means a protecting group of a primary amino group (for example, trifluoroacetyl group and the like), and $A^2$ is preferably a group which can be deprotected under a condition different from A.

Step (f) is a step of reacting a compound represented by the formula (11) and a compound represented by the formula (8) to obtain a compound represented by the formula (9). The reaction in step (f) can be carried out by the same method as the above-mentioned step (b). Detailed scheme of step (e) and step (f) is shown below.

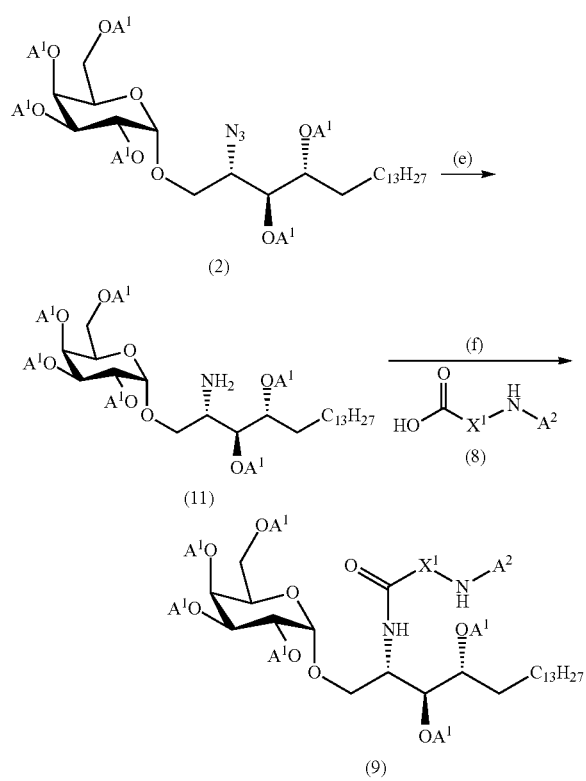

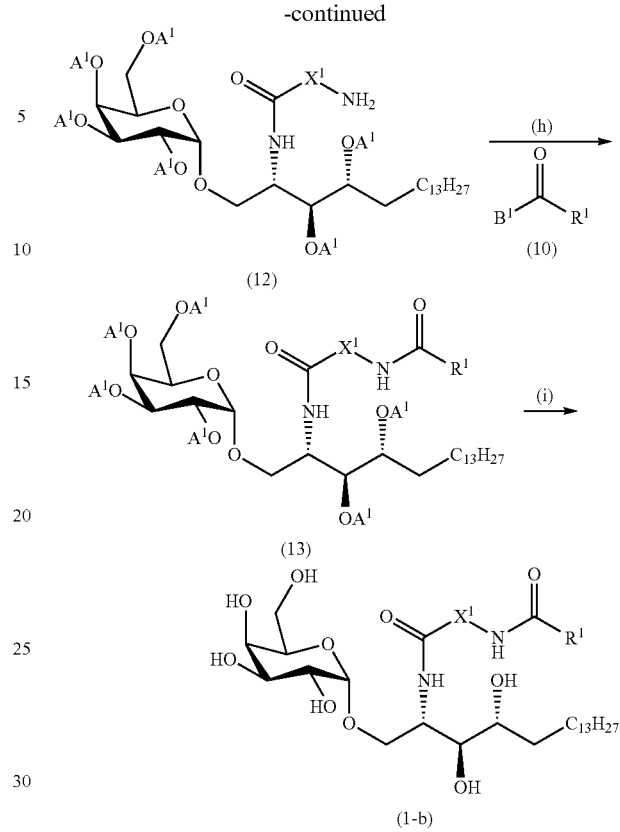

Step (g) is a step of deprotecting $A^2$ from a compound represented by the formula (9) to obtain a compound represented by the formula (12). The deprotection may be appropriately modified according to the kind of $A^2$, for example, when the protecting group $A^2$ is trifluoroacetyl group, deprotection can be carried out by placing it under strong alkali condition.

Step (h) is a step of reacting a compound represented by the formula (12) and a compound represented by the formula (10) to obtain a compound represented by the formula (13). In the formula, $B^1$ means hydroxy group or a halogen atom. This reaction can be carried out by a known method (for example, when $B^1$ is hydroxy group, dehydration condensation reaction may be carried out with water-soluble carbodiimide, and when $B^1$ is a halogen atom, it may be reacted by using a base).

Step (i) is a step of deprotecting A in a compound represented by the formula (13) to obtain a compound represented by the formula (1-b). For the deprotection reaction, the same method as the above-mentioned step (c) can be used. Detailed scheme of step (g), step (h) and step (i) is shown below.

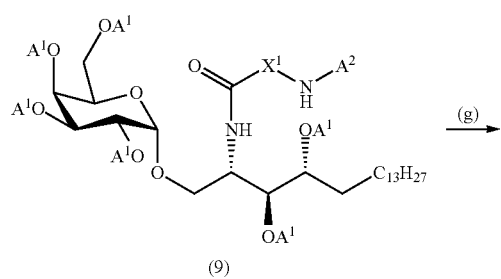

The above is an example of a production method for the compound represented by the formula (1-a) or the formula (1-b) which is a part of the compounds represented by the formula (1) described above, and other compounds can be produced by an appropriate modification. For example, a modification for producing an objective compound among the compounds represented by the formula (1) may be made during, before or after the each step. Alternatively, a modification for producing the objective compound may be made after producing a compound represented by the formula (1-a) or the formula (1-b). These modifications can be carried out by using a known method. They can be carried out by referring to, for example, "Xavier Laurent, et al., "Switching Invariant Natural Killer T (iNKT) Cell Response from Anticancerous to Anti-Inflammatory Effect: Molecular Bases", J. Med. Chem. 2014, 57, 5489-5508" or the like. For synthesis of the compound represented by the formula (2), "Eur. J. Org. Chem. 1998, 2, 291-298", "Tetrahedron 2005, 61, 1855-1862" or the like may be referred to.

For production of the compound represented by the formula (1), a known method may be used as necessary, and, for example, JP-A-2004-131481, WO 93/5055, WO 94/2168, WO 94/9020, WO 94/24142 or the like may be referred to.

<NKT Cell Activating Agent>

Since the above-mentioned compound represented by the formula (1) can activate NKT cell, the above-mentioned compound represented by the formula (1) or a pharmacologically acceptable salt thereof can be used as an ingredient of a NKT cell activating agent. In the present invention, "NKT cell activation" means any one or both of augmentation of the activity of NKT cell and enhancement of the growth of NKT cell.

Since the above-mentioned compound represented by the formula (1) can activate NKT cell, the NKT cell activating agent of the present invention can regulate production amount of various cytokines by activating NKT cells. In other words, presence or absence of activation of NKT cell can be evaluated by using cytokine production amount as an index. Specifically, in respect of cytokines whose production amount is to be retulated, the NKT cell activating agent of the present invention can be used for improving production amount of IFN(interferon)-γ, improving production amount of IL(interleukin)-2, improving production amount of IL-4, improving production amount of IL-10, improving production amount of IL-13, improving production amount of IL-9, improving production amount of IL-17, improving production amount of IL-22 or the like. It is preferably used for improving production amount of at least one or more cytokines selected from the group consisting of at least IFN-γ, IL-2, IL-4, and IL-10.

In addition, the NKT cell activating agent of the present invention may be used for obtaining an effect directly or indirectly expected by the regulation of production amount of various cytokines, for example, may be used for treating or preventing a disease on which therapeutic or prophylactic effect can be directly or indirectly expected by regulating production amount of a cytokine. More specifically, the NKT cell activating agent of the present invention may be used for treating or preventing a disease on which therapeutic or prophylactic effect can be directly or indirectly expected by improving production amount of, for example, IFN-γ. Examples of a disease on which therapeutic or prophylactic effect can be directly or indirectly expected by improving production amount of IFN-γ include, for example, cancer (colon cancer, breast cancer, lung cancer, prostate cancer, brain tumor, hepatic cancer, ovarian cancer, skin cancer, hematological malignancy (chronic myelogenous leukemia, malignant lymphoma or the like)), infections (viral disease, bacterial infection or the like), type 1 diabetes and the like. Examples of an effect directly or indirectly expected by IL-4 production include suppression of allergic inflammation, therapeutic or prophylactic effect on type 1 diabetes and the like. Examples of an effect directly or indirectly expected by improving production amount of IL-10 include treatment or prevention of an autoimmune disease (for example, systemic lupus erythematosus, systemic scleroderma, ulcerative colitis, multiple sclerosis, encephalomyelitis, type I diabetes and the like), maintenance of transplantation immuntolerance and the like. Examples of an effect directly or indirectly expected by production of IL-13 or IL-9 include suppression effect on allergic inflammation. Examples of an effect directly or indirectly expected by production of IL-17 or IL-22 include therapeutic or prophylactic effect on non-allergic asthma, autoimmune disease and the like.

<Pharmaceutical Composition>

The present invention includes a pharmaceutical composition containing the above-mentioned compound represented by the formula (1) or a pharmacologically acceptable salt thereof.

The pharmaceutical composition of the present invention may be formulated. The dosage form is not particularly limited, but it may be formulated into, for example, injection (intravenous injection (including drip infusion), intramuscular injection, intraperitoneal injection, subcutaneous injection or the like), tablet, capsule, liquid, suppository, ointment or the like. In the case of preparation for injection, it may be provided in the form of a unit dosage ampoule or a multiple dosage container.

These various preparations can be produced by a conventional method appropriately using an excipient, a filler, a binder, a wetting agent, a disintegrant, a lubricant, a surfactant, a dispersant, a buffer, a preservative, a solubilizing agent, a preservative, a flavoring agent, a soothing agent, a stabilizer, an isotonizing agent or the like, which are generally used for drug formulation. The pharmaceutical composition of the present invention may or may not have a component other than the above-mentioned compound represented by the formula (1) or a pharmacologically acceptable salt thereof for the purpose of formulation above.

The method for administering the therapeutic drug of the present invention is not particularly limited, and it may be oral administration or parenteral administration, and it can be appropriately selected depending on the dosage form.

EXAMPLES

An embodiment of the present invention is explained below.

Explanation of each abbreviation used in each example is described below.

Meaning of Abbreviations

MeOH methanol
EtOH ethanol
NMR nuclear magnetic resonance
TMS tetramethylsilane
TMSCI chlorotrimethylsilane
TMSI iodotrimethylsilane
TFA trifluoroacetic acid
CDCl$_3$ deuterochloroform
TfN$_3$ trifluoromethanesulfonylazide
TrCl trityl chloride
BnBr benzyl bromide
DMF N,N-dimethylformamide
DMAP N,N-dimethyl-4-aminopyridine
PdCl$_2$ palladium chloride
Ac$_2$O acetic anhydride
Et$_3$N triethylamine
TBAI tetrabutylammonium iodide
DIEA diisopropylethylamine
DIPEA N,N-diisopropylethylamine
MS molecular sieve
MeI iodomethane
PPh$_3$ triphenylphosphine
WSC water-soluble carbodiimide
THF tetrahydrofuran
DMT-MM 4-(4,6-dimethoxy-1,3,5-triazin-2-yl)-4-methyl-morpholinium chloride
ZCl benzyl chloroformate
EtOAc ethyl acetate
HOBt 1-hydroxybenzotriazole
m-CPBA meta-chloroperbenzoic acid
Z benzyloxycarbonyl group
Boc tertiary butoxycarbonyl group
NsCl 2-nitrobenzenesulfonyl chloride
Ns 2-nitrobenzenesulfonyl group
OBn benzyloxy group
OMe methoxy group
Ph phenyl group In each step of the following synthesis example, all moisture-sensitive reactions were carried out using a syringe and septum cap under an argon atmosphere. All glassware was dried in an oven at 80° C. for 2 hr prior to use. Reactions at −78° C. employed a CO$_2$-MeOH bath. Analytical thin layer chromatography (TLC) was carried out with Silica gel 60 F$_{254}$ Plates (manufactured by Merck, 0.25 mm thickness). For flash chromatography, Silica gel 60 N (spherical neutral, 40-50 μm, manufactured by Kanto Chemical Co.) was employed. Melting points were measured by a hot stage melting point apparatus. All NMR spectral data were recorded on a JEOL ECX-400 spectrometer (manufactured by JEOL Ltd.) for $^1$H (400 MHz) and $^{13}$C (100 MHz). Chemical shifts (δ, unit ppm) were measured relative to TMS in CDCl$_3$ as an internal standard ($^1$H NMR) or the residual CHCl$_3$ signal ($^{13}$C NMR). $^1$H NMR spectra are tabulated as follows: chemical shift, multiplicity (b=broad, s=singlet, d=doublet, t=triplet, q=quartet, m=multiplet), number of protons, and coupling constant(s). Exact mass (HRMS) spectra were recorded on an electrospray ionization quadrupole time of flight (ESI-QTOF) mass spectrometer (micrOTOF-QII-HC; manufactured by BRUKER).

Synthesis Example 1

Synthesis of 12-(((benzyloxy)carbonyl)amino)dodecanoic acid (Compound (3-a))

To a stirred suspension of compound (14-a) (1.0 g, 4.6 mmol) in dioxane (7.0 mL) and H$_2$O (7.0 mL) were added Na$_2$CO$_3$ (2.4 g, 23 mmol) and ZCl (0.76 mL, 5.5 mmol) at room temperature. After stirring for 31 hr at this temperature, the obtained mixture was diluted with EtOAc and washed with saturated KHSO$_4$ aqueous solution, and dried over Mg$_2$SO$_4$. Concentration under reduced pressure followed by recrystallization from hexane/EtOAc (8/1) gave compound (3-a) as a white solid (550 mg, 34% yield). Analysis results of NMR spectrum and reaction scheme are shown below.

$^1$H NMR (400 MHz, CDCl$_3$) δ 1.25-1.35 (m, 14H), 1.45-1.51 (m, 2H), 1.60-1.65 (m, 2H), 2.34 (t, J=7.6 Hz, 2H), 3.18 (dt, J=7.3, 6.3 Hz, 2H), 4.73-4.77 (m, 1H), 5.09-5.15 (m, 2H), 7.30-7.38 (m, 5H);

$^{13}$C NMR (100 MHz, CDCl$_3$) δ 24.6, 26.7, 28.8, 29.0, 29.1, 29.2, 29.3, 29.4 (2C), 34.0, 41.1, 66.6, 128.1 (3C), 128.5 (2C), 136.6, 156.4, 179.3; HRMS (ESI-TOF) calcd C$_{20}$H$_{30}$NO$_4$:(M–H)$^-$, 348.2180; found: (M–H)$^-$, 348.2188.

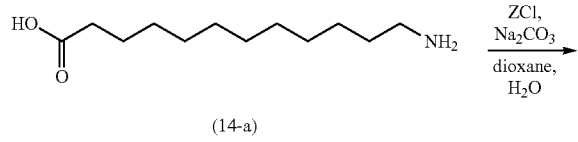

(14-a)

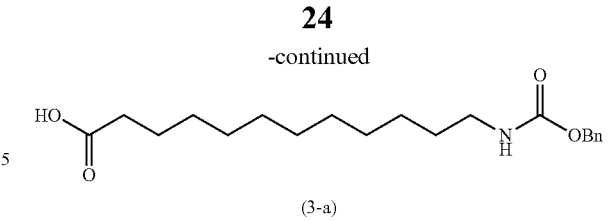

(3-a)

Synthesis of benzyl (12-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)amino)-12-oxododecyl)carbamate (Compound (4-a))

To a stirred solution of compound (2-a) (200 mg, 0.19 mmol) in benzene (12 mL) and H$_2$O (0.48 mL) was added PPh$_3$ (125 mg, 0.48 mmol), and the obtained mixture was stirred at 50° C. for 12 hr. The obtained mixture was concentrated under reduced pressure, and azeotroped three times with benzene. The obtained residue was dissolved in THF (14 mL). 12-(((Benzyloxy)carbonyl)amino)dodecanoic acid (compound (3-a)) (179 mg, 0.51 mmol) and WSCI·H$_2$O (98 mg, 0.51 mmol) were added to the stirred mixture at room temperature. The obtained mixture was stirred at this temperature for 24 hr, and diluted with saturated NaHCO$_3$ aqueous solution. The whole mixture was extracted with EtOAc. The extract was washed with saturated NaHCO$_3$, brine, and dried over MgSO$_4$, and concentrated under reduced pressure to give an oily residue. This residue was purified by flash chromatography over silica gel with n-hexane-EtOAc (4:1) to give compound (4-a) as a white solid (195 mg, 76% yield). Analysis results of NMR spectrum and reaction scheme are shown below.

$^1$H NMR (400 MHz, CDCl$_3$) δ:0.88 (t, J=6.8 Hz, 3H), 1.20-1.29 (m, 38H), 1.42-1.53 (m, 6H), 1.88-1.98 (m, 2H), 3.14-3.20 (m, 2H), 3.41 (dd, J=8.7, 6.3 Hz, 1H), 3.41 (dd, J=8.7, 6.3 Hz, 1H), 3.51-3.47 (m, 2H), 3.73 (dd, J=10.0, 5.0 Hz, 1H), 3.86 (dd, J=10.0, 3.4 Hz, 11H), 3.88-3.95 (m, 2H), 4.00-4.06 (m, 2H), 4.13-4.17 (m, 1H), 4.35-4.38 (m, 1H), 4.42 (d, J=11.7 Hz, 1H), 4.47 (d, J=11.7 Hz, 1H), 4.52 (d, J=11.7 Hz, 1H), 4.60-4.54 (m, 2H), 4.64 (d, J=11.7 Hz, 1H), 4.68-4.73 (m, 1H), 4.72-4.82 (m, 4H), 4.85 (d, J=3.4 Hz, 1H), 4.92 (d, J=11.7 Hz, 1H), 5.09 (s, 2H), 6.15 (d, J=8.3 Hz, 1H), 7.38-7.22 (m, 35H); 13C NMR (100 MHz, CDCl$_3$) δ 14.1, 22.7, 25.6, 26.0, 26.7, 29.3, 29.4 (3C), 29.5, 29.6, 29.7 (12C), 29.8, 29.9, 31.9, 36.6, 41.1, 50.3, 66.5, 67.9, 69.2, 69.9, 71.7, 72.9, 73.4, 73.6 (2C), 74.7 (2C), 76.6, 78.6, 78.9, 80.1, 99.6, 127.4 (2C), 127.5 (3C), 127.6, 127.7, 127.8 (8C), 127.9 (2C), 128.0, 128.1, 128.2 (2C), 128.3 (8C), 128.4 (4C), 128.5 (2C), 136.6, 137.5, 138.4, 138.6, 138.7 (2C), 139.8, 156.8, 172.7; HRMS (ESI-TOF) calcd C$_{86}$H$_{114}$N$_2$NaO$_{11}$: (M+Na)+, 1373.8315; found: (M+Na)+, 1373.8315.

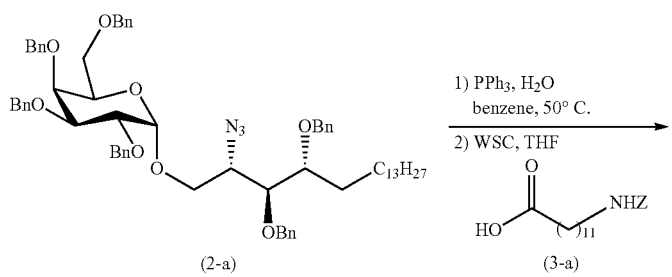

(2-a)     (3-a)

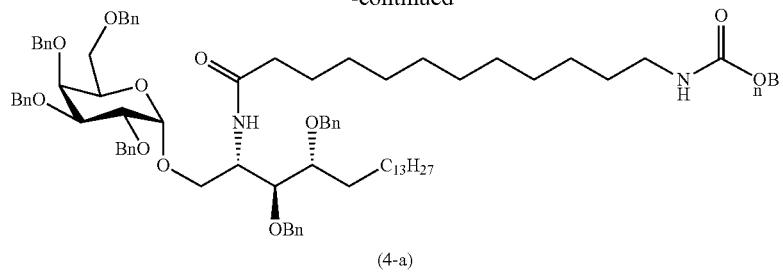

(4-a)

Synthesis of N-(12-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-12-oxododecyl)tridecanamide (Compound (1-1))

A mixture of compound (4-a) (15 mg, 0.010 mmol) and Pd(OH)$_2$/C (20% wt on carbon, 5 mg, 0.007 mmol) in EtOH (1.2 mL) and CH$_2$Cl$_2$ (0.4 mL) was stirred for 7 hr at room temperature under H$_2$ atmosphere (0.5 MPa), and then filtrated through Celite pad with EtOH/CH$_2$Cl$_2$ (3:1). The filtrate was concentrated under reduced pressure to give a crude amine as a colorless oil. This amine was dissolved in EtOH (1.5 mL) and CH$_2$Cl$_2$ (0.5 mL). Tridecanoic acid (compound 5-a) (6.4 mg, 0.030 mmol) and DMT-MM (8.3 mg, 0.030 mmol) were added to the stirred mixture at room temperature. The obtained mixture was stirred at this temperature for 12 hr, and diluted with saturated NaHCO$_3$ aqueous solution. The whole mixture was extracted with EtOAc. The extract was washed with saturated NaHCO$_3$, brine, and dried over MgSO$_4$, and concentrated under reduced pressure to give an oily residue, which was purified by flash chromatography over silica gel with CHCl$_3$-MeOH (9:1) to give compound (1-1) as a white solid (4.7 mg, 54% yield). Analysis results of NMR spectrum and reaction scheme are shown below.

$^1$H NMR (400 MHz, CDCl$_3$:CD$_3$OD=10:1) δ 0.88 (t, J=6.5 Hz, 6H), 1.20-1.35 (m, 56H), 1.43-1.53 (m, 2H), 1.55-1.70 (m, 6H), 2.15 (t, J=8.1 Hz, 2H), 2.19 (t, J=8.1 Hz, 2H), 3.15-3.23 (m, 2H), 3.50-3.56 (m, 2H), 3.65-3.75 (m, 3H), 3.76-3.83 (m, 3H), 3.89 (dd, J=10.1, 4.0 Hz, 1H), 3.96 (d, J=4.0 Hz, 1H), 4.16-4.22 (m, 1H), 4.91 (d, J=4.0 Hz, 1H); $^{13}$C NMR (100 MHz, CDCl$_3$:CD$_3$OD=10:1) 14.1 (2C), 22.8, 25.9 (2C), 26.0, 26.9, 29.3 (2C), 29.4 (6C), 29.5 (2C), 29.7 (2C). 29.8 (12C), 29.9, 32.0, 32.8, 36.6, 36.8, 39.5, 50.4, 62.1, 67.7, 69.0, 69.9, 70.3, 70.7, 72.2, 75.0, 99.7, 174.3, 174.4; HRMS (ESI-TOF) calcd C$_{49}$H$_{96}$N$_2$NaO$_{10}$: (M+Na)$^+$, 895.6957 found: (M+Na)$^+$, 895.6972.

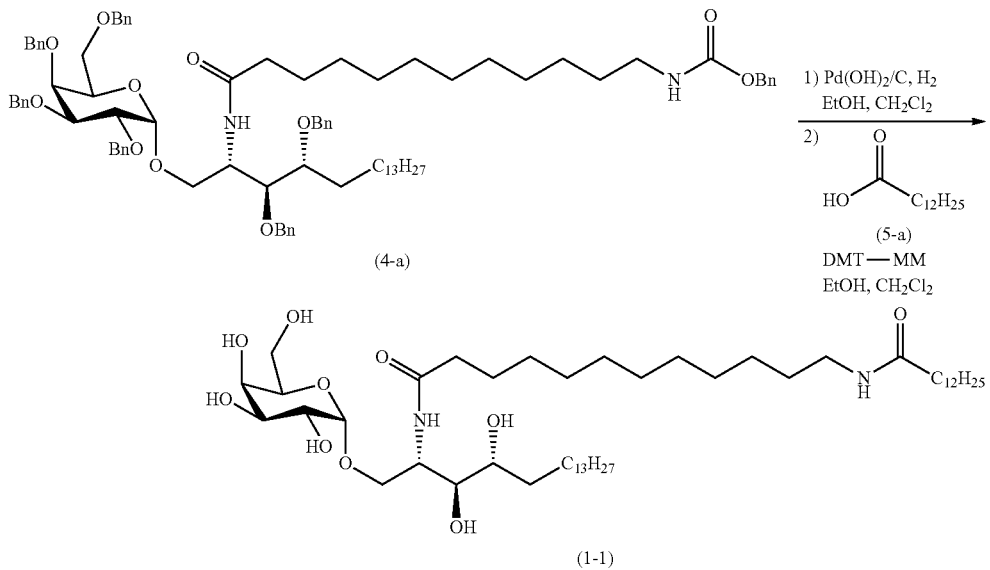

Synthesis Example 2

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-12-hexanamidedodecanamide (Compound (1-2))

In the same manner as the synthesis method of compound (1-1) from compound (4-a) except that compound (5-b) was used instead of compound (5-a), compound (4-a) (15.0 mg, 0.011 mmol) was converted to compound (1-2) as a white solid (1.6 mg, 21% yield). Analysis results of NMR spectrum and reaction scheme are shown below.

$^1$H NMR (400 MHz, CDCl$_3$:CD$_3$OD=10:1) δ 0.88 (t, J=6.3 Hz, 3H), 0.90 (t, J=6.3 Hz, 3H), 1.25-1.32 (m, 42H), 1.46-1.50 (m, 2H), 1.58-1.65 (m, 6H), 2.16 (t, J=8.0 Hz, 2H), 2.20 (t, J=8.0 Hz, 2H), 3.17-3.21 (m, 2H), 3.49-3.54 (m, 2H), 3.70-3.73 (m, 3H), 3.76-3.82 (m, 3H), 3.89 (dd,

J=11.0, 3.8 Hz, 1H), 3.95 (d, J=3.8 Hz, 1H), 4.19 (d, J=3.8 Hz, 1H), 4.91 (d, J=3.8 Hz, 1H); $^{13}$C NMR (100 MHz, CDCl$_3$:CD$_3$OD=10:1) δ 14.0, 14.2, 22.5, 22.8, 25.6 (2C), 25.9 (2C), 26.9, 29.2, 29.3 (2C), 29.4, 29.5 (3C), 29.7, 29.8 (6C), 29.9, 31.5, 32.0, 32.8, 36.6, 36.7, 39.6, 50.3, 62.1, 67.7, 69.0, 69.9, 70.3, 70.6, 72.2, 75.0, 99.7, 174.3, 174.4: HRMS (ESI-TOF) calcd C$_{42}$H$_{82}$N$_2$NaO$_{10}$: (M+Na)$^+$, 797.5862; found: (M+Na)$^+$, 797.5870.

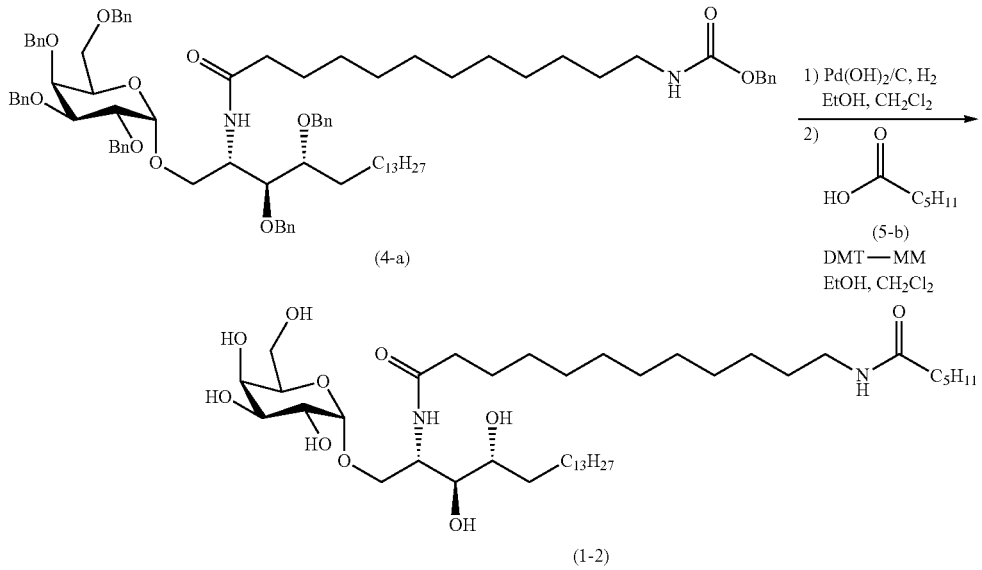

Synthesis Example 3

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-12-heptanamidedodecanamide (Compound (1-3))

In the same manner as the synthesis method of compound (1-1) from compound (4-a) except that compound (5-c) was used instead of compound (5-a), compound (4-a) (25.8 mg, 0.019 mmol) was converted to (compound (1-3)) as a white solid (3.8 mg, 25% yield). Analysis results of NMR spectrum and reaction scheme are shown below.

$^1$H NMR (400 MHz, CDCl$_3$:CD$_3$OD=10:1) δ 0.88 (t, J=6.4 Hz, 6H), 1.24-1.31 (m, 44H), 1.45-1.50 (m, 2H), 1.57-1.64 (m, 6H), 2.16 (t, J=7.7 Hz, 2H), 2.20 (t, J=7.7 Hz, 2H), 3.16-3.22 (m, 2H), 3.51-3.55 (m, 2H), 3.69-3.73 (m, 3H), 3.75-3.81 (m, 3H), 3.89 (dd, J=10.0, 3.8 Hz, 1H), 3.94-3.97 (m, 1H), 4.17-4.20 (m, 1H), 4.90-4.92 (m, 1H); $^{13}$C NMR (100 MHz, CDCl$_3$:CD$_3$OD=10:1) δ 13.9 (2C), 22.5 (2C), 25.4, 25.7, 25.8, 26.2, 26.5, 28.5, 28.6, 29.1, 29.2 (2C), 29.4 (2C), 29.5, 29.6 (7C), 29.7, 31.7, 31.8, 32.6, 36.2, 36.5, 39.1, 50.2, 61.8, 67.4, 68.8, 69.6, 70.1, 70.5, 72.0, 74.8, 99.5, 174.1, 174.2: HRMS (ESI-TOF) calcd C$_{43}$H$_{84}$N$_2$NaO$_{10}$: (M+Na)$^+$, 811.6018; found: (M+Na)$^+$, 811.6024.

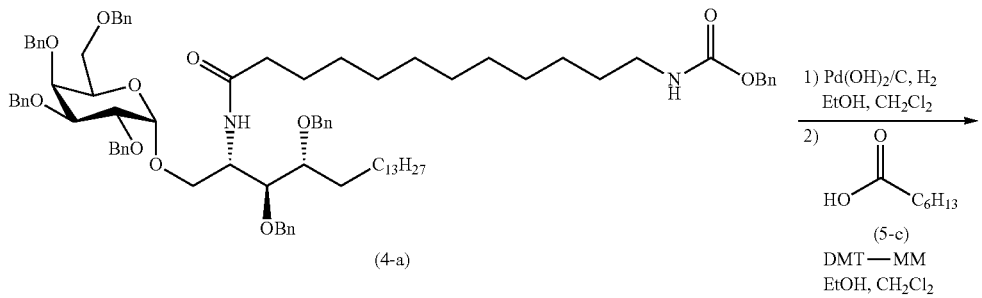

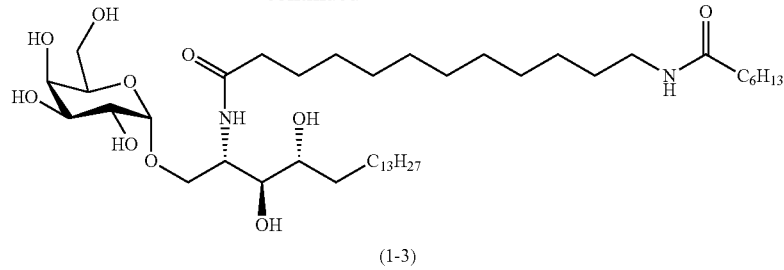

(1-3)

Synthesis Example 4

Synthesis of 12-(5-bromopentanamide)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)dodecanamide (Compound (1-4))

In the same manner as the synthesis method of compound (1-1) from compound (4-a) except that compound (5-d) was used instead of compound (5-a), compound (4-a) (15.0 mg, 0.011 mmol) was converted to compound (1-4) as a white solid (1.9 mg, 23% yield). Analysis results of NMR spectrum and reaction scheme are shown below.

$^1$H NMR (400 MHz, CDCl$_3$:CD$_3$OD=10:1) δ 0.81 (t, J=6.8 Hz, 3H), 1.17-1.25 (m, 40H), 1.39-1.43 (m, 2H), 1.51-1.55 (m, 2H), 1.68-1.73 (m, 2H), 1.79-1.83 (m, 2H), 2.13 (t, J=7.3 Hz, 4H), 3.12 (t, J=7.3 Hz, 2H), 3.35 (t, J=6.6 Hz, 2H), 3.41-3.47 (m, 2H), 3.59-3.67 (m, 3H), 3.69-3.75 (m, 3H), 3.82 (dd, J=10.7, 3.8 Hz, 1H), 3.88 (d, J=3.8 Hz, 1H), 4.11-4.12 (m, 1H), 4.84 (d, J=3.8 Hz, 1H); $^{13}$C NMR (100 MHz, CDCl$_3$:CD$_3$OD=10:1) δ 14.2, 22.8, 24.4, 25.9 (2C), 26.9, 29.3 (2C), 29.4 (3C), 29.5 (2C), 29.7, 29.8 (7C), 29.9, 32.0, 32.2, 32.8, 33.3, 35.5, 36.6, 39.6, 50.3, 62.1, 67.7, 68.9, 69.9, 70.3, 70.6, 72.2, 74.9, 99.7, 173.4, 174.5: HRMS (ESI-TOF) calcd C$_{41}$H$_{79}$BrN$_2$NaO$_{10}$: (M+Na)$^+$, 861.4810; found: (M+Na)$^+$, 861.4823.

Synthesis Example 5

Synthesis of 12-(7-bromoheptanamide)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)dodecanamide ((1-5))

In the same manner as the synthesis method of compound (1-1) from compound (4-a) except that compound (5-e) was used instead of compound (5-a), compound (4-a) (15.0 mg, 0.011 mmol) was converted to compound (1-5) as a white solid (2.0 mg, 23% yield). Analysis results of NMR spectrum and reaction scheme are shown below.

$^1$H NMR (400 MHz, CDCl$_3$:CD$_3$OD=10:1) δ 0.88 (t, J=6.8 Hz, 3H), 1.25-1.35 (m, 42H), 1.42-1.50 (m, 4H), 1.58-1.68 (m, 4H), 1.82-1.89 (m, 2H), 2.16 (t, J=7.0 Hz, 2H), 2.20 (t, J=7.0 Hz, 2H), 3.18-3.21 (m, 2H), 3.41 (t, J=6.8 Hz, 2H), 3.51-3.54 (m, 2H), 3.67-3.74 (m, 3H), 3.76-3.82 (m, 3H), 3.87-3.92 (m, 1H), 3.94-3.96 (m, 1H), 4.19 (d, J=4.9 Hz, 1H), 4.91 (d, J=3.9 Hz, 1H); $^{13}$C NMR (100 MHz, CDCl$_3$:CD$_3$OD=10:1) δ 14.2, 22.8, 25.7, 25.9 (2C), 26.9, 27.9, 28.4, 29.3 (2C), 29.4 (2C), 29.5 (2C), 29.7, 29.8 (8C), 29.9, 32.0, 32.6, 32.8, 33.9, 36.5, 36.6, 39.5, 50.3, 62.1, 67.7, 69.0, 69.9, 70.3, 70.7, 72.2, 74.9, 99.7, 174.0, 174.5: HRMS (ESI-TOF) calcd C$_{43}$H$_{83}$BrN$_2$NaO$_{10}$: (M+Na)$^+$, 889.5123; found: (M+Na)$^+$, 889.5128.

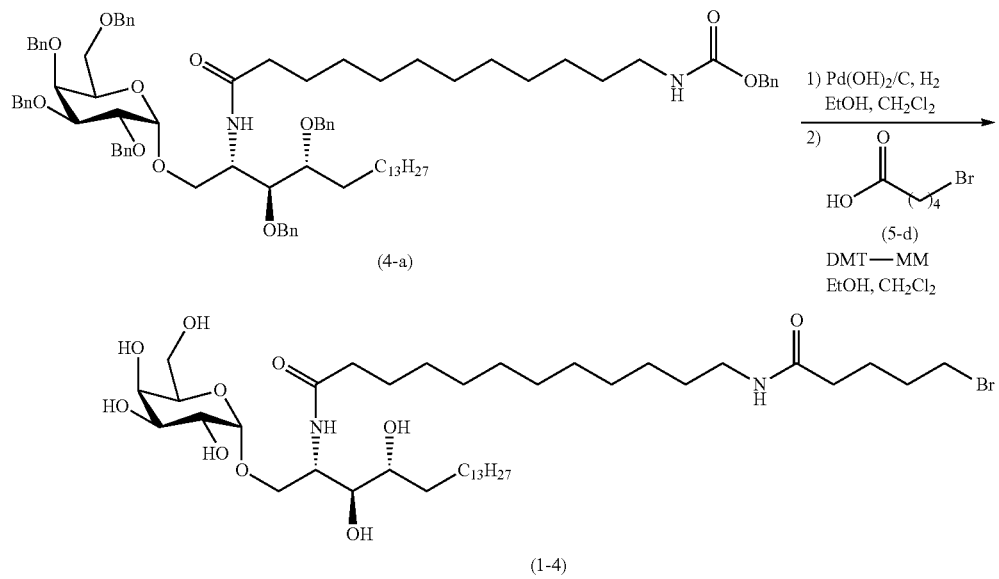

(1-4)

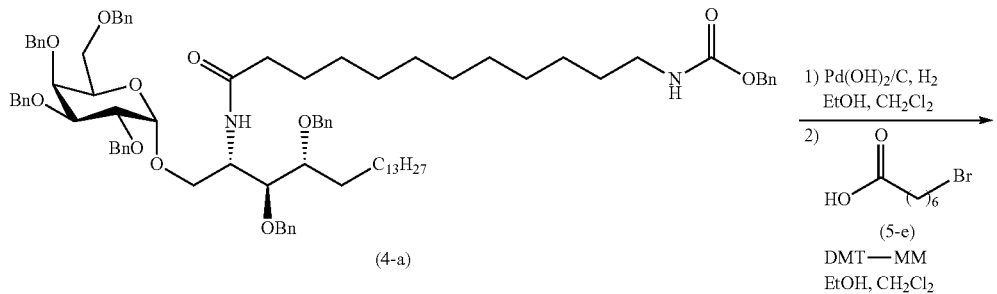

(4-a)

1) Pd(OH)$_2$/C, H$_2$
EtOH, CH$_2$Cl$_2$

2)

(5-e)

DMT—MM
EtOH, CH$_2$Cl$_2$

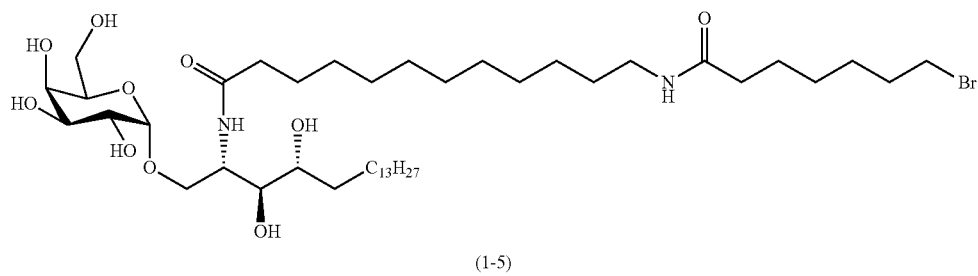

(1-5)

Synthesis Example 6

Synthesis of 12-(11-bromoundecanamide)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)dodecanamide (Compound (1-6))

In the same manner as the synthesis method of compound (1-1) from compound (4-a) except that compound (5-f) was used instead of compound (5-a), compound (4-a) (15.0 mg, 0.011 mmol) was converted to compound (1-6) as a white solid (2.0 mg, 22% yield). Analysis results of NMR spectrum and reaction scheme are shown below.

$^1$H NMR (400 MHz, CDCl$_3$:CD$_3$OD=10:1) 0.88 (t, J=6.8 Hz, 3H), 1.25-1.32 (m, 50H), 1.41-1.47 (m, 4H), 1.58-1.65 (m, 4H), 1.81-1.89 (m, 2H), 2.15 (t, J=7.7 Hz, 2H), 2.19 (t, J=7.7 Hz, 2H), 3.19 (t, J=7.3 Hz, 2H), 3.41 (t, J=7.0 Hz, 2H), 3.48-3.54 (m, 2H), 3.69-3.72 (m, 3H), 3.77-3.81 (m, 3H), 3.89 (dd, J=10.7, 3.8 Hz, 1H), 3.95 (d, J=3.8 Hz, 1H), 4.17-4.20 (m, 1H), 4.91 (d, J=3.8 Hz, 1H); $^{13}$C NMR (100 MHz, CDCl$_3$:CD$_3$OD=10:1) δ 14.2, 22.8, 25.9, 26.0 (2C), 26.9, 28.2, 28.8, 29.3 (2C), 29.4, 29.5 (6C), 29.7, 29.8 (9C), 29.9, 32.0, 32.8, 32.9, 34.2, 36.6, 36.8, 39.5, 50.3, 62.1, 67.7, 69.0, 69.9, 70.3, 71.9, 72.2, 74.9, 99.7, 174.2, 174.5: HRMS (ESI-TOF) calcd C$_{47}$H$_{91}$BrN$_2$NaO$_{10}$: (M+Na)$^+$, 945.5725; found: (M+Na)$^+$, 945.5734.

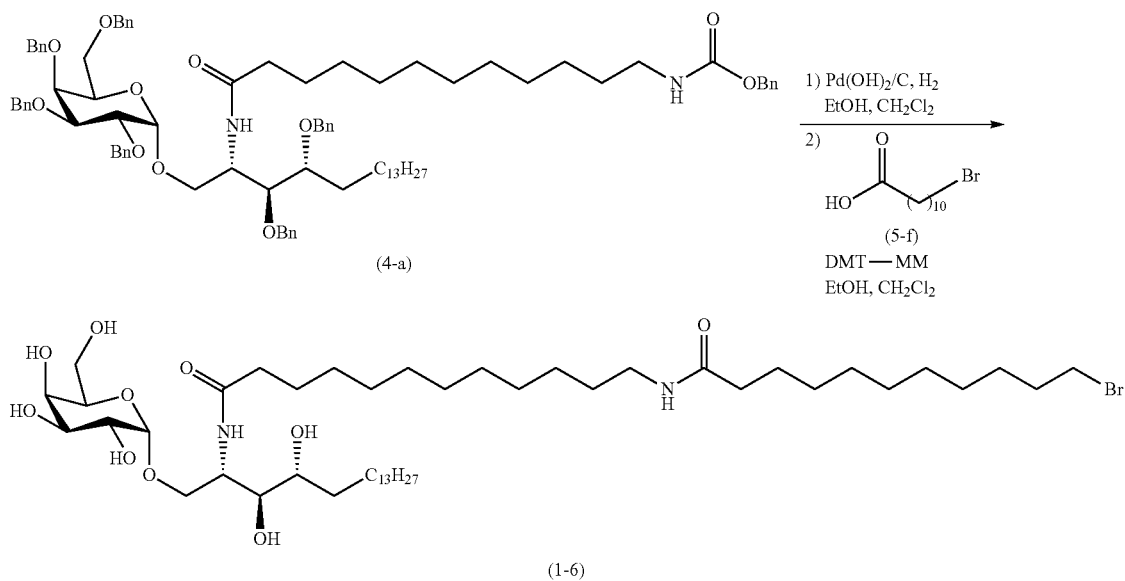

(4-a)

1) Pd(OH)$_2$/C, H$_2$
EtOH, CH$_2$Cl$_2$

2)

(5-f)

DMT—MM
EtOH, CH$_2$Cl$_2$ (1-6)

Synthesis Example 7

Synthesis of 12-bromo-N-(12-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-12-oxododecyl)dodecanamide (Compound (1-7))

In the same manner as the synthesis method of compound (1-1) from compound (4-a) except that compound (5-g) was used instead of compound (5-a), compound (4-a) (15.0 mg, 0.011 mmol) was converted to compound (1-7) as a white solid (6.8 mg, 72% yield). Analysis results of NMR spectrum and reaction scheme are shown below.

$^1$H NMR (400 MHz, CDCl$_3$:CD$_3$OD=10:1) δ 0.88 (t, J=6.6 Hz, 3H), 1.26-1.32 (m, 48H), 1.42-1.48 (m, 4H), 1.57-1.63 (m, 4H), 1.82-1.89 (m, 2H), 2.15 (t, J=7.8 Hz, 2H), 2.20 (t, J=7.8 Hz, 2H), 3.19 (t, J=7.3 Hz, 2H), 3.42 (t, J=6.8 Hz, 2H), 3.51-3.55 (m, 2H), 3.67-3.74 (m, 3H), 3.76-3.82 (m, 3H), 3.89 (dd, J=10.7, 3.8 Hz, 1H), 3.95 (d, J=3.8 Hz, 1H), 4.17-4.21 (m, 1H), 4.91 (d, J=3.8 Hz, 1H); $^{13}$C NMR (100 MHz, CDCl$_3$:CD$_3$OD=10:1) δ 14.2, 22.8, 25.9, 26.0 (2C), 26.9, 28.2, 28.8, 29.3 (2C), 29.4 (2C), 29.5 (8C), 29.7, 29.8 (7C), 29.9, 32.0, 32.7, 32.9, 34.2, 36.6, 36.8, 39.5, 50.4, 62.1, 67.7, 69.0, 69.9, 70.3, 70.7, 72.2, 74.9, 99.7, 174.2, 174.4: HRMS (ESI-TOF) calcd C$_{48}$H$_{93}$BrN$_2$NaO$_{10}$: (M+Na)$^+$, 959.5906; found: (M+Na)$^+$, 959.5907.

Synthesis Example 8

Synthesis of 5-(oxiran-2-yl)pentanoic acid (Compound (5-h))

To a stirred solution of compound (15) (256 mg, 2.0 mmol) in CH$_2$Cl$_2$ (16 mL) was added m-CPBA (689 mg, 4.0 mmol), and the obtained mixture was stirred at room temperature for 12 h. The obtained mixture was concentrated under reduced pressure, subjected to a flash chromatography over silica gel with n-hexane-EtOAc (1:5) to give compound (5-h) as a colorless oil (303 mg, 99% yield). Analysis results of NMR spectrum and reaction scheme are shown below.
H NMR (400 MHz, CDCl$_3$) δ 1.47-1.61 (m, 4H), 1.67-1.74 (m, 2H), 2.38 (t, J=7.3 Hz, 2H), 2.48 (dd, J=4.9, 2.9 Hz, 1H), 2.76 (dd, J=4.9, 3.8 Hz, 1H), 2.90-2.94 (m, 1H); $^{13}$C NMR (100 MHz, CDCl$_3$) δ 27.1, 28.1, 34.7, 36.5, 49.7, 54.8, 182.2.

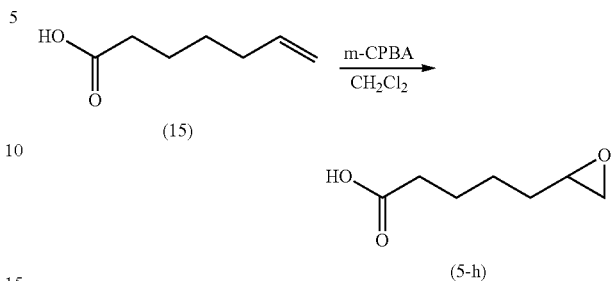

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-12-(5-(oxiran-2-yl)pentanamide)dodecanamide (Compound (1-8))

In the same manner as the synthesis method of compound (1-1) from compound (4-a) except that compound (5-h) was used instead of compound (5-a), compound (4-a) (15.0 mg, 0.011 mmol) was converted to compound (1-8) as a white solid (2.9 mg, 36% yield). Analysis results of NMR spectrum and reaction scheme are shown below.

$^1$H NMR (400 MHz, CDCl$_3$:CD$_3$OD=10:1) δ 0.88 (t, J=6.8 Hz, 3H), 1.25-1.30 (m, 40H), 1.46-1.52 (m, 4H), 1.55-1.69 (m, 6H), 2.18 (t, J=7.5 Hz, 2H), 2.20 (t, J=7.5 Hz, 2H), 2.50 (dd, J=4.8, 2.8 Hz, 1H), 2.78-2.79 (m, 1H), 2.93-2.95 (m, 1H), 3.16-3.21 (m, 2H), 3.50-3.56 (m, 2H), 3.67-3.74 (m, 3H), 3.77-3.81 (m, 3H), 3.89 (dd, J=10.7, 3.8 Hz, 1H), 3.95 (d, J=3.8 Hz, 1H), 4.18-4.19 (m, 1H), 4.91 (d, J=3.8 Hz, 1H); $^{13}$C NMR (100 MHz, CDCl$_3$:CD$_3$OD=10:1) δ 14.2, 22.8, 25.6 (2C), 25.9, 26.0, 27.0, 29.2, 29.4 (2C), 29.5 (4C), 29.8 (8C), 29.9, 32.0, 32.1, 32.8, 36.4, 36.6, 39.6, 47.4, 50.4, 52.6, 62.1, 67.7, 69.0, 69.9, 70.3, 70.7, 72.2, 74.9, 99.8, 173.9, 174.5: HRMS (ESI-TOF) calcd C$_{43}$H$_{82}$N$_2$NaO$_{11}$: (M+Na)$^+$, 825.5811; found: (M+Na)$^+$, 825.5824.

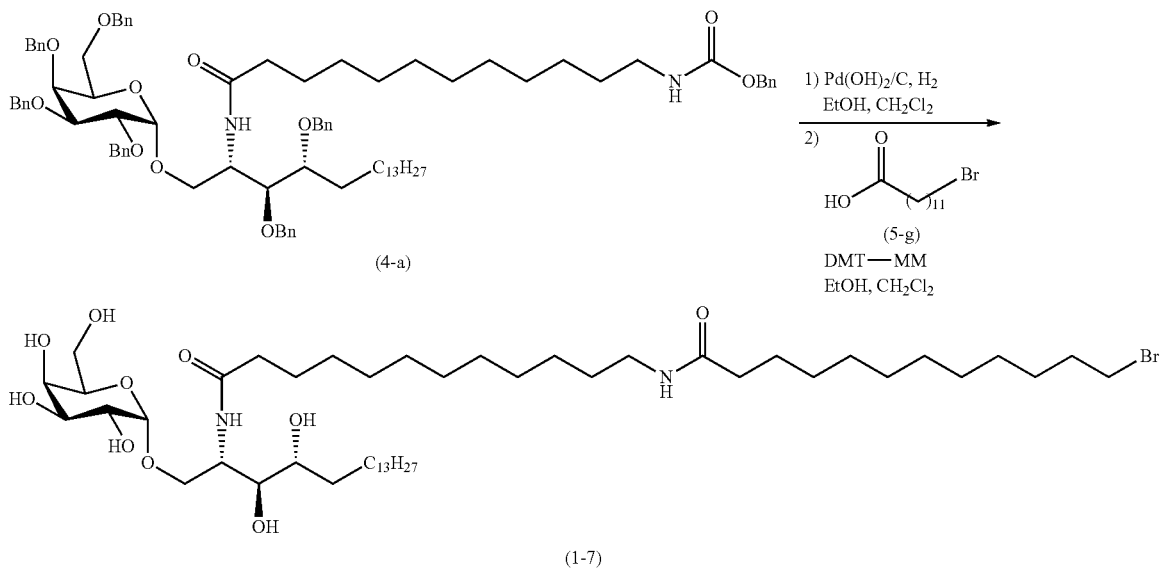

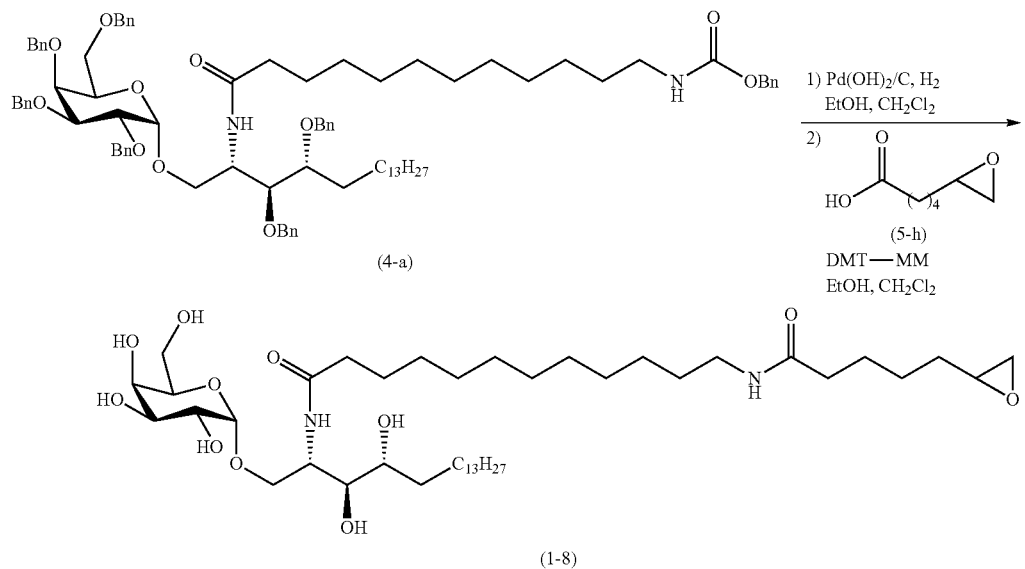

Synthesis Example 9

Synthesis of 8-acrylamideoctanoic acid (Compound (5-i))

To a stirred solution of compound (14-b) (300 mg, 1.88 mmol) in $CH_2Cl_2$ (1.5 mL) and $H_2O$ (1.5 mL) were added NaOH (188 mg, 4.7 mmol) and acryloyl chloride (0.18 mL, 2.26 mmol), and the obtained mixture was stirred at room temperature for 7.5 hr and diluted with saturated $KHSO_4$ aqueous solution. The whole mixture was extracted with EtOAc. The extract was washed with saturated $KHSO_4$ aqueous solution and dried over $MgSO_4$, and concentrated under reduced pressure followed by recrystallization from hexane/EtOAc (5/1) to give compound (5-i) as a white solid (327 mg, 82% yield). Analysis results of NMR spectrum and reaction scheme are shown below.

$^1$H NMR (400 MHz, $CDCl_3$) δ 1.32-1.38 (m, 6H), 1.51-1.57 (m, 2H), 1.60-1.67 (m, 2H), 2.35 (t, J=7.4 Hz, 2H), 3.33 (td, J=7.2, 6.1 Hz, 2H), 5.61-5.64 (m, 1H), 5.64 (d, J=10.3 Hz, 1H), 6.08 (dd, J=16.9, 10.3 Hz, 1H), 6.28 (d, J=16.9 Hz, 1H).

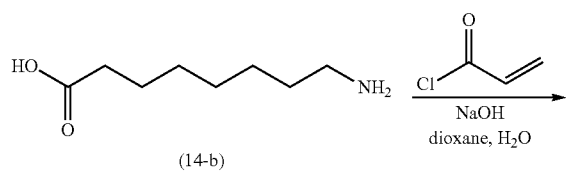

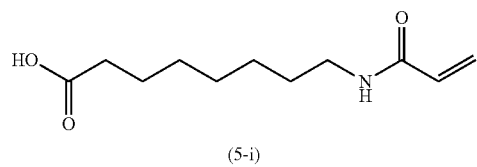

Synthesis of 12-(8-acrylamideoctanamide)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)dodecanamide (Compound (1-9))

In the same manner as the synthesis method of compound (1-1) from compound (4-a) except that compound (5-i) was used instead of compound (5-a), compound (4-a) (15.0 mg, 0.011 mmol) was converted to compound (1-9) as a white solid (3.3 mg, 38% yield). Analysis results of NMR spectrum and reaction scheme are shown below.

$^1$H NMR (400 MHz, $CDCl_3$:$CD_3OD$=10:1) δ 0.88 (t, J=6.8 Hz, 3H), 1.25-1.33 (m, 46H), 1.47-1.53 (m, 4H), 1.58-1.67 (m, 4H), 2.15 (t, J=7.7 Hz, 2H), 2.19 (t, J=7.7 Hz, 2H), 3.19 (t, J=7.1 Hz, 2H), 3.27 (t, J=7.1 Hz, 2H), 3.51-3.54 (m, 2H), 3.68-3.73 (m, 3H), 3.77-3.81 (m, 3H), 3.87-3.92 (m, 1H), 3.95 (d, J=4.0 Hz, 1H), 4.19-4.20 (m, 1H), 4.91 (d, J=4.0 Hz, 1H), 5.63 (dd, J=10.0, 1.7 Hz, 1H), 6.15 (dd, J=17.1, 10.0 Hz, 1H), 6.25 (dd, J=17.1, 1.7 Hz, 1H); $^{13}$C NMR (100 MHz, $CDCl_3$:$CD_3OD$=10:1) δ 14.2, 22.8, 25.6, 25.9, 26.0, 26.5, 26.9, 28.6, 28.8, 29.1, 29.2, 29.3 (2C), 29.5 (2C), 29.7, 29.8 (9C), 29.9, 32.0 (2C), 32.8, 36.4, 36.6, 39.4, 39.5, 50.3, 62.1, 67.7, 69.0, 69.9, 70.3, 70.7, 72.2, 75.0, 99.8, 126.3, 130.8, 166.6, 174.4 (2C): HRMS (ESI-TOF) calcd $C_{48}H_{90}N_3O_{13}$: $(M+HCO_2)^-$, 916.6479; found: $(M+HCO_2)^-$, 916.6484.

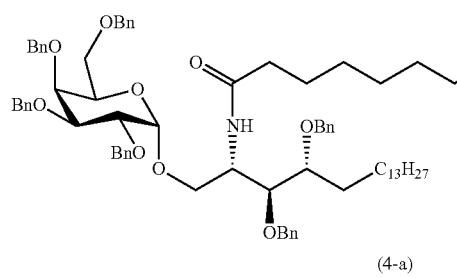
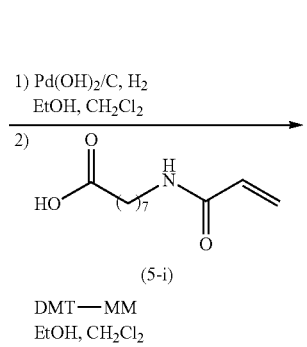

(4-a)　　(5-i)

DMT—MM
EtOH, CH₂Cl₂

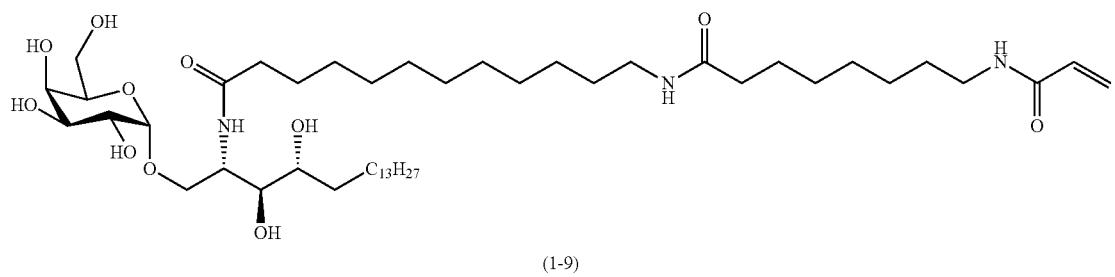

(1-9)

Synthesis Example 10

Synthesis of 7-acrylamideheptanoic acid (Compound 5-j)

In the same manner as the synthesis method of compound (5-i) from compound (14-b) except that compound (14-c) was used instead of compound (14-b), compound (4-c) (300 mg, 2.1 mmol) was converted to compound (5-j) as a white solid (58.3 mg, 14% yield). Analysis results of NMR spectrum and reaction scheme are shown below.

$^1$H NMR (400 MHz, CDCl$_3$) δ 1.35-1.39 (m, 4H), 1.52-1.59 (m, 2H), 1.61-1.68 (m, 2H), 2.36 (t, J=7.4 Hz, 2H), 3.34 (td, J=7.4, 6.0 Hz, 2H), 5.63-5.65 (m, 1H), 5.64 (d, J=10.3 Hz, 1H), 6.08 (dd, J=17.1, 10.3 Hz, 1H), 6.28 (d, J=17.1 Hz, 1H).

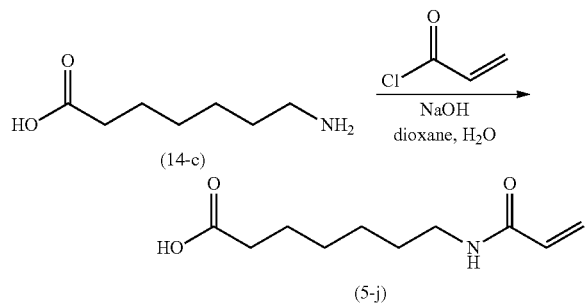

Synthesis of 12-(7-acrylamideheptanamide)-N-((2S, 3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)dodecanamide (Compound (1-10))

In the same manner as the synthesis method of compound (1-1) from compound (4-a) except that compound (5-j) was used instead of compound (5-a), compound (4-a) (15.0 mg, 0.011 mmol) was converted to compound (1-10) as a white solid (5.0 mg, 58% yield). Analysis results of NMR spectrum and reaction scheme are shown below.

$^1$H NMR (400 MHz, CDCl$_3$:CD$_3$OD=10:1) δ 0.88 (t, J=6.8 Hz, 3H), 1.25-1.35 (m, 39H), 1.47-1.55 (m, 4H), 1.57-1.63 (m, 4H), 2.16 (t, J=7.6 Hz, 2H), 2.20 (t, J=7.6 Hz, 2H), 3.16-3.21 (m, 2H), 3.25-3.29 (m, 2H), 3.51-3.54 (m, 2H), 3.67-3.74 (m, 3H), 3.76-3.82 (m, 3H), 3.89 (dd, J=10.7, 3.8 Hz, 1H), 3.96 (d, J=3.8 Hz, 1H), 4.19-4.20 (m, 1H), 4.91 (d, J=3.8 Hz, 1H), 5.64 (dd, J=10.1, 1.8 Hz, 1H), 6.15 (dd, J=17.1, 10.1 Hz, 1H), 6.25 (dd, J=17.1, 1.8 Hz, 1H); $^{13}$C NMR (100 MHz, CDCl$_3$:CD$_3$OD=10:1) δ 14.2, 22.8, 25.6, 25.9, 26.0, 26.3, 26.9, 28.5, 28.9, 29.2, 29.3 (2C), 29.4 (2C), 29.5 (2C), 29.7, 29.8 (6C), 29.9, 32.0 (2C), 32.8, 36.3, 36.6, 39.3, 39.5, 50.4, 62.1, 67.7, 69.0, 69.9, 70.3, 70.7, 72.2, 74.9, 99.8, 126.3, 130.8, 166.6, 174.4 (2C): HRMS (ESI-TOF) calcd C$_{46}$H$_{87}$N$_3$NaO$_{11}$: (M+Na)$^+$, 880.6233; found: (M+Na)$^+$, 880.6246.

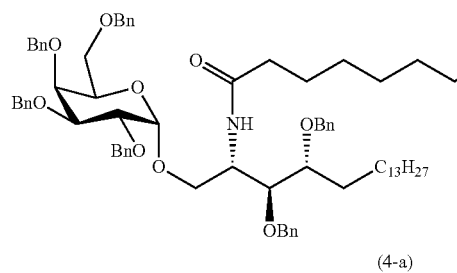

(4-a)

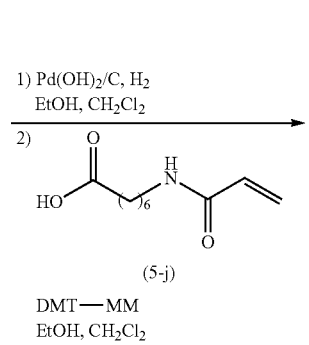

(5-j)

DMT—MM
EtOH, CH$_2$Cl$_2$

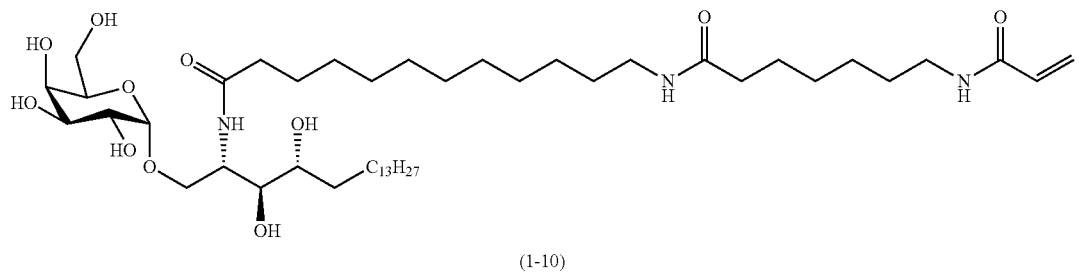

(1-10)

Synthesis Example 11

Synthesis of 7-propionamideheptanoic acid (Compound (5-k))

In the same manner as the synthesis method of compound (5-i) from compound (14-b) except that compound (14-c) was used instead of compound (14-b), compound (14-c) (300 mg, 2.10 mmol) was converted to compound (5-k) as a white solid (236 mg, 56% yield). Analysis results of NMR spectrum and reaction scheme are shown below.

$^1$H NMR (400 MHz, CDCl$_3$) δ 1.15 (t, J=7.5 Hz, 3H), 1.33-1.38 (m, 4H), 1.48-1.54 (m, 2H), 1.61-1.67 (m, 2H), 2.22 (q, J=7.4 Hz, 2H), 2.34 (t, J=7.4 Hz, 2H), 3.24 (td, J=7.4, 7.4 Hz, 2H), 5.67-5.70 (m, 1H); $^{13}$C NMR (100 MHz, CDCl$_3$) δ 9.9, 24.6, 26.4, 28.6, 29.3, 29.7, 33.9, 39.4, 174.2, 178.7; HRMS (ESI-TOF) calcd C$_{10}$H$_{18}$NO$_3$:(M−H)$^-$, 200.1292; found: (M−H)$^-$, 200.1299.

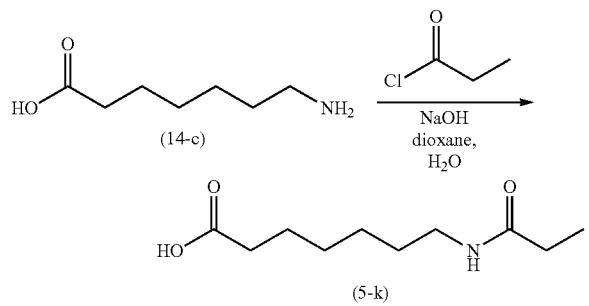

Synthesis of N-((2S,3S,4R)-3,4-dihydroxy-1-(((2S, 3R,4S,5R,6R)-3,4,5-trihydroxy-6-(hydroxymethyl) tetrahydro-2H-pyran-2-yl)oxy)octadecan-2-yl)-12- (7-propionamideheptanamide)dodecanamide (Compound (1-11))

In the same manner as the synthesis method of compound (1-1) from compound (4-a) except that compound (5-k) was used instead of compound (5-a), compound (4-a) (10.0 mg, 0.0067 mmol) was converted to compound (1-11) as a white solid (2.4 mg, 42% yield). Analysis results of NMR spectrum and reaction scheme are shown below.

$^1$H NMR (400 MHz, CDCl$_3$:CD$_3$OD=10:1) 0.92 (t, J=7.6 Hz, 3H), 1.14 (t, J=7.6 Hz, 3H), 1.25-1.32 (m, 44H), 1.45-1.51 (m, 4H), 1.60-1.68 (m, 4H), 2.14-2.23 (m, 6H), 3.16-3.22 (m, 4H), 3.48-3.53 (m, 2H), 3.69-3.73 (m, 3H), 3.76-3.82 (m, 3H), 3.89 (dd, J=10.0, 3.8 Hz, 1H), 3.95 (d, J=3.8 Hz, 1H), 4.18-4.21 (m, 1H), 4.91 (d, J=3.8 Hz, 1H); $^{13}$C NMR (100 MHz, CDCl$_3$:CD$_3$OD=10:1) δ 13.9 (2C), 22.5, 22.8, 23.6, 25.3, 25.6, 25.7, 26.0, 26.6, 28.3, 28.8 (2C), 28.9, 29.0 (2C), 29.2 (2C), 29.4, 29.6 (5C), 30.2, 31.8 (2C), 32.7, 36.1, 36.3, 38.6, 39.0, 39.3, 50.1, 61.9, 68.1, 68.8, 69.7, 70.1, 70.4, 72.0, 74.8, 99.5, 174.0, 174.9 (2C): HRMS (ESI-TOF) calcd C$_{46}$H$_{89}$N$_3$NaO$_{11}$: (M+Na)$^+$, 882.6389; found: (M+Na)$^+$, 882.6400.

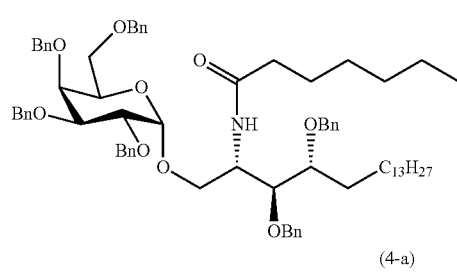

(4-a)

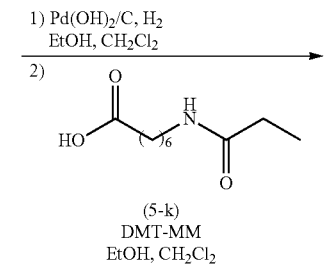

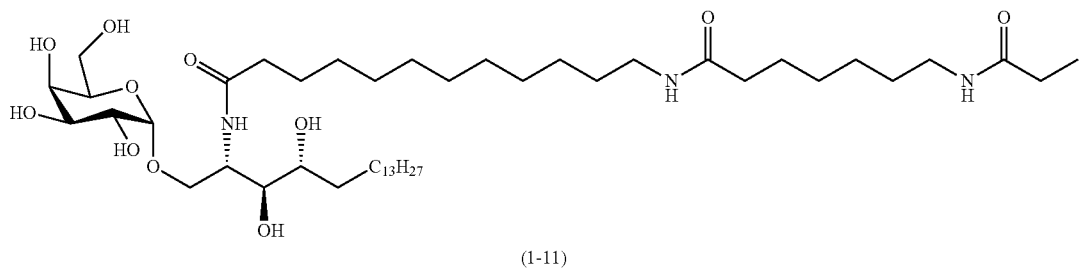

(1-11)

Synthesis Example 12

Synthesis of 8-propionamideoctanoic acid (Compound (5-l))

In the same manner as the synthesis method of compound (5-i) from compound (14-b) except that propionyl chloride was used instead of acryloyl chloride, compound (14-b) (300 mg, 1.88 mmol) was converted to compound (5-l) as a white solid (292 mg, 72% yield). Analysis results of NMR spectrum and reaction scheme are shown below.

$^1$H NMR (400 MHz, CDCl$_3$) δ 1.16 (t, J=7.6 Hz, 3H), 1.29-1.36 (m, 6H), 1.46-1.52 (m, 2H), 1.60-1.66 (m, 2H), 2.22 (q, J=7.6 Hz, 2H), 2.34 (t, J=7.2 Hz, 2H), 3.24 (td, J=6.7, 6.7 Hz, 2H), 5.66-5.70 (m, 1H); $^{13}$C NMR (100 MHz, CDCl$_3$) δ 9.9, 24.6, 26.6, 28.8, 28.9, 29.5, 29.7, 34.0, 39.5, 174.2, 178.8: HRMS(ESI-TOF) calcd C$_{11}$H$_{20}$NO$_3$: (M−H)$^-$, 214.1449; found: (M−H)$^-$, 214.1452.

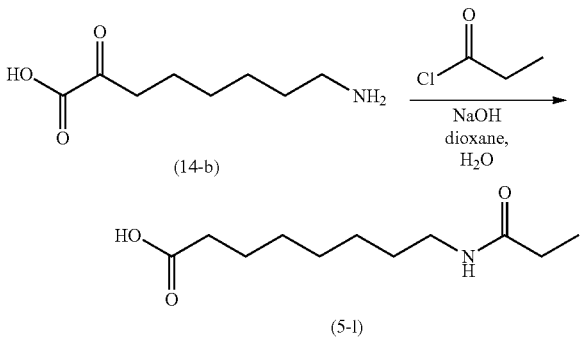

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-12-(8-propionamideoctanamide)dodecanamide (Compound (1-12))

In the same manner as the synthesis method of compound (1-1) from compound (4-a) except that compound (5-1) was used instead of compound (5-a), compound (4-a) (10.0 mg, 0.0067 mmol) was converted to compound (1-12) as a white solid (2.1 mg, 36% yield). Analysis results of NMR spectrum and reaction scheme are shown below.

$^1$H NMR (400 MHz, CDCl$_3$:CD$_3$OD=10:1) δ 0.88 (t, J=6.8 Hz, 3H), 1.14 (t, J=7.7 Hz, 3H), 1.25-1.31 (m, 46H), 1.47-1.49 (m, 4H), 1.59-1.61 (m, 4H), 2.16-2.20 (m, 6H), 3.18-3.21 (m, 4H), 3.48-3.54 (m, 2H), 3.67-3.74 (m, 3H), 3.76-3.82 (m, 3H), 3.89 (dd, J=10.5, 3.8 Hz, 1H), 3.95 (d, J=3.8 Hz, 1H), 4.18-4.21 (m, 1H), 4.91 (d, J=3.8 Hz, 1H): $^{13}$C NMR (100 MHz, CDCl$_3$:CD$_3$OD=10:1) 13.2 (2C), 22.7 (2C), 25.5, 25.6, 25.8, 25.9, 26.4, 26.8, 28.6, 28.8, 29.2 (2C), 29.3, 29.4 (2C), 29.7 (2C), 29.6 (8C), 32.0 (2C), 32.9, 36.5, 36.6, 39.3, 39.5, 50.3, 62.1, 67.7, 69.0, 69.9, 70.3, 70.6, 72.2, 75.0, 99.7, 174.2, 174.4, 175.0; HRMS (ESI-TOF) calcd C$_{47}$H$_{91}$N$_3$NaO$_{11}$: (M+Na)$^+$, 896.6546; found:(M+Na)$^+$, 896.6559.

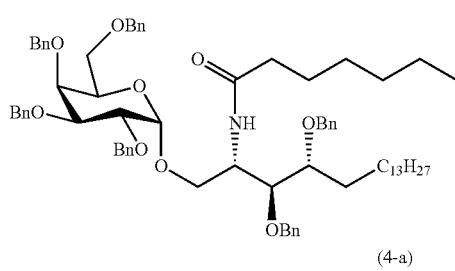

(4-a)

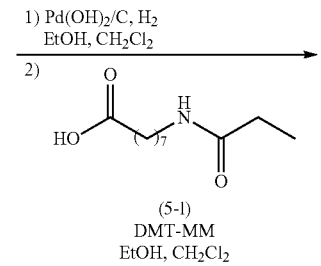

(5-l)
DMT-MM
EtOH, CH$_2$Cl$_2$

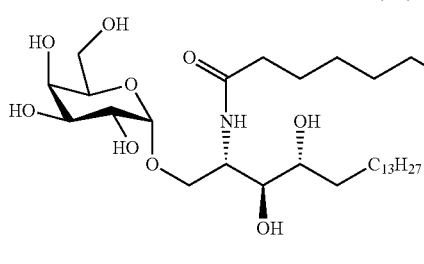

(1-12)

Synthesis Example 13

Synthesis of 8-(((benzyloxy)carbonyl)amino)octanoic acid (Compound (3-b))

In the same manner as the synthesis method of compound (3-a) from compound (14-a) except that compound (14-b) was used instead of compound (14-a), compound (14-b) (300 mg, 1.49 mmol) was converted to compound (3-b) as a colorless oil (351 mg, 63% yield. The reaction scheme is shown below.

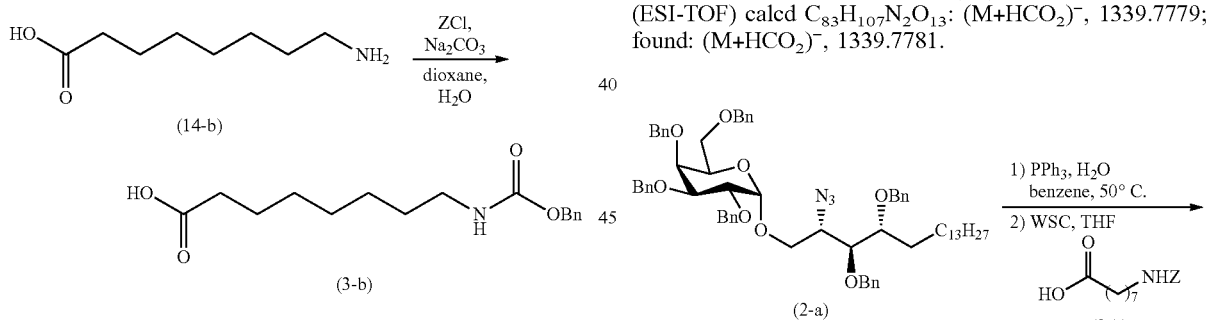

Synthesis of benzyl (8-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)amino)-8-oxooctyl)carbamate (Compound (4-b))

In the same manner as the synthesis method of compound (4-a) from compound (2-a) and compound (3-a) except that compound (3-b) was used instead of compound (3-a), compound (2-a) (20 mg, 0.019 mmol) was converted to compound (4-b) as a colorless oil (16.1 mg, 65% yield). Analysis results of NMR spectrum and reaction scheme are shown below.

$^1$H NMR (400 MHz, CDCl$_3$) δ 0.88 (t, J=6.8 Hz, 3H), 1.20-1.28 (m, 30H), 1.40-1.51 (m, 6H), 1.88-1.95 (m, 2H), 3.10-3.16 (m, 2H), 3.41 (dd, J=10.9, 6.4 Hz, 1H), 3.46-3.52 (m, 2H), 3.73 (dd, J=10.9, 3.7 Hz, 1H), 3.85 (dd, J=6.4, 2.6 Hz, 1H), 3.87-3.94 (m, 3H), 3.98-4.02 (m, 1H), 4.04 (dd, J=10.9, 3.7 Hz, 1H), 4.13-4.20 (m, 1H), 4.36 (d, J=11.7 Hz, 1H), 4.42 (d, J=11.7 Hz, 1H), 4.46 (d, J=11.7 Hz, 1H), 4.51 (d, J=11.7 Hz, 1H), 4.53-4.60 (m, 2H), 4.64 (d, J=11.7 Hz, 1H), 4.65-4.72 (m, 1H), 4.70-4.81 (m, 4H), 4.84 (d, J=3.6 Hz, 1H), 4.91 (d, J=11.7 Hz, 1H), 5.08 (s, 2H), 6.18 (d, J=8.8 Hz, 1H), 7.37-7.21 (35H, m); $^{13}$C NMR (100 MHz, CDCl$_3$) δ 14.1, 22.7, 25.4, 26.5, 29.0, 29.1, 29.3, 29.6, 29.7 (9C), 29.8, 31.9, 36.4, 41.0, 50.2, 66.5, 69.2 (2C), 69.9, 71.6, 72.8, 73.5 (3C), 74.7 (2C), 76.6, 78.6, 78.8, 80.1, 99.5, 127.4 (2C), 127.5 (3C), 127.6, 127.7, 127.8 (8C), 127.9 (2C), 128.0, 128.1, 128.2 (2C), 128.3 (8C), 128.4 (4C), 128.5 (2C), 136.6, 137.5, 138.3, 138.4, 138.6 (3C), 156.3, 172.6; HRMS (ESI-TOF) calcd C$_{83}$H$_{107}$N$_2$O$_{13}$: (M+HCO$_2$)$^-$, 1339.7779; found: (M+HCO$_2$)$^-$, 1339.7781.

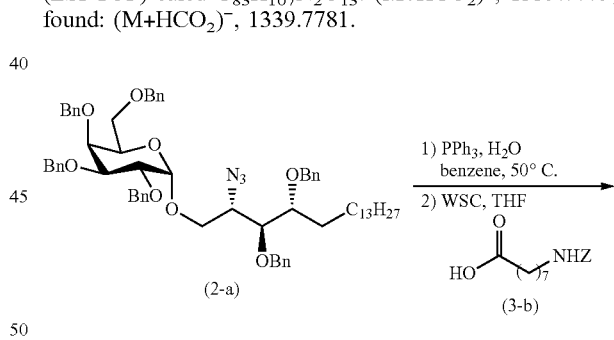

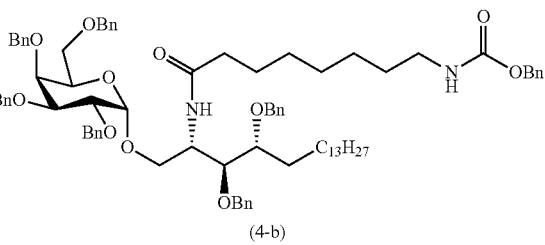

Synthesis of N-(8-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-8-oxooctyl)heptadecanamide (Compound (1-13))

In the same manner as the synthesis method of compound (1-1) from compound (4-a) except that compound (4-b) was used instead of compound (4-a) and compound (5-m) was used instead of compound (5-a), compound (4-b) (13.3 mg, 0.010 mmol) was converted to compound (1-13) as a white solid (1.8 mg, 21% yield). Analysis results of NMR spectrum and reaction scheme are shown below.

$^1$H NMR (400 MHz, CDCl$_3$:CD$_3$OD=10:1) δ 0.88 (t, J=6.8 Hz, 6H), 1.25-1.31 (m, 56H), 1.45-1.50 (m, 2H), 1.58-1.66 (m, 6H), 2.15 (t, J=7.7 Hz, 2H), 2.20 (t, J=7.7 Hz, 2H), 3.16-3.21 (m, 2H), 3.51-3.57 (m, 2H), 3.68-3.75 (m, 3H), 3.76-3.82 (m, 3H), 3.90 (dd, J=10.5, 3.6 Hz, 1H), 3.95 (d, J=3.6 Hz, 1H), 4.19-4.20 (m, 1H), 4.92 (d, J=3.6 Hz, 1H); $^{13}$C NMR (100 MHz, CDCl$_3$:CD$_3$OD=10:1) δ 13.9 (2C), 22.5, 25.4, 25.7, 25.8, 26.3, 28.4, 28.6, 29.1, 29.2 (3C), 29.4, 29.5, 29.6 (16C), 29.9, 31.8, 32.7, 36.1, 36.5, 39.2, 50.2, 61.8, 67.3, 68.8, 69.6, 70.1, 70.5, 72.0, 74.7, 99.5, 174.2 (2C); HRMS (ESI-TOF) calcd C$_{49}$H$_{96}$N$_2$NaO$_{10}$: (M+Na)$^+$, 895.6957; found:(M+Na)$^+$, 895.6955.

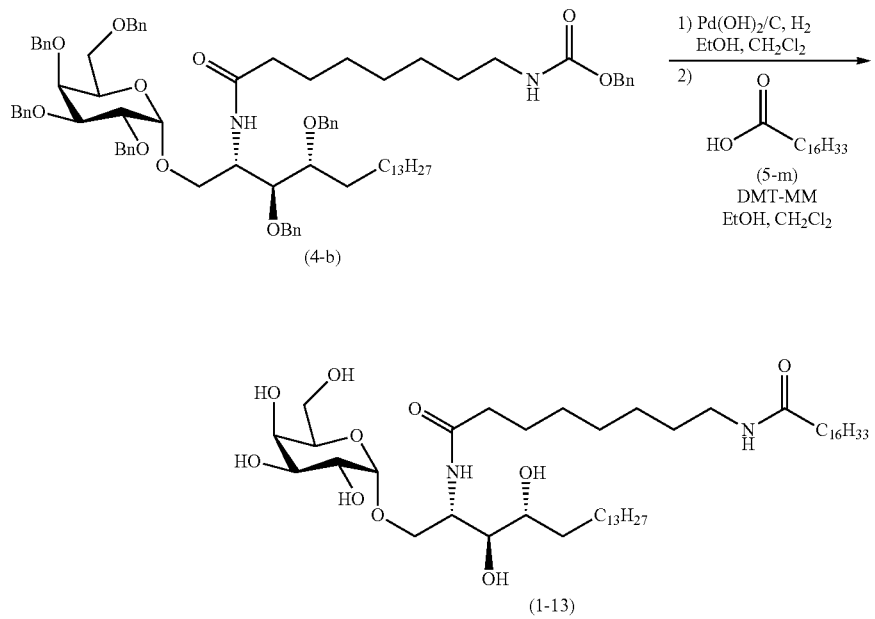

Synthesis Example 14

Synthesis of N-(8-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-8-oxooctyl)undecanamide (Compound (1-14))

In the same manner as the synthesis method of compound (1-1) from compound (4-a) except that compound (4-b) was used instead of compound (4-a) and compound (5-n) was used instead of compound (5-a), compound (4-b) (20.0 mg, 0.015 mmol) was converted to compound (1-14) as a white solid (4.4 mg, 37% yield). Analysis results of NMR spectrum and reaction scheme are shown below.

$^1$H NMR (400 MHz, CDCl$_3$:CD$_3$OD=10:1) δ 0.88 (t, J=6.7 Hz, 6H), 1.25-1.31 (m, 44H), 1.46-1.49 (m, 2H), 1.57-1.63 (m, 6H), 2.15 (t, J=7.7 Hz, 2H), 2.20 (t, J=7.7 Hz, 2H), 3.18 (t, J=7.7 Hz, 2H), 3.49-3.54 (m, 2H), 3.68-3.72 (m, 3H), 3.75-3.81 (m, 3H), 3.89 (dd, J=10.0, 3.8 Hz, 1H), 3.95 (d, J=3.8 Hz, 1H), 4.19 (d, J=3.8 Hz, 1H), 4.91 (d, J=3.8 Hz, 1H); $^{13}$C NMR (100 MHz, CDCl$_3$:CD$_3$OD=10:1) δ 14.0 (2C), 22.5, 22.6, 25.5, 25.8, 26.5, 28.3, 28.7, 28.8 (2C), 29.2 (2C), 29.3, 29.4, 29.6 (8C), 29.7 (2C), 31.7, 31.8, 32.7, 36.3, 36.6, 39.2, 50.2, 61.8, 67.6, 68.8, 69.7, 70.1, 70.5, 72.0, 74.5, 99.5, 174.1, 174.2: HRMS (ESI-TOF) calcd C$_{43}$H$_4$N$_2$NaO$_{10}$: (M+Na)$^+$, 811.6018; found: (M+Na)$^+$, 811.6026.

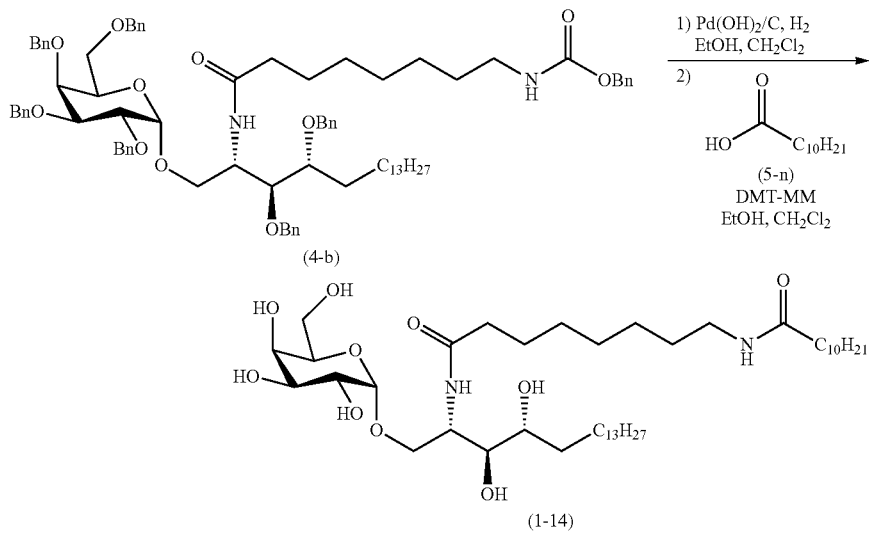

Synthesis Example 15

Synthesis of 9-(((benzyloxy)carbonyl)amino)nonanoic acid (Compound (3-c))

The preparation of 9-aminononanoic acid was carried out according to the method of Meijler, M. M. (J. Am. Chem. Soc. 2009, 131, 10610-10619). A solution of compound (16-a) (300 mg, 1.27 mmol) in 28% NH$_4$OH was stirred at 50° C. for 46 h. The obtained mixture was concentrated under reduced pressure to give a crude amine as a white solid, which was used without further purification. To a stirred suspension of this amine in dioxane (2.5 mL) and H$_2$O (2.5 mL) were added Na$_2$CO$_3$ (1.35 g, 12.7 mmol) and ZCl (0.90 mL, 6.36 mmol) at room temperature. After stirring for 25 hr at this temperature, the obtained mixture was diluted with EtOAc, washed with saturated KHSO$_4$ aqueous solution, and dried over Mg$_2$SO$_4$. Concentration under reduced pressure followed by recrystallization from hexane/EtOAc (8/1) gave compound (3-c) as a white solid (181 mg, 46% yield). Analysis results of NMR spectrum and reaction scheme are shown below.

$^1$H NMR (400 MHz, CDCl$_3$) δ 1.27-1.34 (m, 8H), 1.45-1.52 (m, 2H), 1.60-1.66 (m, 2H), 2.34 (t, J=7.3 Hz, 2H), 3.16-3.21 (m, 2H), 4.71-4.77 (m, 1H), 5.09-5.11 (m, 2H), 7.30-7.38 (m, 51H).

Synthesis of benzyl (9-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)amino)-9-oxononyl)carbamate (Compound (4-c))

In the same manner as the synthesis method of compound (4-a) from compound (2-a) and compound (3-a) except that compound (3-c) was used instead of compound (3-a), compound (2-a) (100 mg, 0.096 mmol) was converted to compound (4-c) as a colorless oil (117 mg, 93% yield). Analysis results of NMR spectrum and reaction scheme are shown below.

$^1$H NMR (400 MHz, CDCl$_3$) δ 0.88 (t, J=6.5 Hz, 3H), 1.16-1.30 (m, 32H), 1.42-1.50 (m, 4H), 1.56-1.70 (m, 2H), 1.87-1.98 (m, 2H), 3.11-3.18 (m, 2H), 3.41 (dd, J=10.2, 6.4 Hz, 1H), 3.46-3.52 (m, 2H), 3.73 (dd, J=10.2, 3.8 Hz, 1H), 3.83-3.95 (m, 4H), 3.99-4.07 (m, 2H), 4.13-4.19 (m, 1H), 4.36 (d, J=11.7 Hz, 1H), 4.42 (d, J=11.7 Hz, 1H), 4.46 (d, J=11.7 Hz, 1H), 4.51 (d, J=11.7 Hz, 11H), 4.54-4.60 (m, 2H), 4.64 (d, J=11.7 Hz, 1H), 4.70-4.72 (m, 1H), 4.73-4.82 (m, 4H), 4.85 (d, J=3.4 Hz, 1H), 4.92 (d, J=11.7 Hz, 1H), 5.07-5.11 (m, 2H), 6.19 (d, J=8.5 Hz, 1H), 7.43-7.15 (m, 35H); $^{13}$C NMR (100 MHz, CDCl$_3$) δ 14.1, 22.7, 25.6, 26.7, 29.0, 29.1, 29.3 (2C), 29.4, 29.7 (9C), 29.9, 31.9, 36.5, 41.0, 50.3, 66.6, 69.3, 69.4, 69.9, 71.7, 72.9, 73.5, 73.6 (2C), 74.7 (2C), 76.6, 78.6, 78.9, 80.1, 99.6, 127.4 (2C), 127.5 (2C), 127.6, 127.7 (2C), 127.8 (2C), 127.9 (8C), 128.1 (2C), 128.3 (8C), 128.4 (6C), 128.5 (2C), 136.6, 137.6, 138.4 (2C), 138.6, 138.7 (2C), 156.4, 172.8; HRMS (ESI-TOF) calcd C$_{83}$H$_{108}$N$_2$NaO$_{11}$: (M+Na)$^+$, 1331.7845; found:(M+Na)$^+$, 1331.7838.

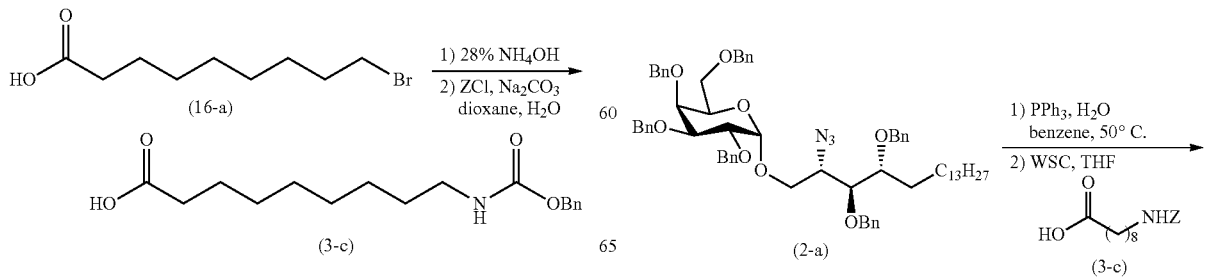

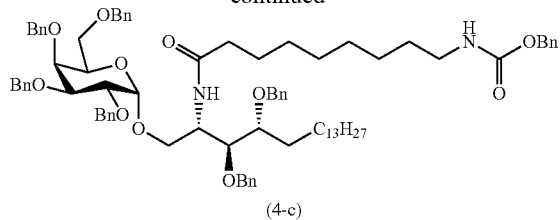

(4-c)

Synthesis of N-(9-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-9-oxononyl)decanamide (Compound (1-15))

In the same manner as the synthesis method of compound (1-1) from compound (4-a) except that compound (4-c) was used instead of compound (4-a) and compound (5-o) was used instead of compound (5-a), compound (4-c) (17.0 mg, 0.013 mmol) was converted to compound (1-15) as a white solid (2.1 mg, 20% yield). Analysis results of NMR spectrum and reaction scheme are shown below.

$^1$H NMR (400 MHz, CDCl$_3$:CD$_3$OD=10:1) δ 0.88 (t, J=6.7 Hz, 6H), 1.26-1.31 (m, 44H), 1.47-1.50 (m, 2H), 1.57-1.64 (m, 6H), 2.16 (t, J=8.2 Hz, 2H), 2.20 (t, J=8.2 Hz, 2H), 3.16-3.20 (m, 2H), 3.52-3.57 (m, 2H), 3.68-3.74 (m, 3H), 3.78-3.88 (m, 4H), 3.93-3.96 (m, 1H), 4.18-4.21 (m, 1H), 4.91 (d, J=3.8 Hz, 1H); $^{13}$C NMR (100 MHz, CDCl$_3$:CD$_3$OD=10:1) δ 14.0 (2C), 22.5, 22.6, 25.5, 25.8, 26.5, 28.3, 28.7, 28.8 (2C), 29.2 (2C), 29.3, 29.4, 29.6 (8C), 29.7 (2C), 31.7, 31.8, 32.7, 36.3, 36.6, 39.2, 50.2, 61.8, 67.6, 68.8, 69.7, 70.1, 70.5, 72.0, 74.5, 99.5, 174.1, 174.2: HRMS (ESI-TOF) calcd C$_{43}$H$_{84}$N$_2$NaO$_{10}$: (M+Na)$^+$, 811.6018; found: (M+Na)$^+$, 811.6017.

Synthesis Example 16

Synthesis of N-(9-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-9-oxononyl)palmitamide (Compound (1-16))

In the same manner as the synthesis method of compound (1-1) from compound (4-a) except that compound (4-c) was used instead of compound (4-a) and compound (5-p) was used instead of compound (5-a), compound (4-c) (15.0 mg, 0.011 mmol) was converted to compound (1-16) as a white solid (3.3 mg, 38% yield). Analysis results of NMR spectrum and reaction scheme are shown below.

$^1$H NMR (400 MHz, CDCl$_3$:CD$_3$OD=10:1) δ 0.80 (t, J=6.8 Hz, 6H), 1.20 (d, J=19.0 Hz, 56H), 1.35-1.44 (m, 2H), 1.49-1.55 (m, 6H), 2.08 (t, J=7.8 Hz, 2H), 2.12 (t, J=7.8 Hz, 2H), 3.09-3.13 (m, 2H), 3.39-3.48 (m, 2H), 3.60-3.66 (m, 3H), 3.68-3.73 (m, 3H), 3.81 (dd, J=10.0, 3.9 Hz, 1H), 3.87 (d, J=3.9 Hz, 1H), 4.09-4.13 (m, 1H), 4.83 (d, J=3.9 Hz, 1H); $^{13}$C NMR (100 MHz, CDCl$_3$:CD$_3$OD=10:1) 14.2 (2C), 22.8, 25.7, 25.9, 26.0, 26.7, 28.9, 29.0, 29.1, 29.4 (2C), 29.5 (2C), 29.6, 29.7 (2C), 29.3, 29.8 (12C), 29.9, 32.0 (2C), 32.9, 36.5, 36.8, 39.4, 50.4, 62.1, 67.6, 69.0, 69.9, 70.3, 70.7, 72.2, 75.0, 99.8, 174.4 (2C): HRMS (ESI-TOF) calcd C$_{49}$H$_{96}$N$_2$NaO$_{10}$: (M+Na)$^+$, 895.6957; found: (M+Na)$^+$, 895.6964.

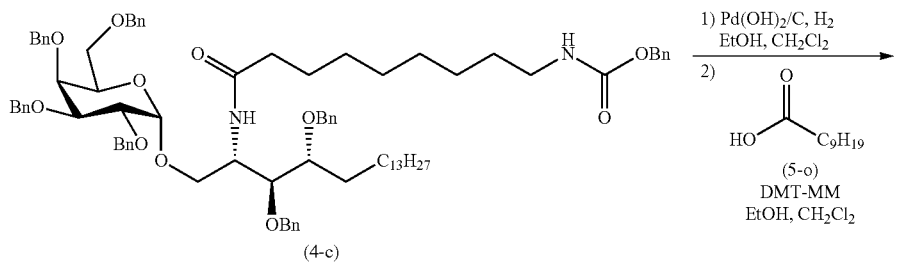

(4-c)

(5-o)
DMT-MM
EtOH, CH$_2$Cl$_2$

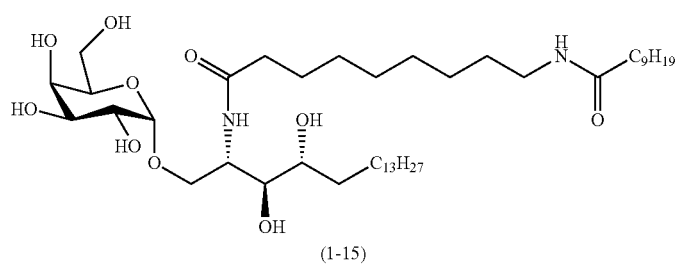

(1-15)

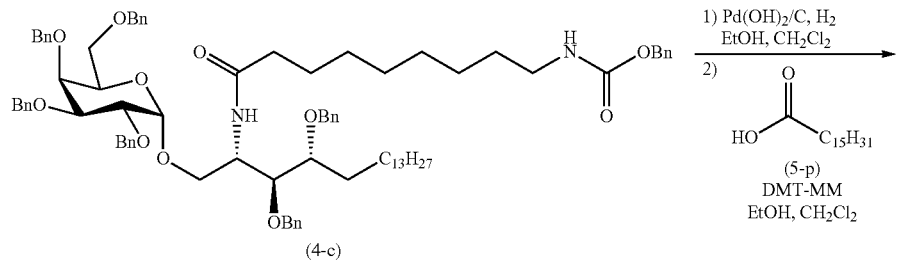

(4-c)

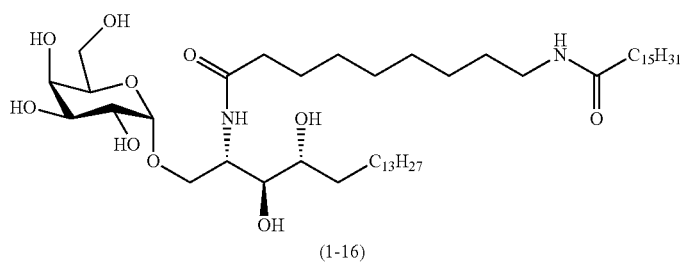

(1-16)

Synthesis Example 17

Synthesis of 9-(8-bromooctanamide)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)nonanamide (Compound (1-17))

In the same manner as the synthesis method of compound (1-1) from compound (4-a) except that compound (4-c) was used instead of compound (4-a) and compound (5-q) was used instead of compound (5-a), compound (4-c) (15.0 mg, 0.011 mmol) was converted to compound (1-17) as a white solid (3.5 mg, 38% yield). Analysis results of NMR spectrum and reaction scheme are shown below.

$^1$H NMR (400 MHz, CDCl$_3$:CD$_3$OD=10:1) δ 0.80 (t, J=6.8 Hz, 3H), 1.17-1.25 (m, 38H), 1.35-1.41 (m, 4H), 1.50-1.56 (m, 4H), 1.75-1.79 (m, 2H), 2.08 (t, J=7.6 Hz, 2H), 2.12 (t, J=7.6 Hz, 2H), 3.08-3.14 (m, 2H), 3.33 (t, J=6.8 Hz, 2H), 3.41-3.47 (m, 2H), 3.61-3.66 (m, 3H), 3.69-3.73 (m, 3H), 3.81 (dd, J=10.0, 3.8 Hz, 1H), 3.87 (d, J=3.8 Hz, 1H), 4.10-4.13 (m, 1H), 4.83 (d, J=3.8 Hz, 1H); $^{13}$C NMR (100 MHz, CDCl$_3$:CD$_3$OD=10:1) δ 14.2, 22.8, 25.7, 25.8, 25.9, 26.7, 28.0, 28.5, 28.9, 29.1 (3C), 29.4, 29.5, 29.5, 29.7, 29.8 (5C), 29.9, 32.0, 32.8 (2C), 34.0, 36.5, 36.6, 39.4, 50.4, 62.1, 67.4, 69.0, 69.9, 70.3, 70.7, 72.2, 75.0, 99.8, 174.2, 174.4: HRMS (ESI-TOF) calcd C$_{41}$H$_{79}$BrN$_2$NaO$_{10}$: (M+Na)$^+$, 861.4810; found: (M+Na)$^+$, 861.4818.

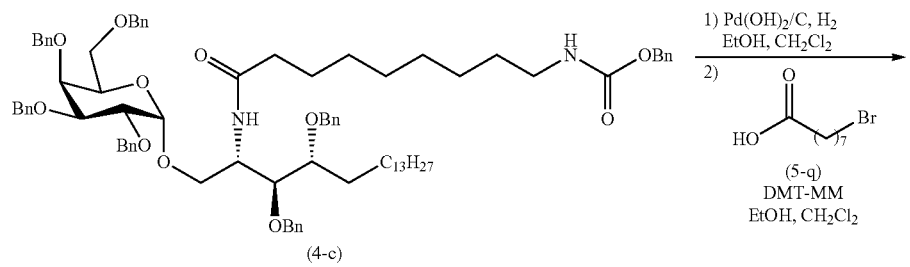

(4-c)

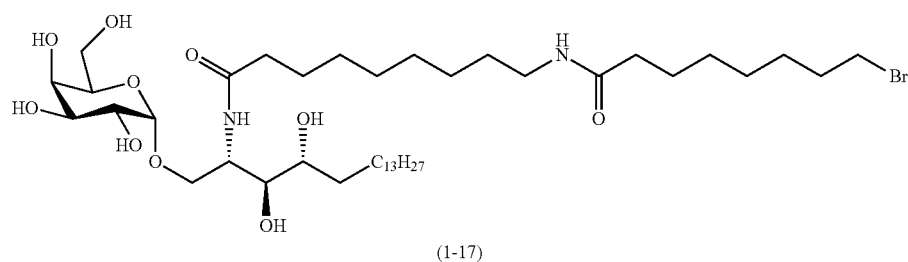

(1-17)

Synthesis Example 18

Synthesis of 10-bromo-N-(9-(((2S,3S,4R)-3,4-dihydroxy-1-(((2S,3R,4S,5S,6R)-3,4,5-trihydroxy-6-(hydroxymethyl)tetrahydro-2H-pyran-2-yl)oxy)octadecan-2-yl)amino)-9-oxononyl)decanamide (Compound (1-18))

In the same manner as the synthesis method of compound (1-1) from compound (4-a) except that compound (4-c) was used instead of compound (4-a) and compound (5-r) was used instead of compound (5-a), compound (4-c) (15.0 mg, 0.011 mmol) was converted to compound (1-18) as a white solid (2.5 mg, 26% yield). Analysis results of NMR spectrum and reaction scheme are shown below.

$^1$H NMR (400 MHz, CDCl$_3$:CD$_3$OD=10:1) δ 0.88 (t, J=6.8 Hz, 3H), 1.25-1.30 (m, 44H), 1.37-1.51 (m, 2H), 1.57-1.67 (m, 4H), 1.82-1.88 (m, 2H), 2.16 (t, J=7.8 Hz, 2H), 2.19 (t, J=7.8 Hz, 2H), 3.17-3.19 (m, 2H), 3.41 (t, J=7.1 Hz, 2H), 3.50-3.56 (m, 2H), 3.68-3.74 (m, 3H), 3.76-3.82 (m, 3H), 3.89 (dd, J=10.0, 3.8 Hz, 1H), 3.93-3.96 (m, 1H), 4.16-4.18 (m, 1H), 4.91 (d, J=3.9 Hz, 1H); $^{13}$C NMR (100 MHz, CDCl$_3$:CD$_3$OD=10:1) δ 13.9, 22.5, 25.5, 25.7, 26.4, 27.9, 28.5, 28.7, 28.8 (3C), 29.1 (3C), 29.2, 29.5, 29.6 (8C), 31.8, 32.6 (2C), 33.9, 36.2, 36.5, 39.2, 50.2, 61.8, 67.4, 68.7, 69.6, 70.1, 70.5, 71.9, 74.7, 99.8, 174.1, 174.2: HRMS(ESI-TOF) calcd C$_{43}$H$_{83}$BrN$_2$NaO$_{10}$: (M+Na)$^+$, 889.5123; found: (M+Na)$^+$, 889.5131.

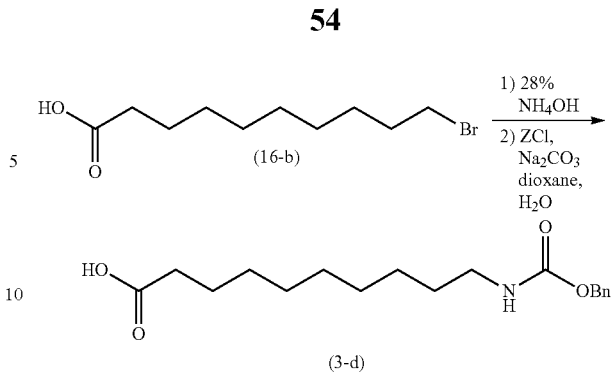

Synthesis of benzyl (10-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)amino)-10-oxodecyl)carbamate (Compound (4-d))

In the same manner as the synthesis method of compound (4-a) from compound (2-a) and compound (3-a) except that compound (3-d) was used instead of compound (3-a), compound (2-a) (20.0 mg, 0.019 mmol) was converted to compound (4-d) as a colorless oil (18.4 mg, 73% yield). Analysis results of NMR spectrum and reaction scheme are shown below.

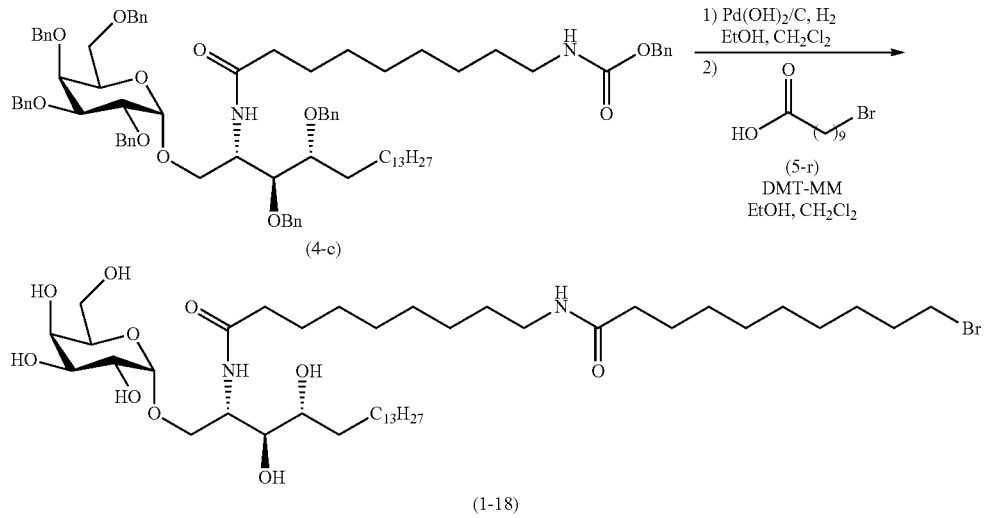

Synthesis Example 19

Synthesis of 10-(((benzyloxy)carbonyl)amino)decanoic acid (Compound (3-d))

In the same manner as the synthesis method of compound (3-c) from compound (16-a) except that compound (16-b) was used instead of compound (16-a), compound (16-b) (300 mg, 1.19 mmol) was converted to compound (3-d) as a colorless oil (118 mg, 31% yield). The reaction scheme is shown below.

$^1$H NMR (400 MHz, CDCl$_3$) δ 0.88 (t, J=6.8 Hz, 3H), 1.20-1.27 (m, 34H), 1.44-1.50 (m, 4H), 1.84-1.87 (m, 2H), 1.90-1.96 (m, 2H), 3.12-3.18 (m, 2H), 3.41 (dd, J=9.2, 6.3 Hz, 1H), 3.46-3.51 (m, 2H), 3.71-3.76 (m, 1H), 3.84-3.93 (m, 4H), 3.98-4.06 (m, 2H), 4.13-4.18 (m, 1H), 4.36 (d, J=11.4 Hz, 1H), 4.42 (d, J=11.4 Hz, 1H), 4.46 (d, J=11.4 Hz, 1H), 4.51 (d, J=11.4 Hz, 1H), 4.54-4.60 (m, 2H), 4.64 (d, J=11.4 Hz, 1H), 4.66-4.71 (m, 1H), 4.73-4.82 (m, 4H), 4.84 (d, J=3.6 Hz, 1H), 4.91 (d, J=11.4 Hz, 1H), 5.09 (s, 2H), 6.17 (d, J=8.5 Hz, 1H), 7.21-7.37 (m, 35H); $^{13}$C NMR (100 MHz, CDCl$_3$) δ 14.1, 22.7, 25.6, 26.0, 26.7, 29.2, 29.3 (3C), 29.4, 29.6, 29.7 (9C), 29.8, 29.9, 31.9, 36.6, 41.0, 50.2, 66.5, 67.9, 69.2, 69.9, 71.6, 72.8, 73.5, 73.6 (2C), 74.7 (2C), 76.6, 78.6, 78.8, 80.1, 99.4, 127.4 (2C), 127.5 (3C), 127.6, 127.7, 127.8 (8C), 127.9 (2C), 128.0, 128.1, 128.2 (4C), 128.3 (6C), 128.4 (4C), 128.5 (2C), 136.6, 137.5, 138.3, 138.4, 138.6 (2C), 138.7, 156.3, 172.8; HRMS (ESI-TOF) calcd $C_{84}H_{110}N_2NaO_{11}$: $(M+Na)^+$, 1345.8002; found: $(M+Na)^+$, 1345.8001.

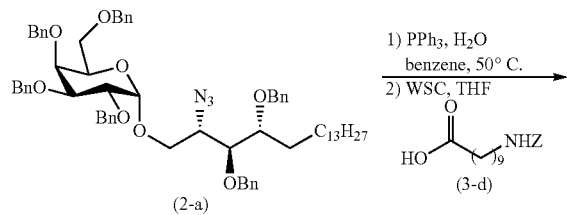

0.011 mmol) was converted to compound (1-19) as a white solid (2.0 mg, 21% yield). Analysis results of NMR spectrum and reaction scheme are shown below.

$^1$H NMR (400 MHz, $CDCl_3$:$CD_3OD$=10:1) δ 0.88 (t, J=6.7 Hz, 6H), 1.25-1.29 (m, 56H), 1.45-1.49 (m, 2H), 1.55-1.67 (m, 6H), 2.15 (t, J=7.7 Hz, 2H), 2.20 (t, J=7.7 Hz, 2H), 3.18-3.22 (m, 2H), 3.48-3.59 (m, 2H), 3.67-3.74 (m, 3H), 3.76-3.82 (m, 3H), 3.89 (dd, J=10.8, 3.8 Hz, 1H), 3.95 (d, J=3.8 Hz, 1H), 4.19 (d, J=3.8 Hz, 1H), 4.91 (d, J=3.8 Hz, 1H); $^{13}$C NMR (100 MHz, $CDCl_3$:$CD_3OD$=10:1) δ 13.9 (2C), 22.5 (2C), 25.6, 25.7 (2C), 26.6, 28.9 (2C), 29.0, 29.1, 29.2 (2C), 29.4, 29.6, 29.5 (3C), 29.6 (12C), 31.8 (2C), 32.6, 36.3, 36.5, 39.2, 50.2, 61.8, 67.4, 68.8, 69.6, 70.1, 70.5, 72.0, 74.7, 99.5, 174.1, 174.2: HRMS (ESI-TOF) calcd $C_{49}H_{96}N_2NaO_{10}$: $(M+Na)^+$, 895.6957; found: $(M+Na)^+$, 895.6961.

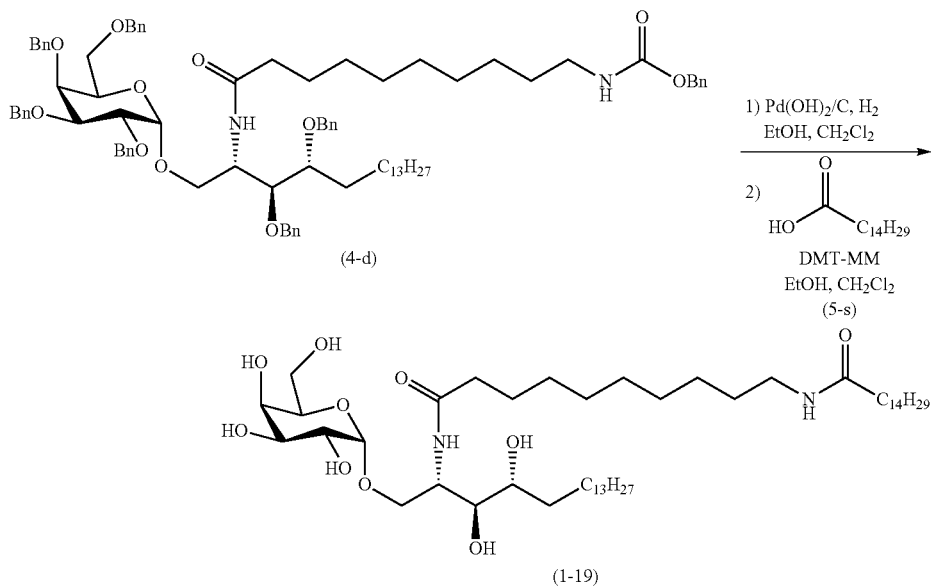

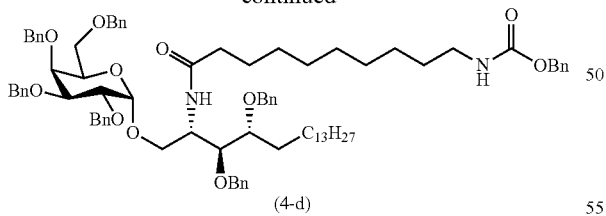

Synthesis of N-(10-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-10-oxodecyl)pentadecanamide (Compound (1-19))

In the same manner as the synthesis method of compound (1-1) from compound (4-a) except that compound (4-d) was used instead of compound (4-a) and compound (5-s) was used instead of compound (5-a), compound (4-d) (15.0 mg, Synthesis Example 20

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-10-nonanamidedecanamide (Compound (1-20))

In the same manner as the synthesis method of compound (1-1) from compound (4-a) except that compound (4-d) was used instead of compound (4-a) and compound (5-t) was used instead of compound (5-a), compound (4-d) (20.0 mg, 0.015 mmol) was converted to compound (1-20) as a white solid (3.5 mg, 30% yield). Analysis results of NMR spectrum and reaction scheme are shown below.

$^1$H NMR (400 MHz, $CDCl_3$:$CD_3OD$=10:1) δ 0.88 (t, J=6.3 Hz, 6H), 1.23-1.31 (m, 44H), 1.46-1.49 (m, 2H), 1.57-1.63 (m, 6H), 2.15 (t, J=7.7 Hz, 2H), 2.20 (t, J=7.7 Hz, 2H), 3.16-3.22 (m, 2H), 3.48-3.55 (m, 2H), 3.69-3.74 (m, 3H), 3.76-3.81 (m, 3H), 3.89 (dd, J=10.0, 3.8 Hz, 1H), 3.94-3.97 (m, 1H), 4.17-4.20 (m, 1H), 4.90-4.93 (m, 1H); $^{13}$C NMR (100 MHz, $CDCl_3$:$CD_3OD$=10:1) δ 13.9 (2C), 22.5 (2C), 25.5, 25.6, 26.7 (2C), 28.9, 29.0 (2C), 29.2 (2C), 29.4, 29.5, 29.6 (10C), 31.7, 31.8, 32.5, 36.3, 36.6, 39.3, 50.1, 61.9, 67.5, 68.8, 69.7, 70.1, 70.4, 72.0, 74.7, 99.5, 174.1, 174.2: HRMS (ESI-TOF) calcd $C_{43}H_{84}N_2NaO_{10}$: (M+Na)$^+$, 811.6018; found: (M+Na)$^+$, 811.6022.

compound (4-e) as a colorless oil (19.8 mg, 78% yield). Analysis results of NMR spectrum and reaction scheme are shown below.

$^1$H NMR (400 MHz, CDCl$_3$) δ 0.88 (t, J=6.8 Hz, 3H), 1.20-1.29 (m, 36H), 1.44-1.50 (m, 4H), 1.62-1.68 (m, 2H),

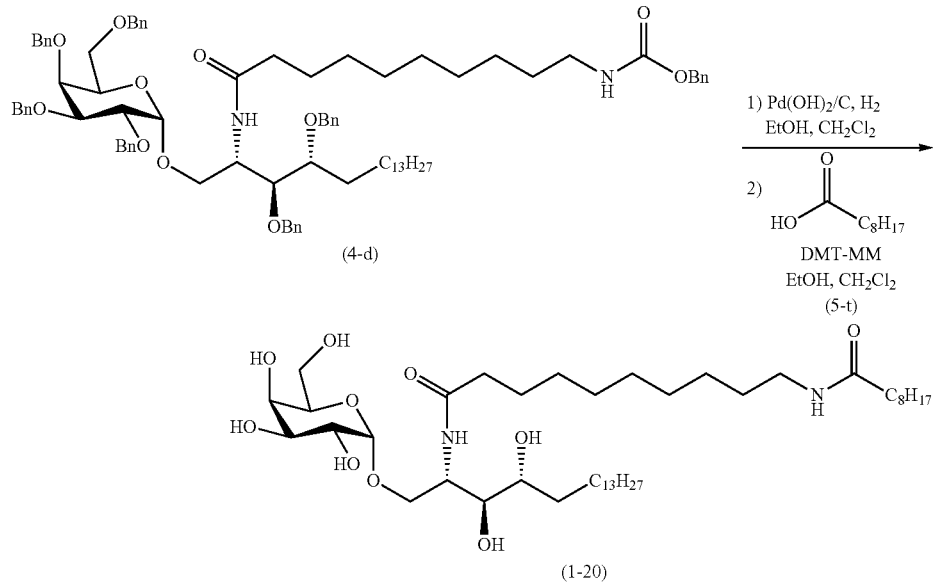

Synthesis Example 21

Synthesis of 11-(((benzyloxy)carbonyl)amino)undecanoic acid (Compound (3-e))

In the same manner as the synthesis method of compound (3-a) from compound (14-a) except that compound (14-d) was used instead of compound (14-a), compound (14-d) (300 mg, 1.49 mmol) was converted to compound (3-e) as a colorless oil (176 mg, 35% yield). The reaction scheme is shown below.

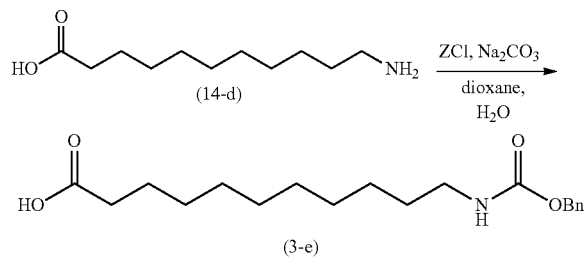

1.88-1.98 (m, 2H), 3.13-3.20 (m, 2H), 3.41 (dd, J=9.2, 6.3 Hz, 1H), 3.46-3.52 (m, 2H), 3.73 (dd, J=10.8, 3.8 Hz, 1H), 3.84-3.87 (m, 1H), 3.90-3.94 (m, 3H), 3.98-4.06 (m, 2H), 4.13-4.19 (m, 1H), 4.36 (d, J=11.7 Hz, 1H), 4.42 (d, J=11.7 Hz, 1H), 4.47 (d, J=11.7 Hz, 1H), 4.51 (d, J=11.7 Hz, 1H), 4.54-4.60 (m, 2H), 4.64 (d, J=11.7 Hz, 1H), 4.68-4.72 (m, 1H), 4.73-4.82 (m, 4H), 4.84 (d, J=3.6 Hz, 1H), 4.91 (d, J=11.7 Hz, 1H), 5.09 (s, 2H), 6.17 (d, J=8.8 Hz, 1H), 0.7.21-7.37 (m, 35H); $^{13}$C NMR (100 MHz, CDCl$_3$) δ 14.1, 22.7, 25.6, 26.1, 26.7, 29.2, 29.3, 29.4 (2C), 29.5, 29.6, 29.7 (8C), 29.8, 29.9, 31.9, 36.6, 41.1, 50.2, 66.5, 69.2 (2C), 69.9, 71.6, 72.8, 73.5, 73.5 (2C), 74.7 (2C), 76.6, 78.6, 78.8, 80.1, 99.5, 127.4 (2C), 127.5 (3C), 127.6, 127.7, 127.8 (8C), 127.9 (2C), 128.0, 128.1, 128.2 (4C), 128.3 (6C), 128.4 (4C), 128.5 (2C), 136.6, 137.5, 138.3, 138.4, 138.6 (2C), 138.7, 156.3, 172.8; HRMS (ESI-TOF) calcd $C_{85}H_{112}N_2NaO_{11}$: (M+Na)$^+$, 1359.8158; found: (M+Na)$^+$, 1359.8150.

Synthesis of benzyl (12-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)amino)-12-oxododecyl)carbamate (Compound (4-e))

In the same manner as the synthesis method of compound (4-a) from compound (2-a) and compound (3-a) except that compound (3-e) was used instead of compound (3-a), compound (2-a) (20.0 mg, 0.019 mmol) was converted to

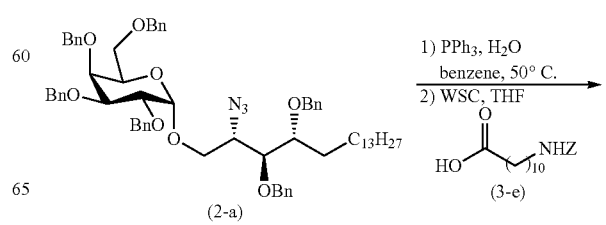

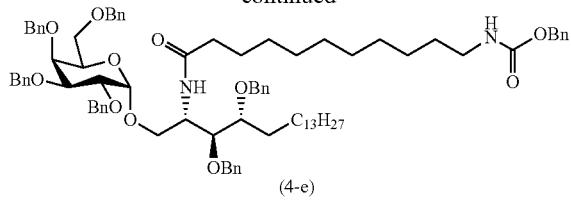

(4-e)

Synthesis of N-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)tetradecanamide (Compound (1-21))

In the same manner as the synthesis method of compound (1-1) from compound (4-a) except that compound (4-e) was used instead of compound (4-a) and compound (5-u) was used instead of compound (5-a), compound (4-e) (14.3 mg, 0.011 mmol) was converted to compound (1-21) as a colorless oil (4.6 mg, 48% yield). Analysis results of NMR spectrum and reaction scheme are shown below.

$^1$H NMR (400 MHz, CDCl$_3$:CD$_3$OD=10:1) δ 0.88 (t, J=6.5 Hz, 6H), 1.24-1.29 (m, 56H), 1.47-1.49 (m, 2H), 1.58-1.62 (m, 6H), 2.15 (t, J=7.7 Hz, 2H), 2.19 (t, J=7.7 Hz, 2H), 3.16-3.22 (m, 2H), 3.52-3.55 (m, 2H), 3.68-3.73 (m, 3H), 3.77-3.80 (m, 3H), 3.88 (dd, J=10.0, 3.6 Hz, 1H), 3.94-3.97 (m, 1H), 4.17-4.19 (m, 1H), 4.90-4.92 (m, 1H); $^{13}$C NMR (100 MHz, CDCl$_3$:CD$_3$OD=10:1) δ 13.9 (2C), 22.5 (2C), 25.6, 25.7 (2C), 26.6, 28.7 (2C), 29.0 (2C), 29.2 (2C), 29.4, 29.5 (3C), 29.6 (13C), 31.8 (2C), 32.4, 36.3, 36.5, 39.3, 50.1, 61.8, 67.4, 68.7, 69.7, 70.0, 70.4, 71.9, 74.5, 99.5, 174.0, 174.2: HRMS (ESI-TOF) calcd C$_{49}$H$_{96}$N$_2$NaO$_{10}$:(M+Na)$^+$, 895.6957; found:(M+Na)$^+$, 895.6961.

Synthesis Example 22

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-octanamideundecanamide (Compound (1-22))

In the same manner as the synthesis method of compound (1-1) from compound (4-a) except that compound (4-e) was used instead of compound (4-a) and compound (5-v) was used instead of compound (5-a), compound (4-e) (20.0 mg, 0.015 mmol) was converted to compound (1-22) as a white solid (2.2 mg, 19% yield). Analysis results of NMR spectrum and reaction scheme are shown below.

$^1$H NMR (400 MHz, CDCl$_3$:CD$_3$OD=10:1) δ 0.88 (t, J=7.1 Hz, 6H), 1.23-1.32 (m, 44H), 1.47-1.49 (m, 2H), 1.58-1.66 (m, 6H), 2.16 (t, J=7.9 Hz, 2H), 2.20 (t, J=7.9 Hz, 2H), 3.19 (t, J=7.2 Hz, 2H), 3.50-3.54 (m, 2H), 3.67-3.74 (m, 3H), 3.76-3.81 (m, 3H), 3.89 (dd, J=10.8, 3.8 Hz, 1H), 3.94-3.97 (m, 1H), 4.19 (d, J=3.8 Hz, 1H), 4.92 (d, J=3.8 Hz, 11H); $^{13}$C NMR (100 MHz, CDCl$_3$:CD$_3$OD=10:1) δ 13.9 (2C), 22.4, 22.5, 25.6, 25.7 (2C), 26.6, 28.9, 29.0 (2C), 29.1, 29.2 (2C), 29.5, 29.6 (9C), 31.6, 31.8 (2C), 32.6, 36.4, 36.6, 39.3, 50.1, 61.9, 67.5, 68.8, 69.6, 70.1, 70.4, 72.0, 74.7, 99.5, 174.1, 174.2: HRMS (ESI-TOF) calcd C$_{43}$H$_{84}$N$_2$NaO$_{10}$: (M+Na)$^+$, 811.6018; found: (M+Na)$^+$, 811.6022.

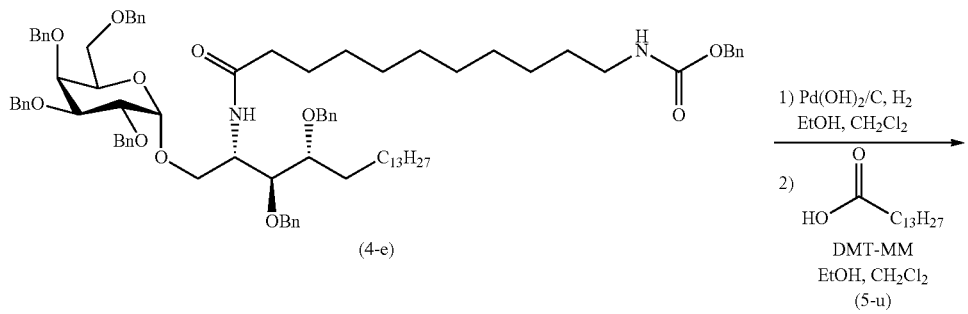

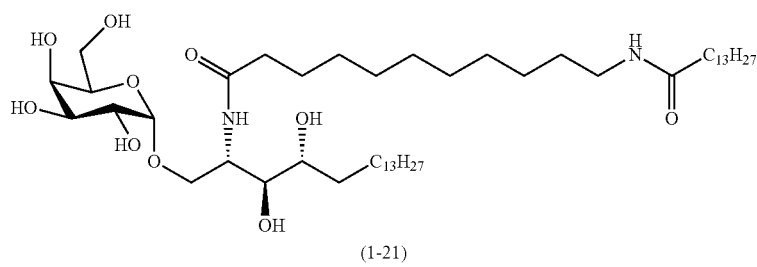

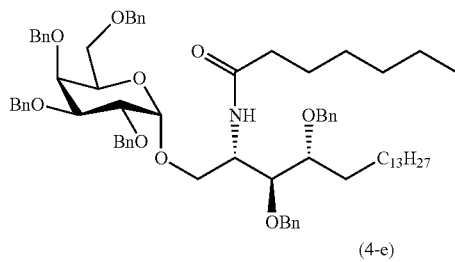
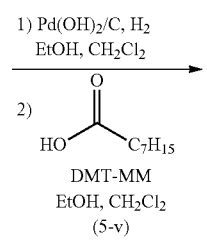

(4-e)

1) Pd(OH)₂/C, H₂
   EtOH, CH₂Cl₂

2) HO–C(O)–C₇H₁₅
   DMT-MM
   EtOH, CH₂Cl₂
   (5-v)

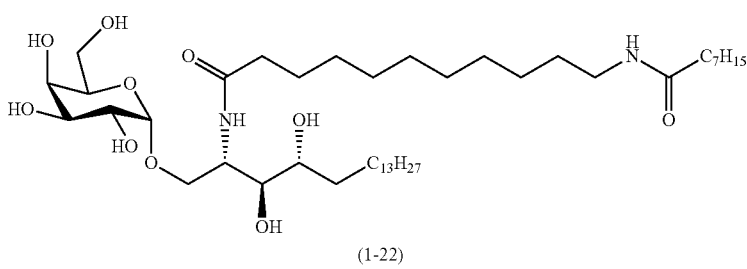

(1-22)

Synthesis Example 23

Synthesis of 12-(2,2,2-trifluoroacetamide)dodecanoic acid (Compound (8-a))

To a stirred suspension of compound (14-a) (1.0 g, 4.6 mmol) in MeOH (7.0 mL) and Et₃N (0.70 mL) was added methyl 2,2,2-trifluoroacetate (0.68 mL, 6.9 mmol) at room temperature. After stirring for 18 hr at this temperature, the obtained mixture was diluted with EtOAc, washed with saturated KHSO₄ aqueous solution, and dried over Mg₂SO₄. Concentration under reduced pressure gave compound (8-a) as a white solid (1.32 g, 92% yield). Analysis results of NMR spectrum and reaction scheme are shown below.

$^1$H NMR (400 MHz, CDCl$_3$) δ $^1$H-NMR (CDCl$_3$) δ:1.26-1.35 (m, 14H), 1.57-1.64 (m, 4H), 2.35 (t, J=7.6 Hz, 2H), 3.36 (dt, J=6.8, 6.8 Hz, 2H), 6.29-6.32 (m, 1H); $^{13}$C NMR (100 MHz, CDCl$_3$) δ 24.6, 26.6, 28.9 (2C), 29.0, 29.1, 29.3 (3C), 34.0, 40.0, 115.8 (q, $J_{C-F}$=286.3 Hz), 157.2 (q, $J_{C-F}$=37.2 Hz), 180.1; HRMS (ESI-TOF) calcd C$_{14}$H$_{23}$F$_3$NO$_3$: (M−H)⁻, 310.1636; found: (M−H)⁻, 310.1639.

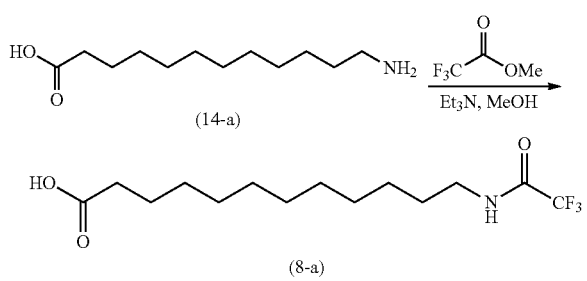

Synthesis of N-((2S,3S,4R)-3,4-bis(benzyloxy)-1-(((2S,3R,4S,5S)-3,4,5-tris(benzyloxy)-6-((benzyloxy)methyl)tetrahydro-2H-pyran-2-yl)oxy)octadecan-2-yl)-12-(2,2,2-trifluoroacetamide) dodecanamide (Compound (9-a))

In the same manner as the synthesis method of compound (4-a) from compound (2-a) and compound (3-a) except that compound (8-a) was used instead of compound (3-a), compound (2-a) (40.0 mg, 0.038 mmol) was converted to compound (9-a) as a colorless oil (22.6 mg, 45% yield). Analysis results of NMR spectrum and reaction scheme are shown below.

$^1$H NMR (400 MHz, CDCl$_3$) δ 0.88 (t, J=6.8 Hz, 3H), 1.22-1.28 (m, 40H), 1.48-1.68 (m, 4H), 1.90-1.96 (m, 2H), 3.33 (td, J=6.8, 6.8 Hz, 2H), 3.41 (dd, J=9.4, 6.3 Hz, 1H), 3.48-3.50 (m, 2H), 3.73 (dd, J=11.0, 3.6 Hz, 1H), 3.84-3.88 (m, 2H), 3.89-3.93 (m, 2H), 4.00-4.06 (m, 2H), 4.14-4.17 (m, 1H), 4.36 (d, J=11.9 Hz, 1H), 4.42 (d, J=11.9 Hz, 1H), 4.47 (d, J=11.9 Hz, 2H), 4.51 (d, J=11.9 Hz, 1H), 4.54-4.60 (m, 2H), 4.64 (d, J=11.9 Hz, 1H), 4.71-4.81 (m, 3H), 4.84 (d, J=3.6 Hz, 1H), 4.92 (d, J=11.9 Hz, 1H), 6.15 (d, J=8.5 Hz, 1H), 6.28-6.31 (m, 1H), 7.21-7.38 (m, 30H); $^{13}$C NMR (100 MHz, CDCl$_3$) δ 14.1, 22.7, 25.6, 26.1, 26.6, 28.9, 29.1 (2C), 29.4, 29.7 (11C), 29.8, 29.9, 31.9, 36.6, 40.0, 50.3, 65.8, 69.3, 69.5, 70.0, 71.7, 72.9, 73.5, 73.6, 74.7, 74.8, 76.6, 78.6, 78.9, 80.2, 99.6, 117.9 (q, $J_{C-F}$=280.9 Hz), 127.4 (2C), 127.5, 127.6 (2C), 127.7 (3C), 127.8 (2C), 127.9 (6C), 128.3 (8C), 128.4 (6C), 137.6, 138.4 (2C), 138.6 (2C), 138.7, 156.6 (q, $J_{C-F}$=37.6 Hz), 172.8: HRMS(ESI-TOF) calcd C$_{80}$H$_{107}$F$_3$N$_2$NaO$_{10}$: (M+Na)⁺, 1335.7770; found: (M+Na)⁺, 1335.7763.

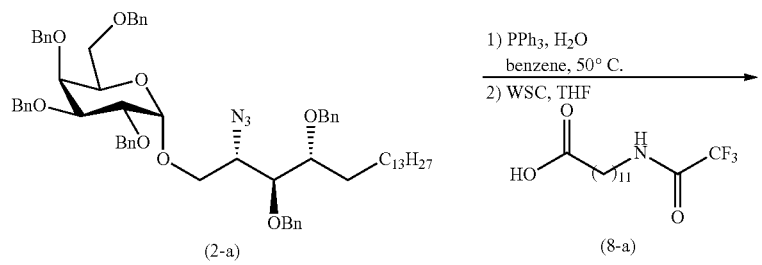

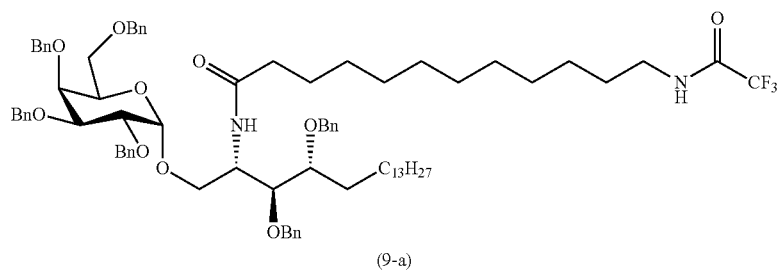

Synthesis of N-(12-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)amino)-12-oxododecyl)benzamide (Compound (13-a))

A mixture of compound (9-a) (10 mg, 0.0076 mmol) in 3M NaOH aqueous solution (0.2 mL), MeOH (0.4 mL) and THF (0.4 mL) was stirred at 40° C. for 0.5 hr, and then concentrated under reduced pressure to give a crude amine. This amine was dissolved in 1M NaOH aqueous solution (0.2 mL) and CH$_2$Cl$_2$ (0.2 mL). Benzoyl chloride (compound (10-a)) (8.8 µL, 0.076 mmol) was added to the stirred mixture at room temperature. The obtained mixture was stirred at this temperature for 0.5 hr, and diluted with saturated NaHCO$_3$ aqueous solution. The whole mixture was extracted with EtOAc. The extract was washed with saturated NaHCO$_3$, brine, and dried over MgSO$_4$, and concentrated under reduced pressure to give an oily residue, which was purified by flash chromatography over silica gel with n-hexane-EtOAc (2:1) to give compound (13-a) as a colorless oil (6.7 mg, 68% yield). Analysis results of NMR spectrum and reaction scheme are shown below.

$^1$H NMR (400 MHz, CDCl$_3$) δ 0.88 (t, J=6.9 Hz, 3H), 1.22-1.25 (m, 40H), 1.46-1.50 (m, 2H), 1.58-1.63 (m, 2H), 1.90-1.96 (m, 2H), 3.38-3.51 (m, 5H), 3.73 (dd, J=10.7, 3.7 Hz, 1H), 3.84-3.88 (m, 2H), 3.89-3.94 (m, 2H), 4.01-4.04 (m, 2H), 4.14-4.17 (m, 1H), 4.36 (d, J=11.9 Hz, 1H), 4.42-4.47 (m, 2H), 4.51 (d, J=11.9 Hz, 1H), 4.55-4.58 (m, 2H), 4.64 (d, J=11.9 Hz, 1H), 4.73 (d, J=11.9 Hz, 1H), 4.76-4.81 (m, 3H), 4.84 (d, J=3.4 Hz, 1H), 4.91 (d, J=11.9 Hz, 1H), 6.06-6.09 (m, 1H), 6.13 (d, J=8.5 Hz, 1H), 7.23-7.35 (m, 30H), 7.41-7.43 (m, 2H), 7.48-7.50 (m, 1H), 7.73-7.76 (m, 2H); $^{13}$C NMR (100 MHz, CDCl$_3$) δ 14.1, 22.7, 25.6, 26.1, 27.0, 29.3, 29.4 (2C), 29.5 (2C), 29.6, 29.7 (10C), 29.8, 31.9, 36.6, 40.1, 50.3, 69.2, 69.5, 69.9, 71.7, 72.9, 73.4, 73.6 (2C), 74.7 (2C), 76.6, 78.6, 78.9, 80.1, 99.6, 126.8 (2C), 127.4 (2C), 127.5 (3C), 127.6, 127.7, 127.8 (6C), 127.9 (2C), 128.2 (2C), 128.3 (8C), 128.4 (4C), 128.5 (2C), 131.3 (2C), 134.8, 137.5, 138.4 (2C), 138.6 (2C), 138.7, 167.4, 172.8: HRMS (ESI-TOF) calcd C$_{85}$H$_{112}$N$_2$NaO$_{10}$: (M+Na)$^+$, 1343.8209; found:(M+Na)$^+$, 1343.8214.

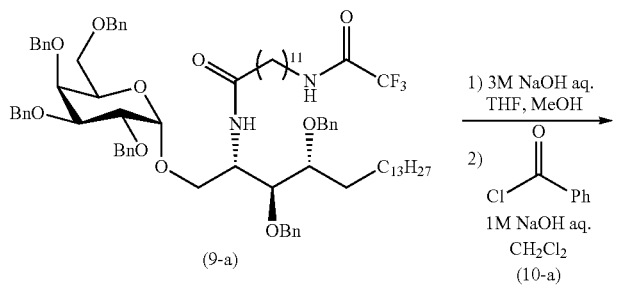

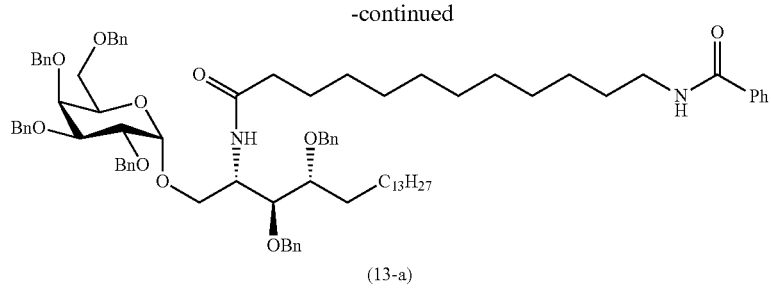

(13-a)

Synthesis of N-(12-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-12-oxododecyl)benzamide (Compound (1-23))

A mixture of compound (13-a) (6.0 mg, 0.0033 mmol) and Pd(OH)$_2$/C (20% wt on carbon, 5 mg, 0.007 mmol) in EtOH (1.2 mL) and CH$_2$Cl$_2$ (0.4 mL) was stirred for 22 hr at room temperature under H$_2$ atmosphere (0.5 MPa), and then filtrated through Celite pad with EtOH/CH$_2$Cl$_2$ (3:1). The filtrate was concentrated under reduced pressure to give compound (1-23) as a white solid (2.6 mg, 99% yield). Analysis results of NMR spectrum and reaction scheme are shown below.

$^1$H NMR (400 MHz, CDCl$_3$:CD$_3$OD=10:1) δ 0.88 (t, J=6.5 Hz, 3H), 1.25-1.28 (m, 38H), 1.58-1.63 (m, 6H), 2.19 (t, J=7.4 Hz, 2H), 3.38-3.43 (m, 2H), 3.51-3.54 (m, 2H), 3.70-3.73 (m, 3H), 3.77-3.81 (m, 3H), 3.89 (dd, J=10.0, 5.0 Hz, 1H), 3.94-3.96 (m, 1H), 4.17-4.20 (m, 1H), 4.91 (d, J=3.4 Hz, 1H), 7.44 (t, J=7.7 Hz, 2H), 7.49 (d, J=7.6 Hz, 1H), 7.76 (d, J=7.9 Hz, 2H); $^{13}$C NMR (100 MHz, CDCl$_3$:CD3OD=10:1) δ 13.9, 22.5, 25.6, 25.7, 26.8, 29.0, 29.1 (2C), 29.2 (2C), 29.3, 29.5. 29.6 (11C), 31.8, 32.7, 36.4, 39.9, 50.2, 61.9, 67.5, 68.8, 69.6, 70.4, 72.0, 74.9, 99.6, 126.7 (2C), 128.4 (2C), 134.4, 168.2, 174.2; HRMS (ESI-TOF) calcd C$_{43}$H$_{76}$N$_2$NaO$_{10}$: (M+Na)$^+$, 803.5392; found: (M+Na)$^+$, 803.5395.

Synthesis Example 24

Synthesis of 9-(2,2,2-trifluoroacetamide)nonanoic acid (Compound (8-b))

In the same manner as the synthesis method of compound (8-a) from compound (14-a) except that compound (14-e) was used instead of compound (14-a), compound (14-e) (220 mg, 1.27 mmol) was converted to compound (8-b) as a colorless oil (259 mg, 76% yield). Reaction scheme is shown below.

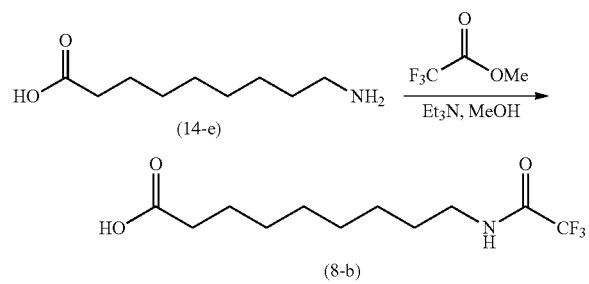

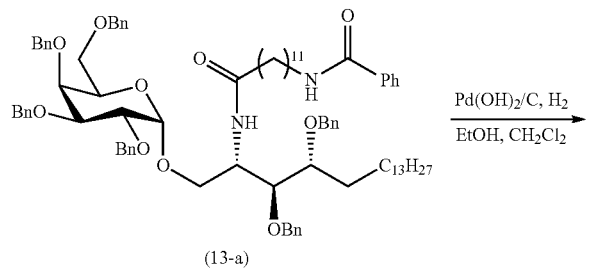

(13-a)

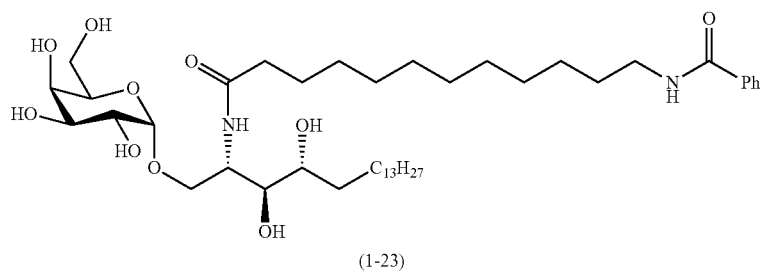

(1-23)

Synthesis of N-((2S,3S,4R)-3,4-bis(benzyloxy)-1-(((2S,3R,4S,5S)-3,4,5-tris(benzyloxy)-6-((benzyloxy)methyl)tetrahydro-2H-pyran-2-yl)oxy)octadecan-2-yl)-9-(2,2,2-trifluoroacetamide)nonanamide (Compound (9-b))

In the same manner as the synthesis method of compound (4-a) from compound (2-a) and compound (3-a) except that compound (8-b) was used instead of compound (3-a), compound (2-a) (80.0 mg, 0.077 mmol) was converted to compound (9-b) as a colorless oil (32.6 mg, 33% yield). Analysis results of NMR spectrum and reaction scheme are shown below.

$^1$H NMR (400 MHz, CDCl$_3$) δ 0.88 (t, J=7.0 Hz, 3H), 1.19-1.30 (m, 32H), 1.46-1.53 (m, 4H), 1.58-1.66 (m, 2H), 1.89-1.96 (m, 2H), 3.29 (dt, J=6.7, 6.7 Hz, 2H), 3.40 (dd, J=9.2, 6.3 Hz, 1H), 3.46-3.52 (m, 2H), 3.73 (dd, J=11.0, 3.8 Hz, 1H), 3.85-3.87 (m, 2H), 3.90-3.94 (m, 2H), 4.00-4.06 (m, 2H), 4.14-4.20 (m, 1H), 4.36 (d, J=11.9 Hz, 1H), 4.42 (d, J=11.9 Hz, 1H), 4.47 (d, J=11.9 Hz, 1H), 4.51 (d, J=11.9 Hz, 1H), 4.57 (d, J=11.9 Hz, 1H), 4.58 (d, J=11.9 Hz, 1H), 4.64 (d, J=11.9 Hz, 1H), 4.71-4.81 (m, 4H), 4.84 (d, J=3.6 Hz, 1H), 4.92 (d, J=11.9 Hz, 1H), 6.18 (d, J=8.5 Hz, 1H), 6.31-6.34 (m, 1H), 7.24-7.37 (m, 30H); $^{13}$C NMR (100 MHz, CDCl$_3$) δ 14.1, 22.7, 25.4, 26.1, 26.5, 28.8, 28.9, 29.1 (2C), 29.4, 29.6 (6C), 29.8 (2C), 29.9, 31.9, 36.5, 39.9, 50.3, 66.6, 69.3, 69.5, 70.0, 71.7, 72.9, 73.4, 73.6, 74.7 (2C), 76.6, 78.6, 78.9, 80.1, 99.6, 115.8 (q, J$_{C-F}$=285.6 Hz), 127.4 (2C), 127.5 (3C), 127.7 (3C), 127.8 (6C), 127.9 (2C), 128.2 (2C), 128.3 (8C), 128.4 (4C), 137.5, 138.4 (2C), 138.6 (3C), 157.6 (q, J$_{C-F}$=36.6 Hz), 172.7; HRMS (ESI-TOF) calcd C$_{77}$H$_{101}$F$_3$N$_2$NaO$_{10}$: (M+Na)$^+$, 1293.7301; found: (M+Na)$^+$, 1293.7311.

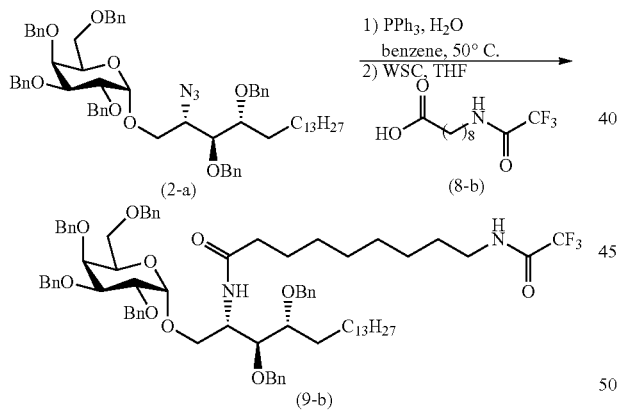

Synthesis of N-(9-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)amino)-9-oxononyl)benzamide (Compound (13-b))

In the same manner as the synthesis method of compound (13-a) from compound (9-a) except that compound (9-b) was used instead of compound (9-a), compound (9-b) (10.0 mg, 0.0079 mmol) was converted to compound (13-b) as a colorless oil (8.2 mg, 81% yield). Analysis results of NMR spectrum and reaction scheme are shown below.

$^1$H NMR (400 MHz, CDCl$_3$) δ 0.88 (t, J=7.0 Hz, 3H), 1.21-1.30 (m, 33H), 1.46-1.68 (m, 4H), 1.87-1.97 (m, 2H), 3.41-3.44 (m, 11H), 3.41 (td, J=6.1, 6.1 Hz, 2H), 3.47-3.51 (m, 2H), 3.73 (dd, J=11.0, 3.8 Hz, 1H), 3.84-3.88 (m, 2H), 3.91-3.94 (m, 3H), 4.00-4.06 (m, 2H), 4.15-4.18 (m, 1H), 4.36 (d, J=11.9 Hz, 1H), 4.42 (d, J=11.9 Hz, 1H), 4.46 (d, J=11.9 Hz, 1H), 4.51 (d, J=11.9 Hz, 1H), 4.55-4.58 (m, 2H), 4.64 (d, J=11.9 Hz, 1H), 4.71-4.81 (m, 4H), 4.85 (d, J=3.8 Hz, 1H), 4.91 (d, J=11.9 Hz, 1H), 6.05-6.07 (m, 1H), 6.15 (d, J=8.8 Hz, 1H), 7.21-7.38 (m, 30H), 7.40-7.44 (m, 2H), 7.47-7.49 (m, 1H), 7.73-7.75 (m, 2H); $^{13}$C NMR (100 MHz, CDCl$_3$) δ 14.1, 22.7, 25.5, 26.1, 26.9, 29.1, 29.2, 29.4, 29.6, 29.7 (7C), 29.8 (2C), 29.9, 31.9, 36.5, 40.0, 50.3, 69.3, 69.5, 70.0, 71.7, 72.9, 73.4, 73.6 (2C), 74.7 (2C), 77.2, 78.6, 78.9, 80.1, 99.6, 126.8 (2C), 127.4 (2C), 127.6, 127.5 (3C), 127.7 (2C), 127.8 (6C), 127.9 (2C), 128.2 (2C), 128.3 (8C), 128.4 (4C), 128.5 (2C), 131.3, 134.8, 137.5, 138.4 (2C), 138.6 (2C), 138.7, 167.4, 172.7; HRMS (ESI-TOF) calcd C$_{82}$H$_{106}$N$_2$NaO$_{10}$: (M+Na)$^+$, 1301.7740; found: (M+Na)$^+$, 1301.7748.

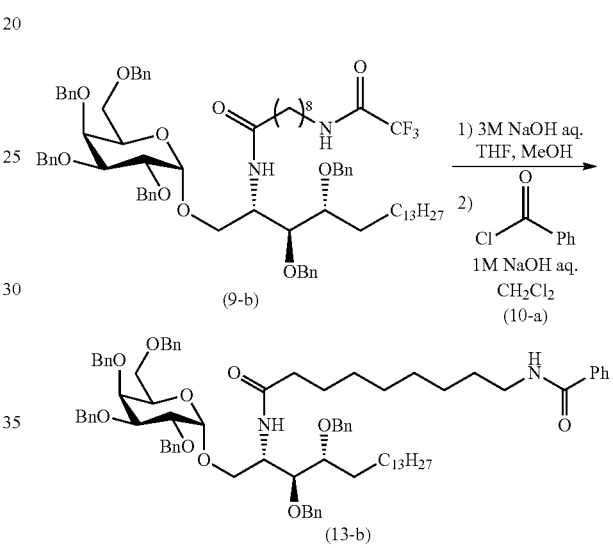

Synthesis of N-(9-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-9-oxononyl)benzamide (Compound (1-24))

In the same manner as the synthesis method of compound (1-23) from compound (13-a) except that compound (13-b) was used instead of compound (13-a), compound (13-b) (10.0 mg, 0.0079 mmol) was converted to compound (1-24) as a colorless oil (5.0 mg, quant.). Analysis results of NMR spectrum and reaction scheme are shown below.

$^1$H NMR (400 MHz, CDCl$_3$:CD$_3$OD=10:1) δ 0.88 (t, J=6.7 Hz, 3H), 1.25-1.32 (m, 32H), 1.60-1.62 (m, 6H), 2.19 (t, J=6.7 Hz, 2H), 3.38-3.43 (m, 2H), 3.52-3.54 (m, 2H), 3.69-3.74 (m, 3H), 3.77-3.82 (m, 3H), 3.89 (dd, J=10.3, 4.0 Hz, 1H), 3.94-3.96 (m, 1H), 4.18-4.20 (m, 1H), 4.91 (d, J=3.1 Hz, 1H), 7.44 (dd, J=7.4, 7.4 Hz, 2H), 7.50 (t, J=7.4 Hz, 1H), 7.76 (d, J=7.4 Hz, 2H); $^{13}$C NMR (100 MHz, CDCl$_3$:CD$_3$OD=10:1) δ 13.9, 22.5, 25.5, 25.8, 26.6, 28.8 (2C), 28.9, 29.2 (3C), 29.5, 29.6 (5C), 29.7, 31.8, 32.4, 36.2, 39.8, 50.2, 61.8, 67.4, 68.7, 69.7, 70.1, 70.4, 72.0, 74.5, 99.5, 126.8 (2C), 128.4 (2C), 131.3, 134.3, 168.3, 174.2; HRMS (ESI-TOF) calcd C$_{40}$H$_{70}$N$_2$NaO$_{10}$: (M+Na)$^+$, 761.4923; found:(M+Na)$^+$, 761.4921.

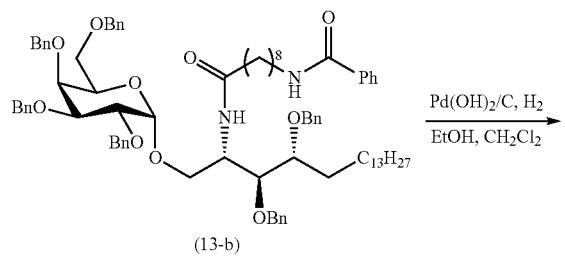

(13-b)

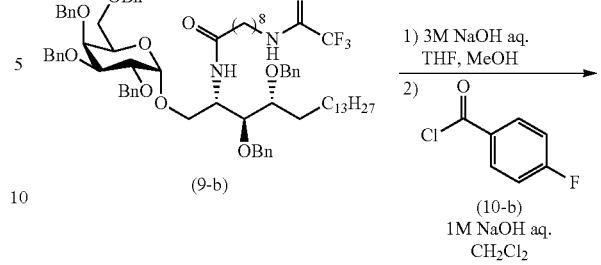

(9-b)

(10-b)
1M NaOH aq.
CH$_2$Cl$_2$

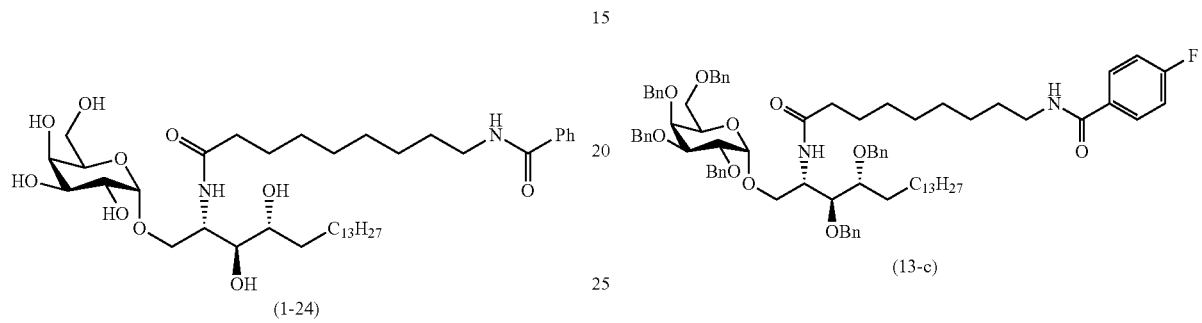

(1-24)            (13-c)

Synthesis Example 25

Synthesis of N-(9-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)amino)-9-oxononyl)-4-fluorobenzamide compound (13-c)

In the same manner as the synthesis method of compound (13-a) from compound (9-a) except that compound (9-b) was used instead of compound (9-a) and compound (10-b) was used instead of compound (10-a), compound (9-b) (10.0 mg, 0.0079 mmol) was converted to compound (13-c) as a colorless oil (5.1 mg, 50% yield). Analysis results of NMR spectrum and reaction scheme are shown below.

$^1$H NMR (400 MHz, CDCl$_3$) δ 0.88 (t, J=6.8 Hz, 3H), 1.23-1.28 (m, 34H), 1.48-1.65 (m, 4H), 1.90-1.96 (m, 2H), 3.38-3.42 (m, 3H), 3.48-3.50 (m, 2H), 3.73 (dd, J=10.9, 3.9 Hz, 1H), 3.84-3.88 (m, 2H), 3.88-3.94 (m, 2H), 4.01-4.04 (m, 2H), 4.15-4.18 (m, 1H), 4.36 (d, J=11.9 Hz, 1H), 4.42 (d, J=11.9 Hz, 1H), 4.46 (d, J=11.9 Hz, 1H), 4.51 (d, J=11.9 Hz, 1H), 4.55-4.58 (m, 2H), 4.64 (d, J=11.9 Hz, 1H), 4.71-4.81 (m, 4H), 4.84 (d, J=3.6 Hz, 1H), 4.91 (d, J=11.9 Hz, 1H), 5.99-6.02 (m, 1H), 6.15 (d, J=8.3 Hz, 1H), 7.08-7.10 (m, 2H), 7.21-7.35 (m, 30H), 7.74-7.76 (m, 2H); $^{13}$C NMR (100 MHz, CDCl$_3$) δ 14.1, 22.7, 25.5, 26.1, 26.9, 29.1, 29.2 (2C), 29.4, 29.6, 29.7 (7C), 29.8 (2C), 31.9, 36.5, 40.1, 50.3, 69.3, 69.5, 70.0, 71.7, 72.9, 73.4, 73.6 (2C), 74.7 (2C), 76.6, 78.6, 78.9, 80.1, 99.6, 115.5 (d, J$_{C-F}$=22.6 Hz, 2C), 127.4 (2C), 127.5 (3C), 127.7 (3C), 127.8 (6C), 127.9 (2C), 128.2 (2C), 128.3 (8C), 128.4 (4C), 129.1 (d, J$_{C-F}$=9.4 Hz, 2C), 130.9 (d, J$_{C-F}$=2.8 Hz), 137.5, 138.4 (2C), 138.6 (2C), 138.7, 164.6 (d, J$_{C-F}$=251.8 Hz), 166.4, 172.7: HRMS (ESI-TOF) calcd C$_{82}$H$_{105}$FN$_2$NaO$_{10}$: (M+Na)$^+$, 1319.7645; found: (M+Na)$^+$, 1319.7638.

Synthesis of N-(9-(((2S,3S,4R)-3,4-dihydroxy-1-(((2S,3R,4S,5S,6R)-3,4,5-trihydroxy-6-(hydroxymethyl)tetrahydro-2H-pyran-2-yl)oxy)octadecan-2-yl)amino)-9-oxononyl)-4-fluorobenzamide (Compound (1-25))

In the same manner as the synthesis method of compound (1-23) from compound (13-a) except that compound (13-c) was used instead of compound (13-a), compound (13-c) (5.0 mg, 0.0039 mmol) was converted to compound (1-25) as a white solid (3.6 mg, quant.). Analysis results of NMR spectrum and reaction scheme are shown below.

$^1$H NMR (400 MHz, CDCl$_3$:CD$_3$OD=10:1) δ 0.88 (t, J=6.8 Hz, 3H), 1.25-1.33 (m, 32H), 1.50-1.68 (m, 6H), 2.20 (t, J=7.3 Hz, 2H), 3.38-3.42 (m, 2H), 3.52-3.56 (m, 2H), 3.69-3.74 (m, 3H), 3.77-3.81 (m, 3H), 3.89 (dd, J=10.3, 3.6 Hz, 1H), 3.94-3.97 (m, 1H), 4.18-4.21 (m, 1H), 4.91 (d, J=3.6 Hz, 1H), 7.10-7.12 (m, 2H), 7.79-7.81 (m, 2H); $^{13}$C NMR (100 MHz, CDCl$_3$:CD$_3$OD=10:1) 13.9, 22.5, 24.5, 25.7, 26.6, 28.7, 28.8 (2C), 29.2 (2C), 29.5, 29.6 (6C), 31.8 (2C), 32.6, 36.2, 39.9, 50.2, 61.8, 67.4, 68.8, 69.6, 70.1, 70.5, 71.9, 74.7, 99.5, 115.4 (d, J$_{C-F}$=21.6 Hz, 2C), 129.2 (d, J$_{C-F}$=8.5 Hz, 2C), 130.5 (d, J$_{C-F}$=2.8 Hz), 164.5 (d, J$_{C-F}$=251.8 Hz), 167.1, 174.2: HRMS (ESI-TOF) calcd C$_{40}$H$_{69}$FN$_2$NaO$_{10}$: (M+Na)$^+$, 779.4828; found:(M+Na)$^+$, 779.4834.

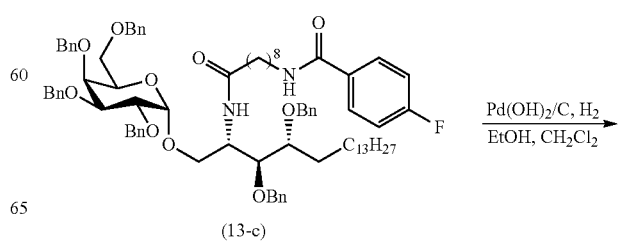

(13-c)

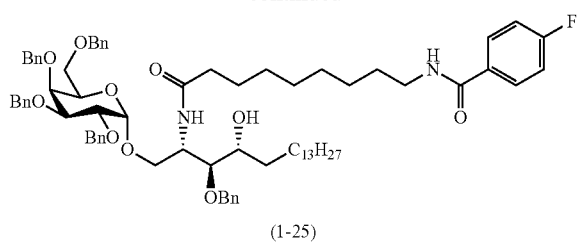

(1-25)

Synthesis Example 26

Synthesis of N-(9-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)amino)-9-oxononyl)-4-methoxybenzamide (Compound (13-d))

In the same manner as the synthesis method of compound (13-a) from compound (9-a) except that compound (9-b) was used instead of compound (9-a) and compound (10-c) was used instead of compound (10-a), compound (9-b) (10.0 mg, 0.0079 mmol) was converted to compound (13-d) as a colorless oil (5.1 mg, 71% yield). Analysis results of NMR spectrum and reaction scheme are shown below.

$^1$H NMR (400 MHz, CDCl$_3$) δ 0.88 (t, J=6.8 Hz, 3H), 1.26 (t, J=14.6 Hz, 34H), 1.48-1.61 (m, 4H), 1.90-1.96 (m, 2H), 3.38-3.41 (m, 3H), 3.48-3.50 (m, 2H), 3.73 (dd, J=11.0, 3.6 Hz, 1H), 3.83 (s, 3H), 3.84-3.88 (m, 2H), 3.89-3.94 (m, 2H), 4.01-4.04 (m, 2H), 4.15-4.18 (m, 1H), 4.36 (d, J=11.9 Hz, 1H), 4.42 (d, J=11.9 Hz, 1H), 4.47 (d, J=11.9 Hz, 1H), 4.51 (d, J=11.9 Hz, 1H), 4.55-4.58 (m, 2H), 4.64 (d, J=11.9 Hz, 1H), 4.71-4.81 (m, 4H), 4.85 (d, J=3.6 Hz, 1H), 4.91 (d, J=11.9 Hz, 1H), 5.96-5.99 (m, 1H), 6.15 (d, J=8.5 Hz, 1H), 6.91 (d, J=8.8 Hz, 2H), 7.21-7.37 (m, 30H), 7.71 (d, J=8.8 Hz, 2H); $^{13}$C NMR (100 MHz, CDCl$_3$) δ 14.1, 22.7, 25.5, 26.1, 26.9, 29.1, 29.2, 29.4, 29.7 (10C), 29.8, 31.9, 36.5, 39.9, 50.3, 55.4, 69.3, 69.5, 70.0, 71.7, 72.9, 73.4, 73.6 (2C), 74.7 (2C), 77.2, 78.6, 78.9, 80.1, 99.6, 113.7, 127.1 (2C), 127.4 (2C), 127.5 (3C), 127.7 (2C), 127.8 (5C), 127.9 (4C), 128.2 (2C), 128.3 (8C), 128.4 (4C), 128.6 (2C), 137.6, 138.4 (2C), 138.6 (2C), 138.7, 162.0, 166.9, 172.7; HRMS(ESI-TOF) calcd C$_{83}$H$_{108}$N$_2$NaO$_{11}$: (M+Na)$^+$, 1319.7645; found: (M+Na)$^+$, 1319.7638.

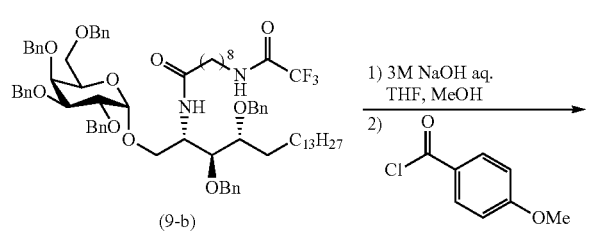

(9-b)

1) 3M NaOH aq. THF, MeOH

2) [acid chloride] (10-c)

1M NaOH aq. CH$_2$Cl$_2$

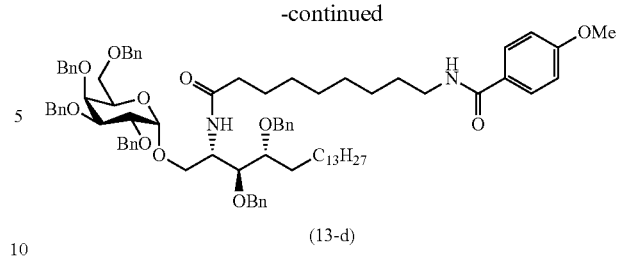

(13-d)

Synthesis of N-(9-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-9-oxononyl)-4-methoxybenzamide (Compound (1-26))

In the same manner as the synthesis method of compound (1-23) from compound (13-a) except that compound (13-d) was used instead of compound (13-a), compound (13-d) (5.0 mg, 0.0039 mmol) was converted to compound (1-26) as a white solid (4.1 mg, quant.). Analysis results of NMR spectrum and reaction scheme are shown below.

$^1$H NMR (400 MHz, CDCl$_3$:CD$_3$OD=10:1) δ 0.88 (t, J=6.6 Hz, 3H), 1.25-1.33 (m, 32H), 1.58-1.65 (m, 6H), 2.19-2.26 (m, 2H), 3.38-3.41 (m, 2H), 3.53-3.56 (m, 2H), 3.72-3.86 (m, 6H), 3.86 (s, 3H), 3.86-3.91 (m, 1H), 3.95-3.98 (m, 1H), 4.19-4.21 (m, 1H), 4.91-4.93 (m, 1H), 6.93 (d, J=8.1 Hz, 2H), 7.74 (d, J=8.1 Hz, 2H); $^{13}$C NMR (100 MHz, CDCl$_3$) δ 13.9, 22.5, 25.5, 25.7, 26.6, 28.8, 28.9, 29.2 (2C), 29.3, 29.5, 29.6 (4C), 29.7, 31.8 (2C), 32.5, 35.2, 36.4, 39.8, 50.2, 55.3, 62.0, 67.5, 68.8, 70.4, 70.5, 71.2, 72.0, 74.7, 99.5, 113.6 (2C), 126.5, 128.7 (2C), 162.0, 164.7, 175.8: HRMS (ESI-TOF) calcd C$_{41}$H$_{72}$N$_2$NaO$_{11}$: (M+Na)$^+$, 791.5028; found: (M+Na)$^+$, 791.5034.

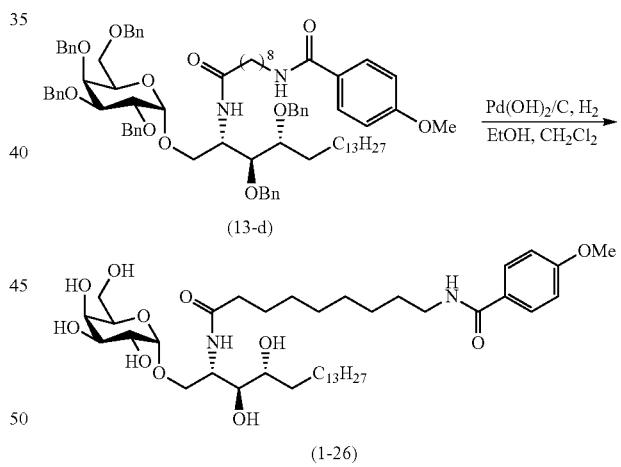

(13-d)

Pd(OH)$_2$/C, H$_2$
EtOH, CH$_2$Cl$_2$ (1-26)

Synthesis Example 27

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-12-undecanamidedodecanamide (Compound (102C-085a))

In the same manner as the synthesis method of compound (1-1) from compound (4-a), amide (4-a) (16.0 mg, 0.012 mmol) was converted to compound (102C-085a) as a white solid (6.1 mg, 61% yield). Analysis results of HRMS spectrum and reaction scheme are shown below.

HRMS(ESI-TOF) calcd C$_{47}$H$_{92}$N$_2$NaO$_{10}$: (M+Na)$^+$, 867.6644; found: (M+Na)$^+$, 867.6634.

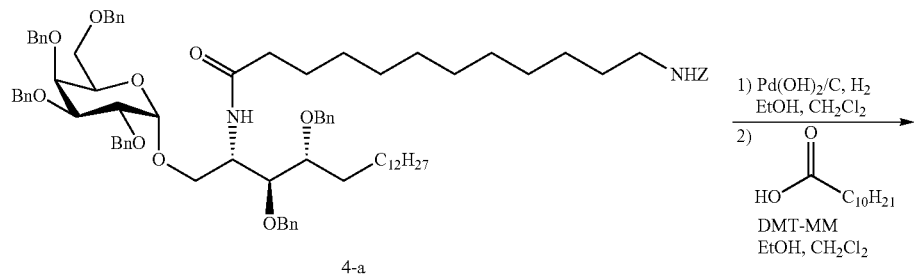

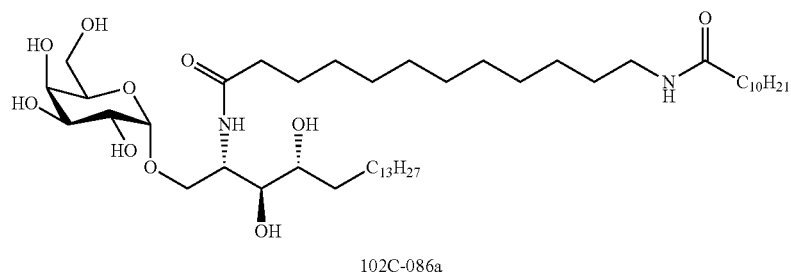

102C-086a

Synthesis Example 28

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-12-nonanamidedodecanamide (Compound (102C-086a))

In the same manner as the synthesis method of compound (1-1) from compound (4-a), amide (4-a) (16.0 mg, 0.012 mmol) was converted to compound (102C-086a) as a white solid (4.8 mg, 50% yield). Analysis results of HRMS spectrum and reaction scheme are shown below.
HRMS(ESI-TOF) calcd $C_{45}H_{88}N_2NaO_{10}$: (M+Na)$^+$, 839.6331; found:(M+Na)$^+$, 839.6327.

Synthesis Example 29

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-12-pentanamidedodecanamide (Compound (102C-087a))

In the same manner as the synthesis method of compound (1-1) from compound (4-a), amide (4-a) (16.0 mg, 0.012 mmol) was converted to compound (102C-087a) as a white solid (3.0 mg, 33% yield). Analysis results of HRMS spectrum and reaction scheme are shown below.
HRMS(ESI-TOF) calcd $C_{41}H_{80}N_2NaO_{10}$: (M+Na)$^+$, 783.5705; found: (M+Na)$^+$, 783.5705.

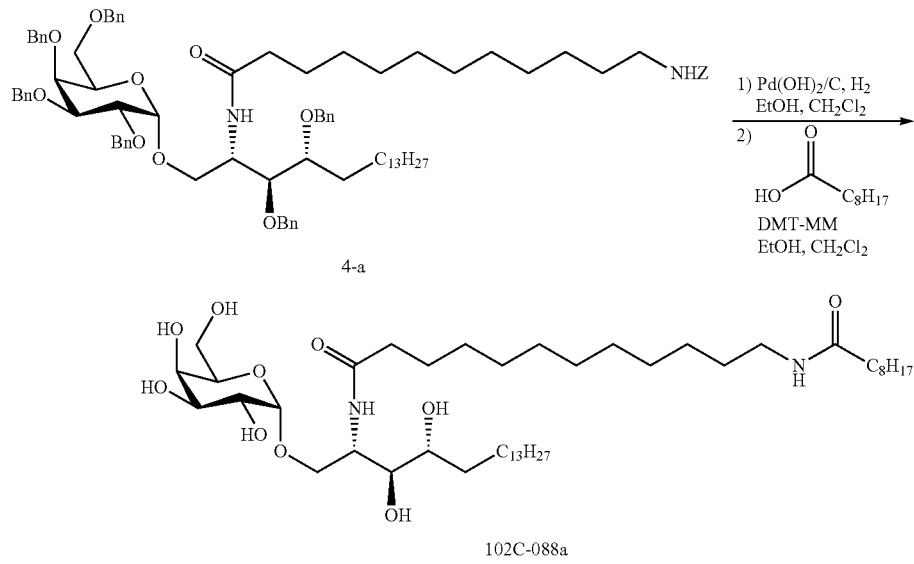

102C-088a

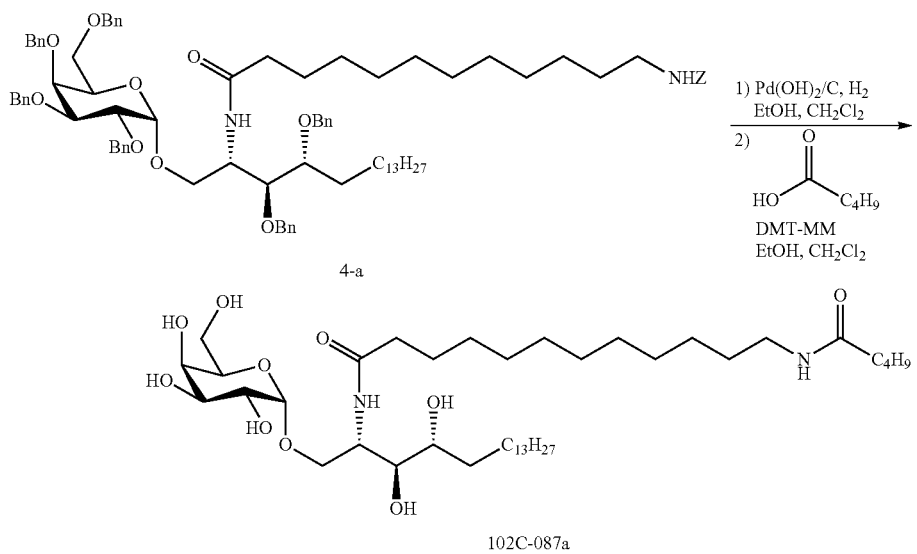

Synthesis Example 30

Synthesis of N-((2S,3S,4R)-3,4-dihydroxy-1-(((2S, 3R,4S,5R,6R)-3,4,5-trihydroxy-6-(hydroxymethyl) tetrahydro-2H-pyran-2-yl)oxy)octadecan-2-yl)-12-propionamidedodecanamide (Compound (102C-088a))

In the same manner as the synthesis method of compound (1-1) from compound (4-a), amide (4-a) (16.0 mg, 0.012 mmol) was converted to compound (102C-088a) as a white solid (4.0 mg, 46% yield). Analysis results of HRMS spectrum and reaction scheme are shown below.

HRMS (ESI-TOF) calcd $C_{39}H_{76}N_2NaO_{10}$: (M+Na)$^+$, 755.5392; found: (M+Na)$^+$, 755.5392.

Synthesis Example 31

Synthesis of N-(12-{[(2S,3S,4R)-3,4-bis(benzyloxy)-1-{[(2S,3R,4S,5S,6R)-3,4,5-tris(benzyloxy)-6-[(benzyloxy)methyl]tetrahydro-2H-pyran-2-yl]oxy}octadecan-2-yl]amino}-12-oxododecyl)-4-fluorobenzamide (Compound (303B-053))

A mixture of compound (203B-026) (20.9 mg, 0.0159 mmol) and 4M HCl in dioxane (0.12 mL) was stirred at room temperature. After stirring for 1.5 hr, the obtained mixture was concentrated under reduced pressure, and azeotroped three times with toluene. The obtained residue was dissolved in 1M NaOH aqueous solution (0.4 mL) and CH$_2$Cl$_2$ (0.4 mL). 4-Fluorobenzoyl chloride (19 µL, 0.0159

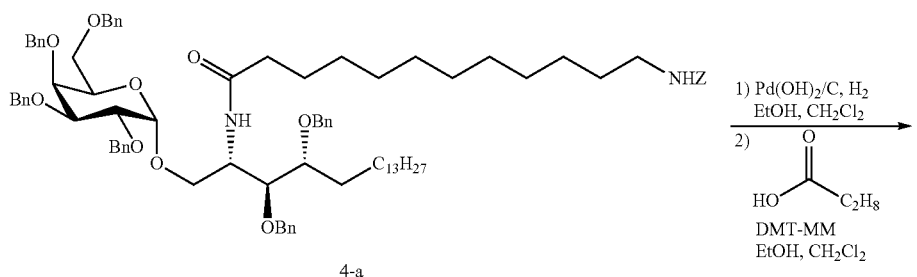

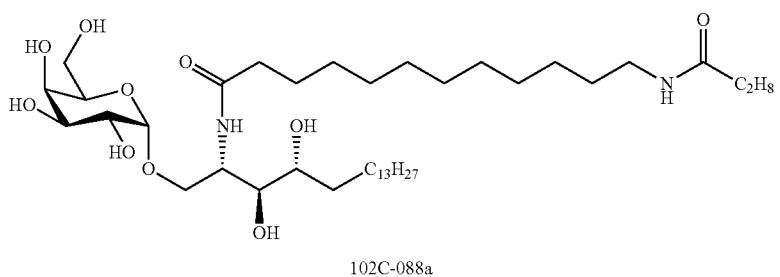

mmol) was added to the stirred mixture at room temperature. The obtained mixture was stirred at this temperature for 1 hr, and diluted with saturated NaHCO$_3$ aqueous solution. The obtained diluted product was extracted with EtOAc. The obtained extract was washed with saturated NaHCO$_3$ aqueous solution, brine, and dried over NaSO$_4$, and concentrated under reduced pressure to give an oily residue, which was purified by flash chromatography over silica gel with n-hexane-EtOAc (2:1) to give compound (303B-053) as a colorless oil (17.5 mg, 82% yield). Analysis results of LRMS spectrum and reaction scheme are shown below.

LRMS (ESI-TOF) calc C$_{85}$H$_{111}$FN$_2$NaO$_{10}$: (M+Na)$^+$, 1361.81; found: (M+Na)$^+$, 1361.81.

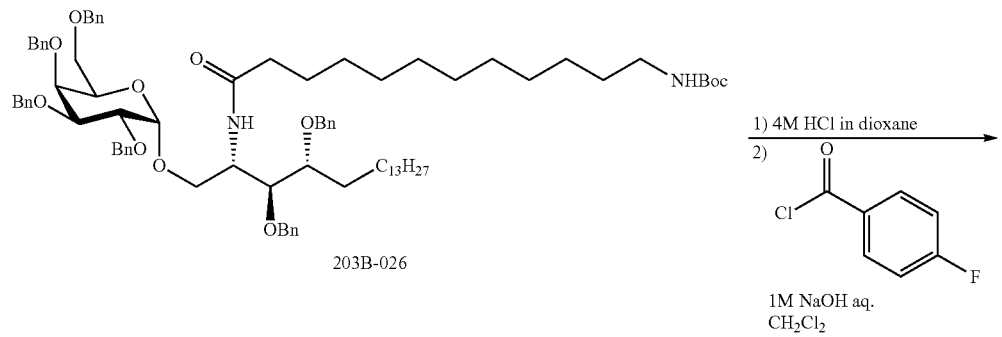

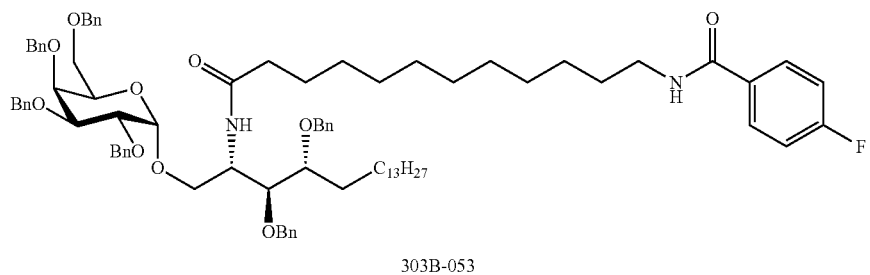

Synthesis Example 32

Synthesis of N-(12-{[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]amino}-12-oxododecyl)-4-fluorobenzamide (Compound (303B-068))

In the same manner as the synthesis method of compound (1-23) from compound (13-a), compound (303B-053) (8.7 mg, 0.0065 mmol) was converted to compound (303B-068) as a white solid (5.8 mg, quant.). Analysis results of LRMS spectrum and reaction scheme are shown below.

LRMS (ESI-TOF) calc C$_{43}$H$_{75}$FN$_2$NaO$_{10}$: (M+Na)$^+$, 821.53; found: (M+Na)$^+$, 821.4901.

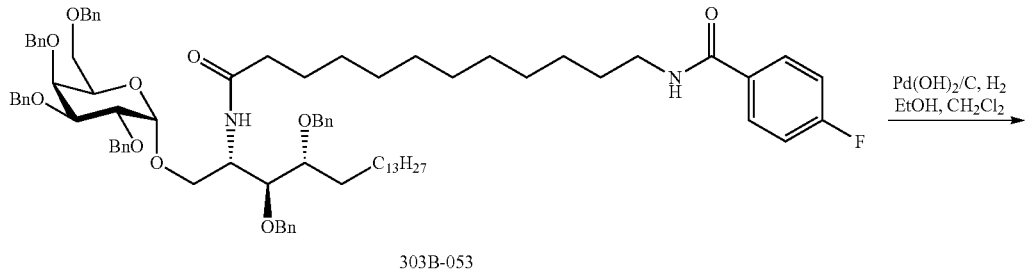

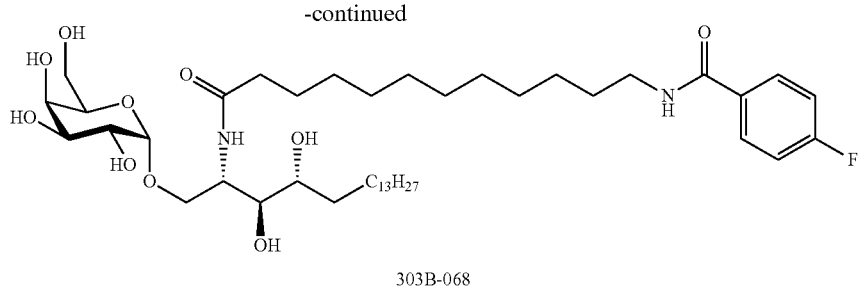

303B-068

Synthesis Example 33

Synthesis of N-(12-{[(2S,3S,4R)-3,4-bis(benzyloxy)-1-{[(2S,3R,4S,5S,6R)-3,4,5-tris(benzyloxy)-6-[(benzyloxy)methyl]tetrahydro-2H-pyran-2-yl]oxy}octadecan-2-yl]amino}-12-oxododecyl)-4-methoxybenzamide (Compound 303B-055)

In the same manner as the synthesis method of compound (303B-053) from compound (203B-026), amine (203B-026) (20.7 mg, 0.0157 mmol) was converted to compound (303B-055) as a white solid (16.7 mg, 79% yield). Analysis results of LRMS spectrum and reaction scheme are shown below. LRMS (ESI-TOF) calc $C_{86}H_{114}N_2NaO_{11}$: $(M+Na)^+$, 1373.83; found: $(M+Na)^+$, 1373.84.

Synthesis Example 34

[N-(12-{[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]amino}-12-oxododecyl)-4-methoxybenzamide (303B-070)

In the same manner as the synthesis method of compound (1-23) from compound (13-a), amide (303B-055) (6.6 mg, 0.0049 mmol) was converted to compound (303B-070) as a white solid (4.7 mg, quant.). Analysis results of LRMS spectrum and reaction scheme are shown below. LRMS (ESI-TOF) calc $C_{44}H_{78}N_2NaO_{11}$: $(M+Na)^+$, 833.55; found: $(M+Na)^+$, 833.4810.

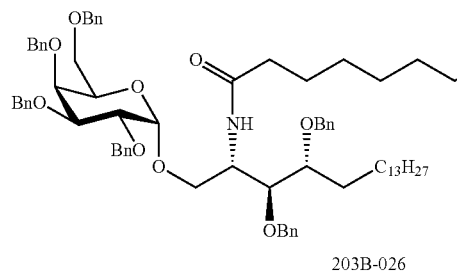

203B-026

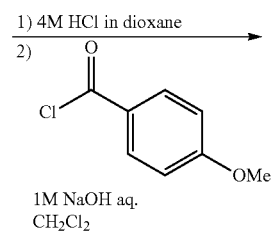

1) 4M HCl in dioxane
2)
1M NaOH aq.
CH$_2$Cl$_2$

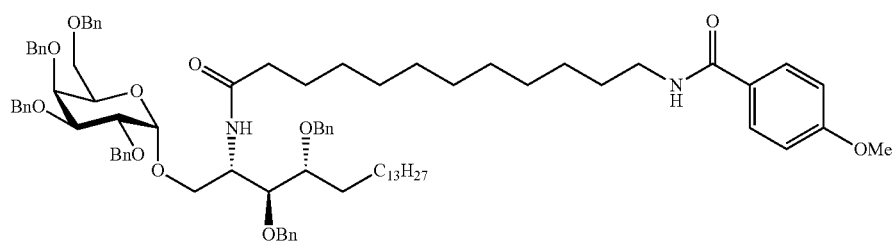

303B-055

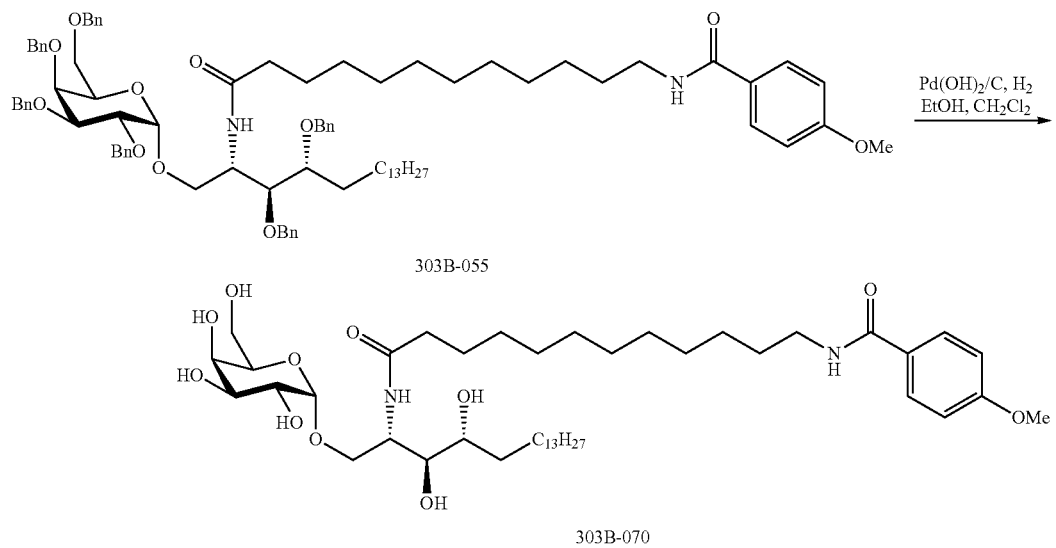

Synthesis Example 35

Synthesis of N-(12-{[(2S,3S,4R)-3,4-bis(benzyloxy)-1-{[(2S,3R,4S,5S,6R)-3,4,5-tris(benzyloxy)-6-[(benzyloxy)methyl]tetrahydro-2H-pyran-2-yl]oxy}octadecan-2-yl]amino}-12-oxododecyl)-2-fluorobenzamide (Compound (303B-051))

A mixture of compound (203D-026) (26.3 mg, 0.0200 mmol) and 4M HCl in dioxane (0.15 mL) was stirred at room temperature. After stirring for 1.5 hr, the obtained mixture was concentrated under reduced pressure, and azeotroped three times with toluene. The obtained residue and 2-fluorobenzoic acid (8.4 mg, 0.0600 mmol) was dissolved in $CH_2Cl_2$ (0.2 mL). HOBt (8.1 mg, 0.0600 mmol), WSC·HCl (11.5 mg, 0.0600 mmol) and DIPEA (10 µL, 0.0720 mmol) were added to the stirred mixture at 0° C. The obtained mixture was stirred at the same temperature for 22.5 hr, and diluted with saturated $NaHCO_3$ aqueous solution. The obtained diluted product was extracted with $CH_2Cl_2$. The obtained extract was washed with saturated $NaHCO_3$ aqueous solution, brine, and dried over $Na_2SO_4$, and concentrated under reduced pressure to give an oily residue, which was purified by flash chromatography over silica gel with n-hexane-EtOAc (2:1) to give compound (303B-051) as a colorless oil (18.0 mg, 67% yield). Analysis results of LRMS spectrum and reaction scheme are shown below.

LRMS (ESI-TOF) calc $C_{85}H_{111}FN_2NaO_{10}$: (M+Na)$^+$, 1361.81; found: (M+Na)$^+$, 1361.81.

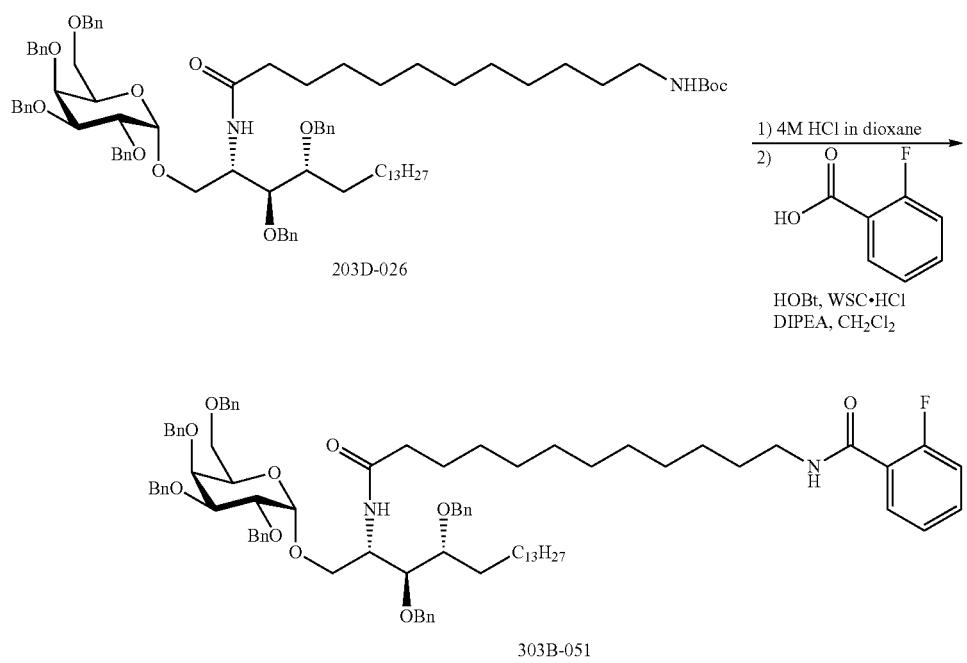

Synthesis Example 36

Synthesis of N-(12-{[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]amino}-12-oxododecyl)-2-fluorobenzamide (Compound (303B-069))

In the same manner as the synthesis method of compound (1-23) from compound (13-a), amide (303B-051) (8.4 mg, 0.0062 mmol) was converted to compound (303B-069) as a colorless oil (4.2 mg, 83% yield). Analysis results of LRMS spectrum and reaction scheme are shown below.
LRMS (ESI-TOF) calc $C_{43}H_{75}FN_2NaO_{10}$: $(M+Na)^+$, 821.53; found: $(M+Na)^+$, 821.47.

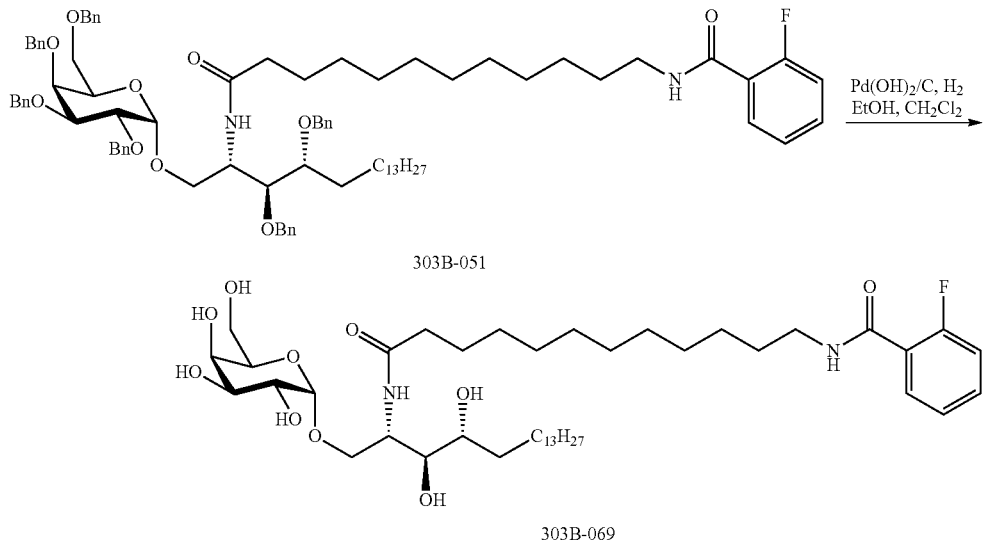

Synthesis Example 37

Synthesis of N-(12-{[(2S,3S,4R)-3,4-bis(benzyloxy)-]-1-[(2S,3R,4S,5S,6R)-3,4,5-tris(benzyloxy)-6-[(benzyloxy)methyl]tetrahydro-2H-pyran-2-yl]oxy}octadecan-2-yl]amino}-12-oxododecyl)cyclohexanecarboxamide (Compound (303B-057))

In the same manner as the synthesis method of compound (1-23) from compound (13-a), amine (203D-026) (21.8 mg, 0.0166 mmol) was converted to compound (303B-057) as a white solid (13.6 mg, 62% yield). Analysis results of LRMS spectrum and reaction scheme are shown below.
LRMS (ESI-TOF) calc $C_{85}H_{118}N_2NaO_{10}$: $(M+Na)^+$, 1349.87; found: $(M+Na)^+$, 1349.87.

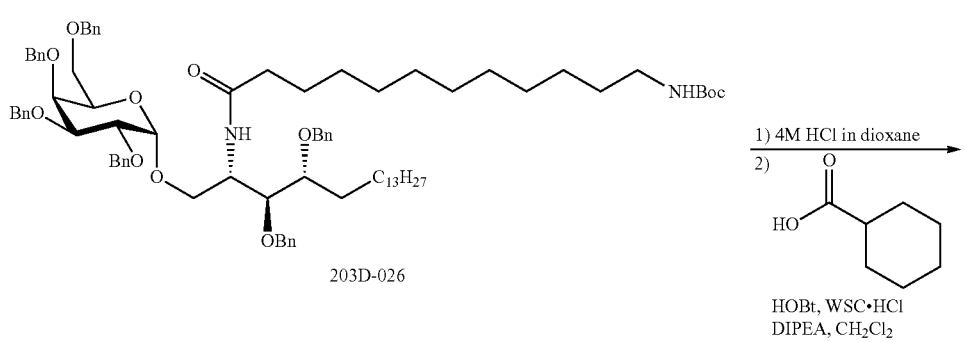

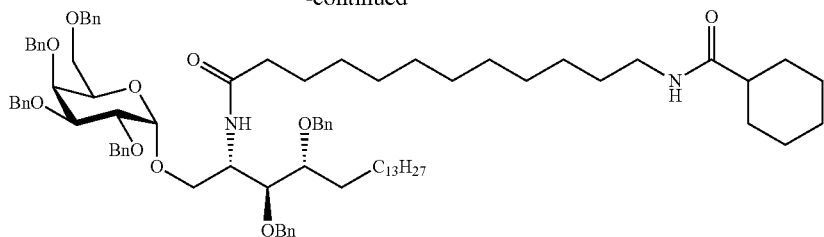

303B-057

Synthesis Example 38

Synthesis of N-(12-{[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]amino}-12-oxododecyl)cyclohexanecarboxamide (Compound (303B-071))

In the same manner as the synthesis method of compound (1-23) from compound (13-a), amide (303B-057) (6.8 mg, 0.0052 mmol) was converted to compound (303B-071) as a white solid (3.1 mg, 77% yield). Analysis results of LRMS spectrum and reaction scheme are shown below.
LRMS (ESI-TOF) calc $C_{43}H_{82}N_2NaO_{10}$: (M+Na)$^+$, 809.59; found: (M+Na)$^+$, 809.5014.

Synthesis Example 39

Synthesis of N-(12-{[(2S,3S,4R)-3,4-bis(benzyloxy)-1-{[(2S,3R,4S,5S,6R)-3,4,5-tris(benzyloxy)-6-[(benzyloxy)methyl]tetrahydro-2H-pyran-2-yl]oxy}octadecan-2-yl]amino}-12-oxododecyl)-3-fluorobenzamide (Compound (303B-066))

In the same manner as the synthesis method of compound (303B-051) from compound (203D-026), amine (203D-026) (20.9 mg, 0.0159 mmol) was converted to compound (303B-066) as a colorless oil (17.0 mg, 80% yield). Analysis results of LRMS spectrum and reaction scheme are shown below.
LRMS (ESI-TOF) calc $C_{85}H_{111}FN_2NaO_{10}$: (M+Na)$^+$, 1361.81; found: (M+Na)$^+$, 1361.84.

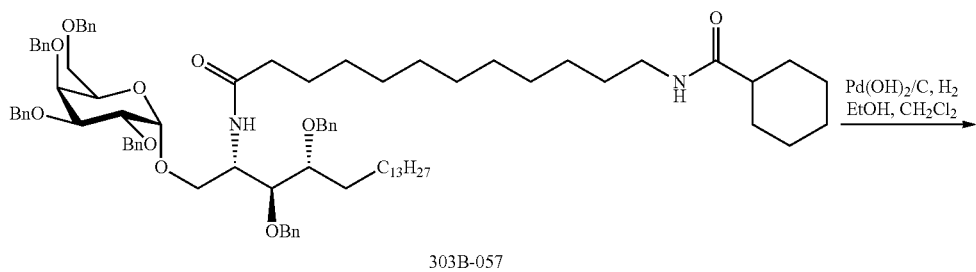

303B-057

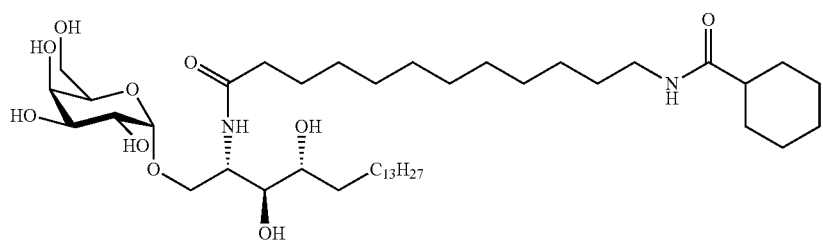

303B-071

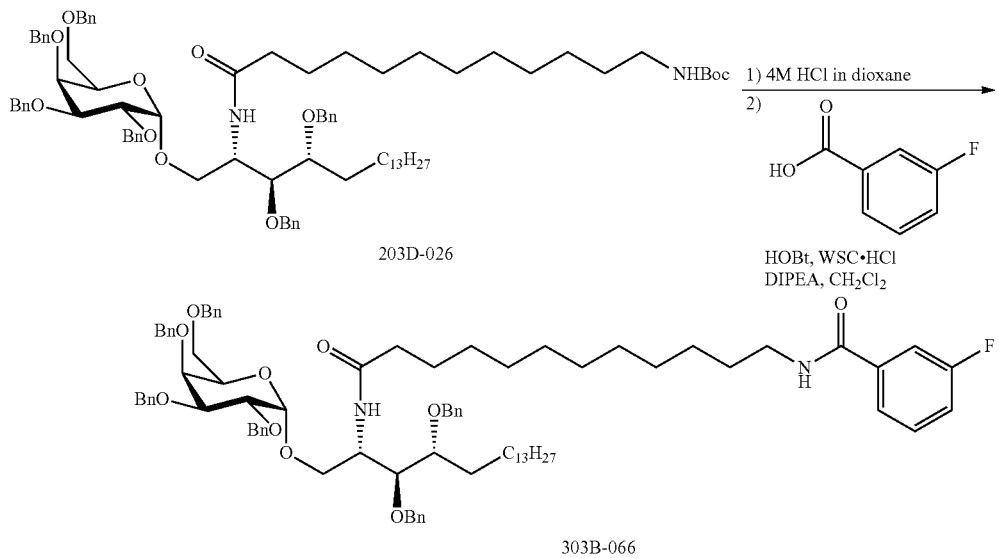

203D-026

303B-066

Synthesis Example 40

Synthesis of N-(12-{[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]amino}-12-oxododecyl)-3-fluorobenzamide (Compound (303B-077))

In the same manner as the synthesis method of compound (1-23) from compound (13-a), amide (303B-066) (10.4 mg, 0.0078 mmol) was converted to compound (303B-077) as a colorless oil (5.4 mg, 87% yield). Analysis results of LRMS spectrum and reaction scheme are shown below.
LRMS(ESI-TOF) calc $C_{43}H_{75}FN_2NaO_{10}$:(M+Na)$^+$, 821.53; found: (M+Na)$^+$, 821.51.

Synthesis Example 41

Synthesis of N-(12-{[(2S,3S,4R)-3,4-bis(benzyloxy)-1-{[(2S,3R,4S,5S,6R)-3,4,5-tris(benzyloxy)-6-[(benzyloxy)methyl]tetrahydro-2H-pyran-2-yl]oxy}octadecan-2-yl]amino}-12-oxododecyl)-2-methoxybenzamide (Compound (303B-064))

In the same manner as the synthesis method of compound (303B-051) from compound (203D-026), amine (203D-026) (20.4 mg, 0.0155 mmol) was converted to the compound (303B-066) as a colorless oil (16.4 mg, 78% yield). Analysis results of LRMS spectrum and reaction scheme are shown below.
LRMS (ESI-TOF) calc $C_{86}H_{114}N_2NaO_{11}$: (M+Na)$^+$, 1373.83; found: (M+Na)$^+$, 1373.88.

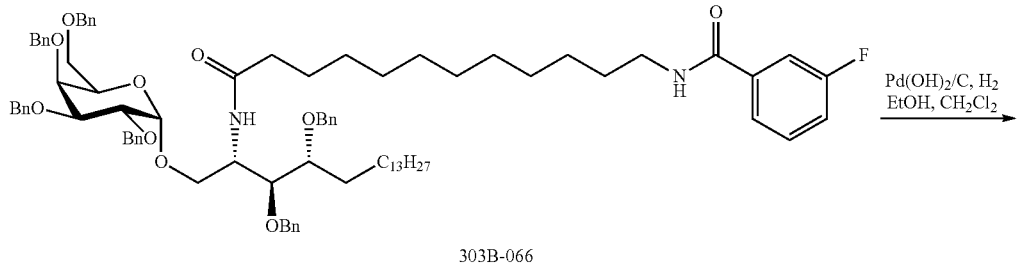

303B-066

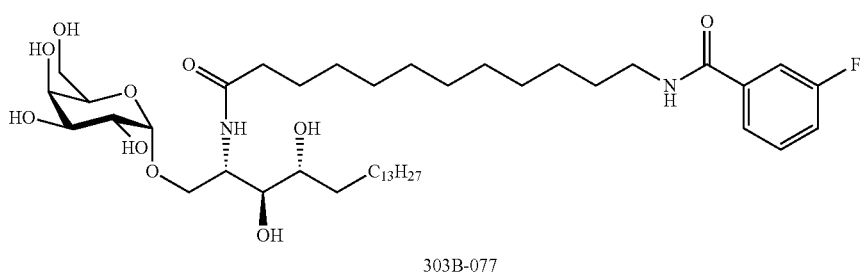

303B-077

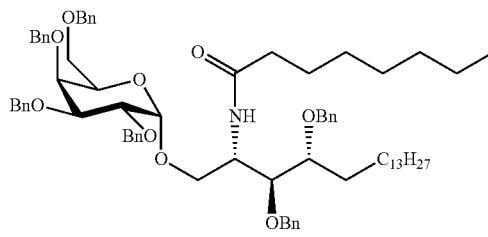

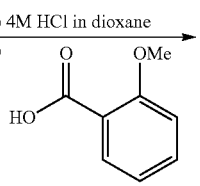

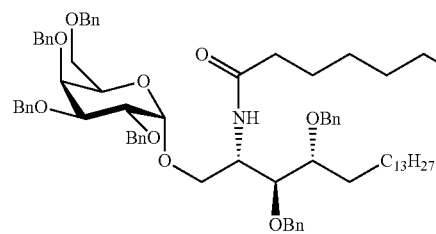

Synthesis Example 42

Synthesis of N-(12-{[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]amino}-12-oxododecyl)-2-methoxybenzamide (Compound (303B-081))

In the same manner as the synthesis method of compound (1-23) from compound (13-a), amide (303B-064) (8.9 mg, 0.0066 mmol) was converted to the compound (303B-081) as a colorless oil (5.0 mg, 94% yield). Analysis results of LRMS spectrum and reaction scheme are shown below.
LRMS(ESI-TOF) calc $C_{44}H_{78}N_2NaO_{11}$: (M+Na)$^+$, 833.55; found: (M+Na)$^+$, 833.57.

Synthesis Example 43

Synthesis of N-(12-{[(2S,3S,4R)-3,4-bis(benzyloxy)-1-{[(2S,3R,4S,5S,6R)-3,4,5-tris(benzyloxy)-6-[(benzyloxy)methyl]tetrahydro-2H-pyran-2-yl]oxy}octadecan-2-yl]amino}-12-oxododecyl)-3-methoxybenzamide (Compound (303B-073))

In the same manner as the synthesis method of compound (303B-051) from compound (203D-026), amine (203D-026) (20.2 mg, 0.0153 mmol) was converted to the compound (303B-073) as a colorless oil (17.8 mg, 86% yield). Analysis results of LRMS spectrum and reaction scheme are shown below.
LRMS(ESI-TOF) calc $C_{86}H_{114}N_2NaO_{11}$: (M+Na)$^+$, 1373.83; found: (M+Na)$^+$, 1373.86.

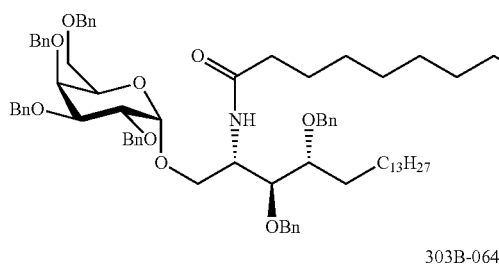

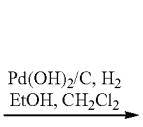

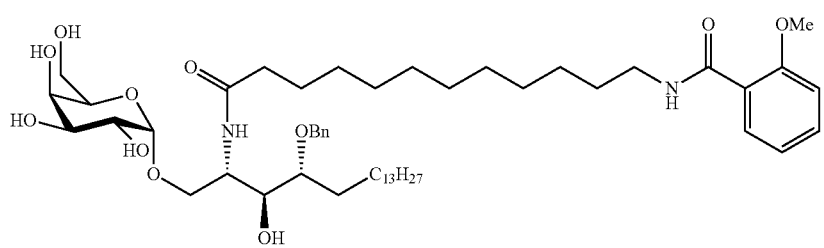

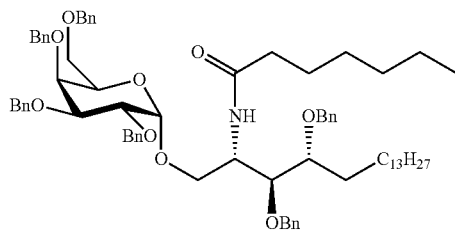

203D-026

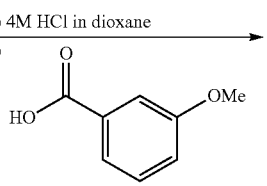

HOBt, WSC·HCl
DIPEA, CH$_2$Cl$_2$

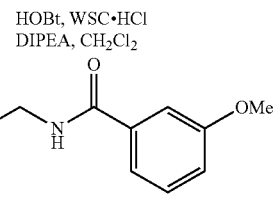

303B-073

Synthesis Example 44

Synthesis of N-(12-{[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]amino}-12-oxododecyl)-3-methoxybenzamide (Compound (303B-082))

In the same manner as the synthesis method of compound (1-23) from compound (13-a), amide (303B-073) (8.0 mg, 0.0059 mmol) was converted to compound (303B-082) as a colorless oil (4.8 mg, quant.). Analysis results of LRMS spectrum and reaction scheme are shown below.
LRMS(ESI-TOF) calc C$_{44}$H$_{78}$N$_2$NaO$_{11}$: (M+Na)$^+$, 833.55; found: (M+Na)$^+$, 833.56.

Synthesis Example 45

Synthesis of N-[(2S,3S,4R)-3,4-bis(benzyloxy)-1-{[(2S,3R,4S,5S,6R)-3,4,5-tris(benzyloxy)-6-[(benzyloxy)methyl]tetrahydro-2H-pyran-2-yl]oxy}octadecan-2-yl]-12-pivalamidedodecanamide (Compound (303B-059))

In the same manner as the synthesis method of compound (303B-051) from compound (203D-026), amine (203D-026) (21.6 mg, 0.0164 mmol) was converted to compound (303B-059) as a white solid (14.0 mg, 67% yield). Analysis results of LRMS spectrum and reaction scheme are shown below.
LRMS(ESI-TOF) calc C$_{83}$H$_{116}$N$_2$NaO$_{10}$: (M+Na)$^+$, 1323.85; found: (M+Na)$^+$, 1323.90.

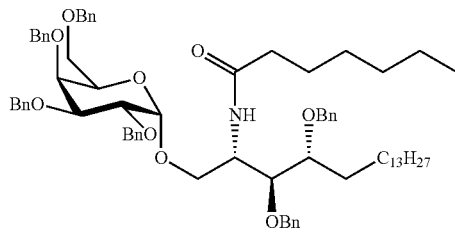

303B-073

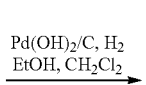

Pd(OH)$_2$/C, H$_2$
EtOH, CH$_2$Cl$_2$

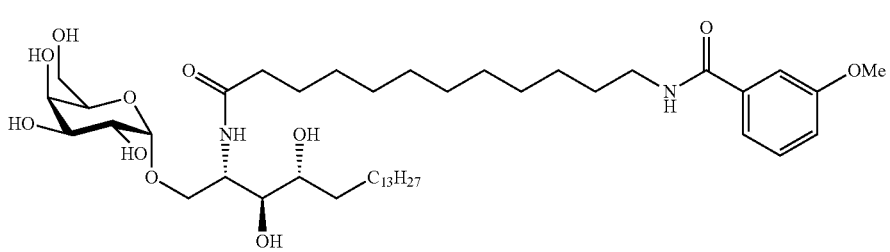

303B-082

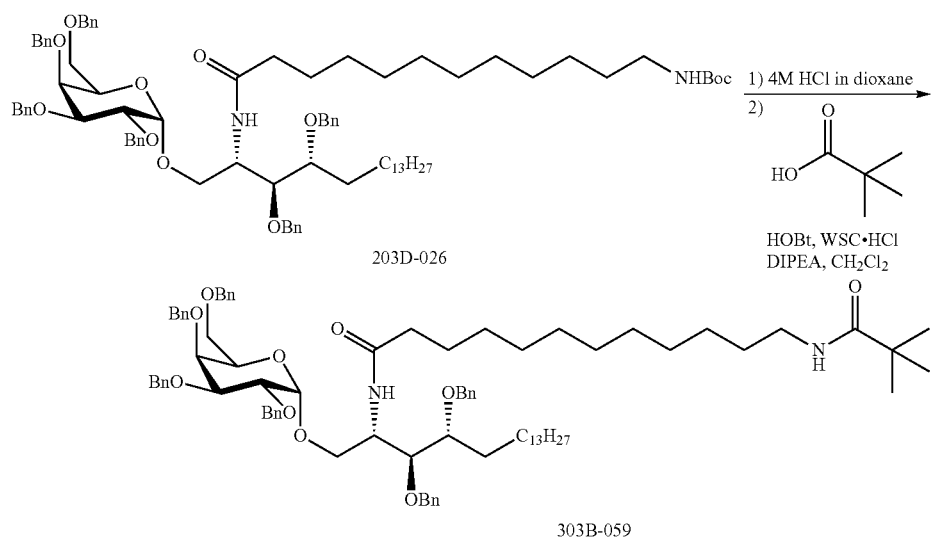

Synthesis Example 46

Synthesis of N-[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]-12-pivalamidedodecanamide (Compound (303B-072))

In the same manner as the synthesis method of compound (1-23) from compound (13-a), amide (303B-059) (6.9 mg, 0.0053 mmol) was converted to compound (303B-072) as a colorless oil (4.1 mg, quant.). Analysis results of LRMS spectrum and reaction scheme are shown below.
LRMS(ESI-TOF) calc $C_{41}H_{80}N_2NaO_{10}$:(M+Na)$^+$, 783.57; found:(M+Na)$^+$, 783.57.

Synthesis Example 47

Synthesis of N-(12-{[(2S,3S,4R)-3,4-bis(benzyloxy)-1-{[(2S,3R,4S,5S,6R)-3,4,5-tris(benzyloxy)-6-[(benzyloxy)methyl]tetrahydro-2H-pyran-2-yl]oxy}octadecan-2-yl]amino}-12-oxododecyl)isonicotinamide (Compound (303B-060))

In the same manner as the synthesis method of compound (303B-051) from compound (203D-026), amine (203D-026) (23.1 mg, 0.0175 mmol) was converted to compound (303B-060) as a colorless oil (17.2 mg, 74% yield). Analysis results of LRMS spectrum and reaction scheme are shown below.
LRMS(ESI-TOF) calc $C_{84}H_{111}N_3NaO_{10}$: (M+Na)$^+$, 1344.82; found: (M+Na)$^+$, 1344.85.

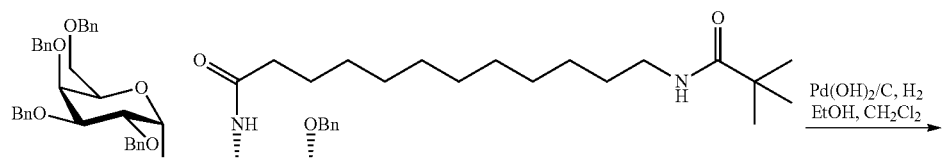

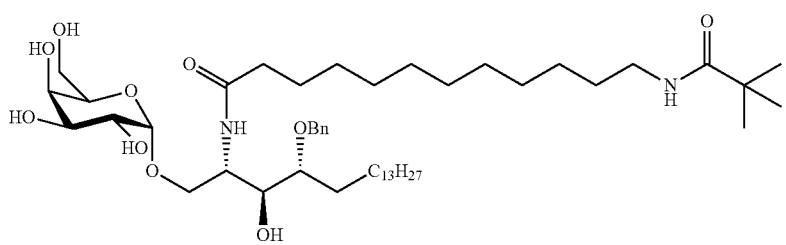

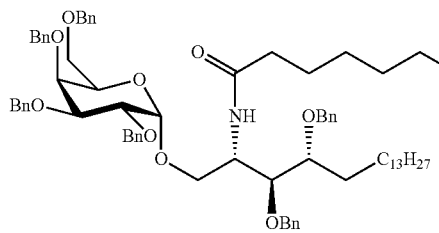
203D-026

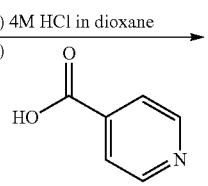

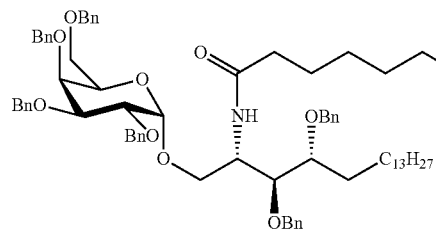
303B-060

Synthesis Example 48

Synthesis of N-(12-{[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]amino}-12-oxododecyl)piperidine-4-carboxamide (Compound (303B-78))

In the same manner as the synthesis method of compound (1-23) from compound (13-a), amide (303B-060) (7.7 mg, 0.0058 mmol) was converted to compound (303B-078) as a colorless oil (5.7 mg, quant.). Analysis results of LRMS spectrum and reaction scheme are shown below.
LRMS(ESI-TOF) calc $C_{42}H_{82}N_3NaO_{10}$:(M+Na)$^+$, 788.60; found: (M+Na)$^+$, 788.60.

Synthesis Example 49

Synthesis of N-(12-{[(2S,3S,4R)-3,4-bis(benzyloxy)-1-{[(2S,3R,4S,5S,6R)-3,4,5-tris(benzyloxy)-6-[(benzyloxy)methyl]tetrahydro-2H-pyran-2-yl]oxy}octadecan-2-yl]amino}-12-oxododecyl)-[1,1'-biphenyl]-4-carboxamide (Compound (303B-062))

In the same manner as the synthesis method of compound (303B-051) from compound (203D-026), amine (203D-026) (19.7 mg, 0.0149 mmol) was converted to compound (303B-062) as a colorless oil (15.0 mg, 72% yield). Analysis results of LRMS spectrum and reaction scheme are shown below.
LRMS(ESI-TOF) calc $C_{91}H_{116}N_2NaO_{10}$: (M+Na)$^+$, 1419.85; found: (M+Na)$^+$, 1419.84.

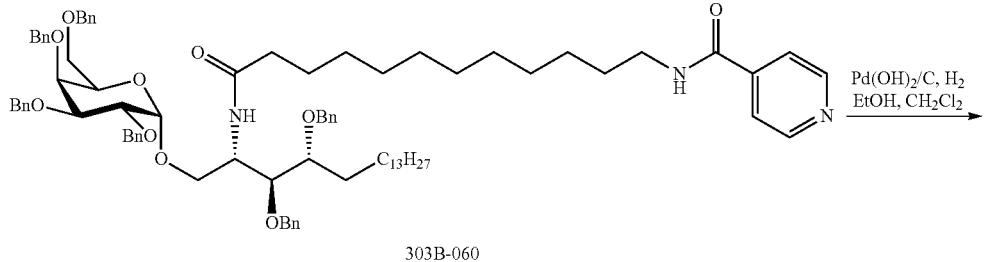
303B-060

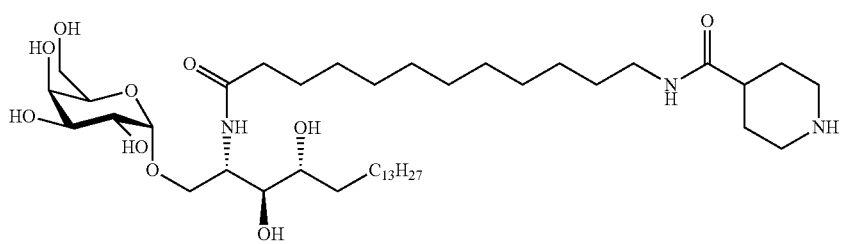
303B-078

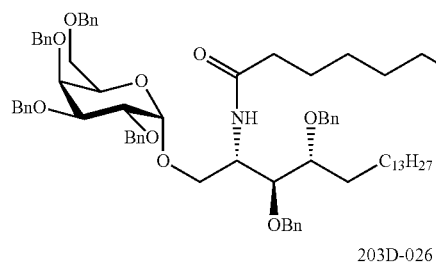
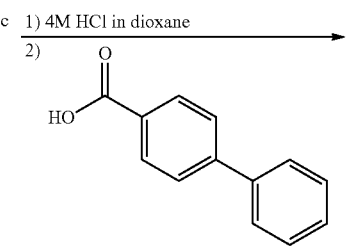

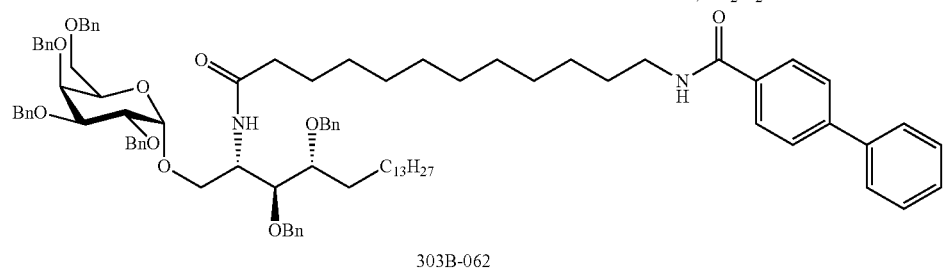

Synthesis Example 50

Synthesis of N-(12-{[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]amino}-12-oxododecyl)-[1,1'-biphenyl]-4-carboxamide (Compound (303B-083))

In the same manner as the synthesis method of compound (1-23) from compound (13-a), amide (303B-062) (8.0 mg, 0.0057 mmol) was converted to compound (303B-083) as a colorless oil (4.9 mg, quant.). Analysis results of LRMS spectrum and reaction scheme are shown below.
LRMS(ESI-TOF) calc $C_{49}H_{80}N_2NaO_{10}$: $(M+Na)^+$, 879.57; found: $(M+Na)^+$, 879.58.

Synthesis Example 51

Synthesis of N-[(2S,3S,4R)-3,4-bis(benzyloxy)-1-({(2S,3R,4S,5S,6R)-3,4,5-tris(benzyloxy)-6-[(benzyloxy)methyl]tetrahydro-2H-pyran-2-yl}oxy)octadecan-2-yl]-12-(3-pentylureido)dodecanamide (Compound (203D-092))

A mixture of compound (203D-026) (20.6 mg, 0.0156 mmol) in TFA/$CH_2Cl_2$=1/1 (114 μL) was stirred at room temperature. After stirring for 7 hr, the obtained mixture was diluted with $CH_2Cl_2$. The obtained diluted product was washed with saturated aqueous $NaHCO_3$, $H_2O$ and brine, dried over $Na_2SO_4$, and concentrated under reduced pressure to give a crude amine. The obtained amine was dis-

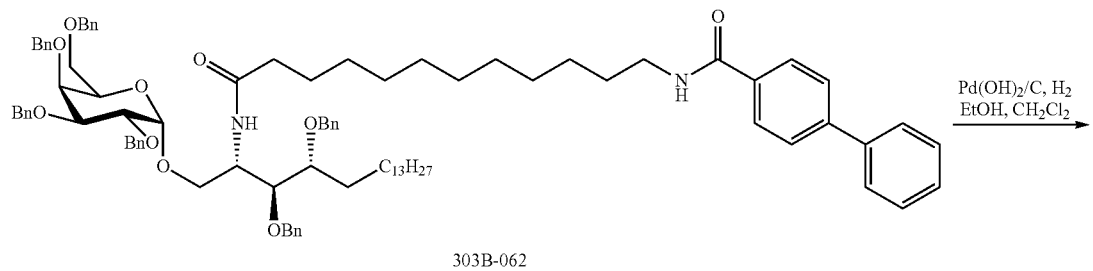

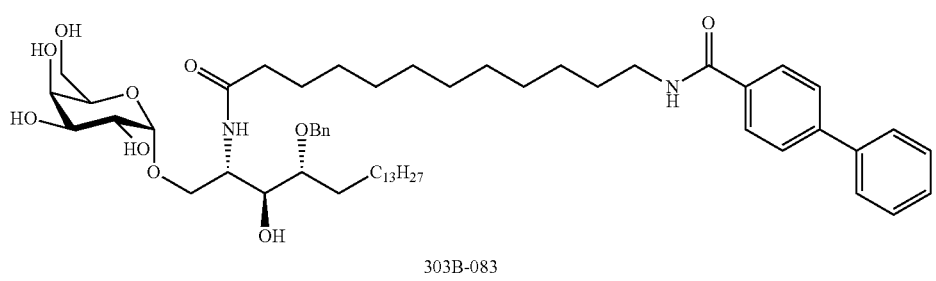

solved in toluene (220 μL). Isocyanate (0.172 mmol) in toluene (248 μL) and Et₃N (19.6 μL, 0.140 mmol) was added to the stirred mixture. After stirring overnight at room temperature, the obtained mixture was concentrated under reduced pressure to give an oily residue, which was purified by column chromatography over silica gel with n-hexane-EtOAc (gradient 3:1 to 2:1 to 1:1) to give compound (203D-092) as a white solid (5.4 mg, 26% yield). Analysis results of LRMS spectrum and reaction scheme are shown below.

LRMS(ESI-QTOF) calcd $C_{84}H_{119}N_3O_{10}$: (M+Na)⁺, 1352.88; found:(M+Na)⁺, 1352.90.

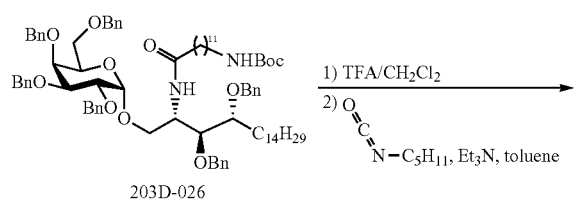

203D-026

203D-092

Synthesis Example 52

Synthesis of N-[(2S,3S,4R)-3,4-dihydroxy-1-{[(2S, 3R,4S,5R,6R)-3,4,5-trihydroxy-6-(hydroxymethyl) tetrahydro-2H-pyran-2-yl]oxy}octadecan-2-yl]-12-(3-pentylureido)dodecanamide (Compound (203D-138))

In the same manner as the synthesis method of compound (1-23) from compound (13-a), amide (203D-092) (3.3 mg, 2.48 μmol) was converted to compound (203D-138) as a white solid (2.0 mg, quant.). Analysis results of LRMS spectrum and reaction scheme are shown below.

LRMS(ESI-QTOF) calcd $C_{42}H_{83}N_3O_{10}$: (M+Na)⁺, 812.60; found: (M+Na)⁺, 812.62.

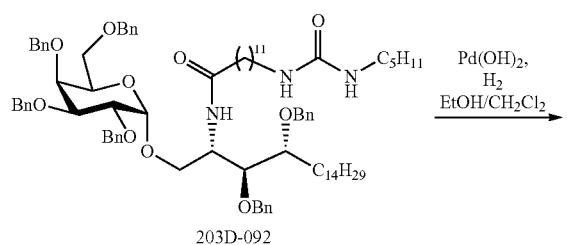

203D-092

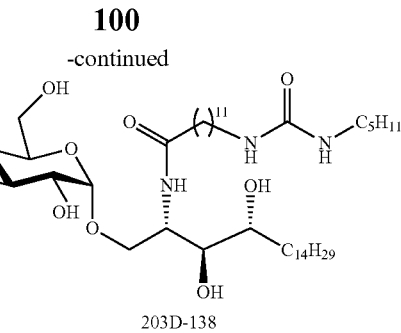

203D-138

Synthesis Example 53

Synthesis of N-[(2S,3S,4R)-3,4-bis(benzyloxy)-1-({(2S,3R,4S,5S,6R)-3,4,5-tris(benzyloxy)-6-[(benzyloxy)methyl]tetrahydro-2H-pyran-2-yl}oxy)octadecan-2-yl]-12-(3-undecylureido)dodecanamide (Compound (203D-044))

In the same manner as the synthesis method of compound (203D-092) from compound (203D-026), compound (203D-026) (20.0 mg, 0.0152 mmol) was converted to compound (203D-044) as a white solid (5.7 mg, 27% yield). Analysis results of LRMS spectrum and reaction scheme are shown below.

LRMS(ESI-QTOF) calcd $C_{90}H_{131}N_3O_{10}$: (M+Na)⁺, 1436.97; found:(M+Na)⁺, 1436.97.

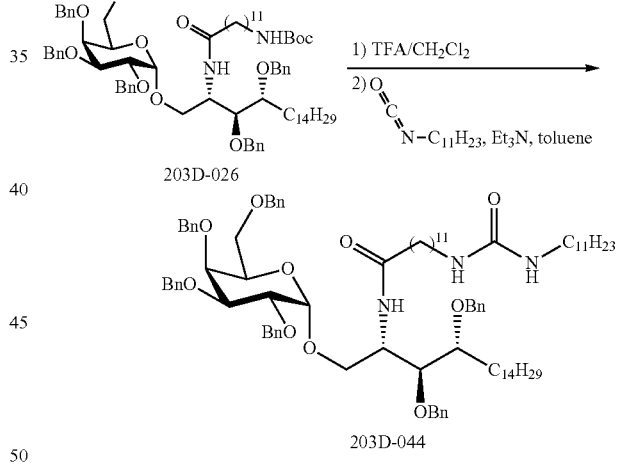

203D-026

203D-044

Synthesis Example 54

Synthesis of N-[(2S,3S,4R)-3,4-dihydroxy-1-{[(2S, 3R,4S,5R,6R)-3,4,5-trihydroxy-6-(hydroxymethyl) tetrahydro-2H-pyran-2-yl]oxy}octadecan-2-yl]-12-(3-undecylureido)dodecanamide (Compound (203D-057))

In the same manner as the synthesis method of compound (1-23) from compound (13-a), compound (203D-044) (5.1 mg, 3.60 μmol) was converted to compound (203D-057) as a white solid (3.2 mg, quant.). Analysis results of LRMS spectrum and reaction scheme are shown below.

LRMS(ESI-QTOF) calcd $C_{45}H_{95}N_3O_{10}$: (M+Na)⁺, 896.69; found: (M+Na)⁺, 896.62.

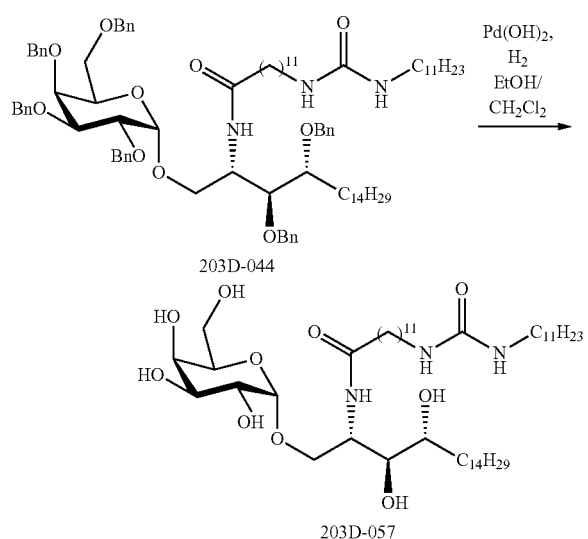

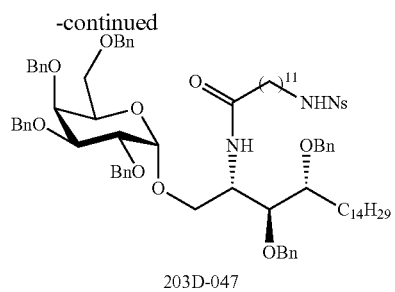

Synthesis Example 55

Synthesis of 4-[(12-{[(2S,3S,4R)-3,4-bis(benzyloxy)-1-({(2S,3R,4S,5S,6R)-3,4,5-tris(benzyloxy)-6-[(benzyloxy)methyl]tetrahydro-2H-pyran-2-yl}oxy)octadecan-2-yl]amino}-12-oxododecyl)amino]-3-nitrobenzenesulfonic acid (Compound (203D-047))

A mixture of compound (203D-026) (20.0 mg, 0.0152 mmol) in TFA/CH$_2$Cl$_2$=1/1 (110 μL) was stirred at room temperature. After stirring for 7.5 hr, the obtained mixture was diluted with CH$_2$Cl$_2$. The obtained diluted product was washed with saturated aqueous NaHCO$_3$, H$_2$O and brine, dried over Na$_2$SO$_4$, and concentrated under reduced pressure to give a crude amine. The obtained amine was dissolved in CH$_2$Cl$_2$ (68.1 μL). DMAP (18.6 mg, 0.152 mmol), pyridine (227 μL) and NsCl (33.7 mg, 0.152 mmol) were added to the stirred mixture. After stirring overnight at room temperature, the obtained mixture was diluted with CH$_2$Cl$_2$. The obtained diluted product was washed with 1M HCl, dried over Na$_2$SO$_4$, and concentrated under reduced pressure to give an oily residue, which was purified by column chromatography over silica gel with n-hexane-EtOAc (3:1) to give compound (203D-047) as a yellow oil (14.9 mg, 70% yield). Analysis results of LRMS spectrum and reaction scheme are shown below.

LRMS(ESI-QTOF) calcd C$_{84}$H$_{111}$N$_3$O$_{13}$S:(M+Na)$^+$, 1424.77; found: (M+Na)$^+$, 1424.75.

Synthesis Example 56

Synthesis of N-[(2S,3S,4R)-3,4-bis(benzyloxy)-1-({(2S,3R,4S,5S,6R)-3,4,5-tris(benzyloxy)-6-[(benzyloxy)methyl]tetrahydro-2H-pyran-2-yl}oxy)octadecan-2-yl]-12-(N-methylheptanamide)dodecanamide (Compound (203D-070))

To a stirred solution of compound (203D-047) (17.8 mg, 0.0127 mmol) in DMF (854 μL) were added MeI (19 μL, 0.305 mmol) and K$_2$CO$_3$ (105 mg, 0.761 mmol). After stirring overnight at room temperature, the obtained mixture was diluted with Et$_2$O. The obtained diluted product was washed with H$_2$O and brine, dried over Na$_2$SO$_4$, and concentrated under reduced pressure to give an oily residue. The obtained residue was dissolved in DMF (635 μL). LiOH.H$_2$O (26.7 mg, 0.635 mmol) and thioglycolic acid (8.7 μL, 0.127 mmol) were added to the stirred mixture. After stirring at room temperature for 6 hr, the obtained mixture was diluted with EtOAc. The obtained diluted product was washed with saturated aqueous NH$_4$Cl, saturated aqueous NaHCO$_3$ and brine, dried over Na$_2$SO$_4$, and concentrated under reduced pressure to give an oily residue. The obtained residue was dissolved in CH$_2$Cl$_2$ (635 μL). Heptanoic acid (27 μL, 0.191 mmol), HOBt (25.7 mg, 0.191 mmol), WSC.HCl (36.5 mg, 0.191 mmol) and DIPEA (39.8 μL, 0.229 mmol) were added to the stirred mixture at 0° C. After stirring overnight at room temperature, the obtained mixture was diluted with CH$_2$Cl$_2$. The obtained diluted product was washed with saturated aqueous NaHCO$_3$, dried over Na$_2$SO$_4$, and concentrated under reduced pressure to give an oily residue, which was purified by column chromatography over silica gel with n-hexane-EtOAc (gradient 4:1 to 3:1) to give compound (203D-070) as a colorless oil (6.8 mg, 40% yield). Analysis results of LRMS spectrum and reaction scheme are shown below.

LRMS(ESI-QTOF) calcd C$_{86}$H$_{122}$N$_2$O$_{10}$: (M+Na)$^+$, 1366.90; found: (M+Na)$^+$, 1366.46.

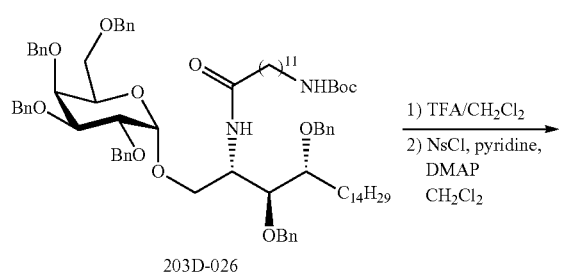

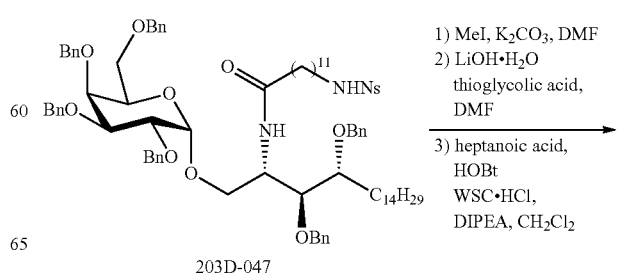

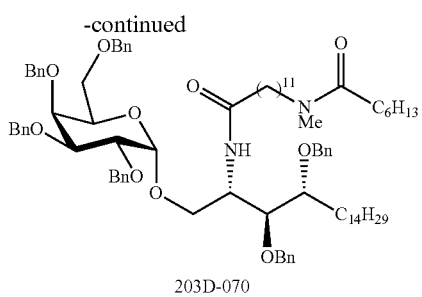

203D-070

Synthesis Example 57

Synthesis of N-[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]-12-(N-methylheptanamide)dodecanamide (Compound (203D-142))

In the same manner as the synthesis method of compound (1-23) from compound (13-a), compound (203D-070) (6.0 mg, 4.46 μmol) was converted to compound (203D-142) as a white solid (3.6 mg, quant.). Analysis results of LRMS spectrum and reaction scheme are shown below.
LRMS(ESI-QTOF) calcd $C_{44}H_{86}N_2O_{10}$: (M+Na)$^+$, 825.62; found: (M+Na)$^+$, 825.63.

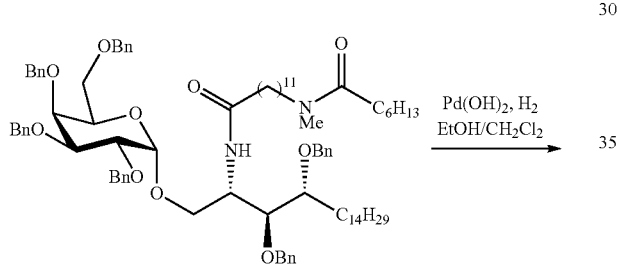

Synthesis Example 58

Synthesis of N-(12-{[(2S,3S,4R)-3,4-bis(benzyloxy)-1-({(2S,3R,4S,5S,6R)-3,4,5-tris(benzyloxy)-6-[(benzyloxy)methyl]tetrahydro-2H-pyran-2-yl}oxy)octadecan-2-yl]amino}-12-oxododecyl)-N-methyltridecanamide (Compound (203D-055))

In the same manner as the synthesis method of compound (203D-070) from compound (203D-047), compound (203D-047) (5.6 mg, 3.96 μmol) was converted to compound (203D-055) as a colorless oil (5.0 mg, 50% yield). Analysis results of LRMS spectrum and reaction scheme are shown below.

LRMS(ESI-QTOF) calcd for $C_{92}H_{134}N_2O_{10}$: (M+Na)$^+$, 1451.00; found: (M+Na)$^+$, 1450.86.

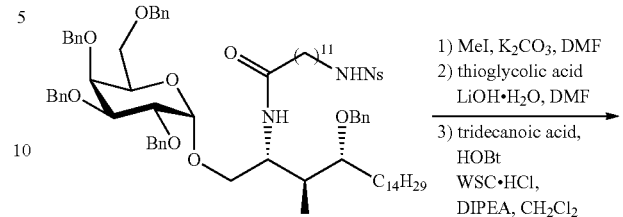

203D-047

1) MeI, $K_2CO_3$, DMF
2) thioglycolic acid
   LiOH·$H_2O$, DMF
3) tridecanoic acid,
   HOBt
   WSC·HCl,
   DIPEA, $CH_2Cl_2$ 203D-055

Synthesis Example 59

Synthesis of N-(12-{[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]amino}-12-oxododecyl)-N-methyltridecanamide (Compound (203D-058))

In the same manner as the synthesis method of compound (1-23) from compound (13-a), compound (203D-055) (2.8 mg, 1.96 μmol) was converted to compound (203D-058) as a white solid (1.7 mg, quant.). Analysis results of LRMS spectrum and reaction scheme are shown below.

LRMS(ESI-QTOF) calcd $C_{50}H_{98}N_2O_{10}$: (M+Na)$^+$, 909.71; found: (M+Na)$^+$, 909.64.

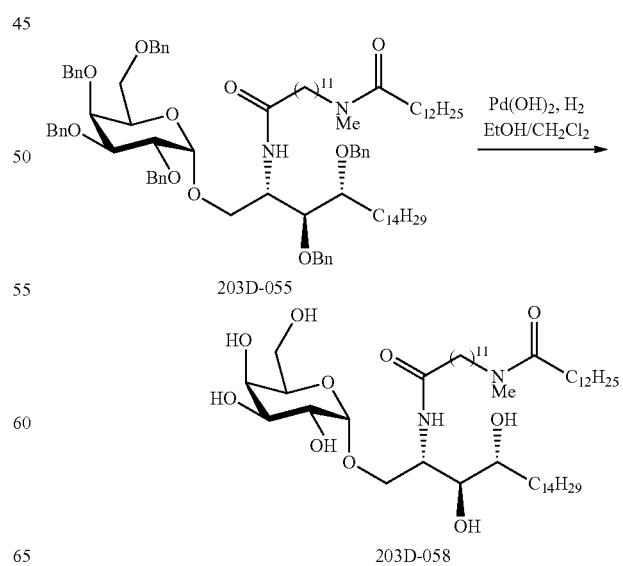

Synthesis Example 60

Synthesis of 4-[(12-{[(2S,3S,4R)-3,4-bis(benzyloxy)-1-({(2S,3R,4S,5S,6R)-3,4,5-tris(benzyloxy)-6-[(benzyloxy)methyl]tetrahydro-2H-pyran-2-yl}oxy)octadecan-2-yl]amino}-12-oxododecyl)(heptyl)amino)]-3-nitrobenzenesulfonic acid (Compound (203D-133))

To a stirred solution of compound (203D-047) (24.3 mg, 0.0173 mmol) in DMF (289 µL) were added 1-iodoheptane (17 µL, 0.104 mmol) and $K_2CO_3$ (35.9 mg, 0.260 mmol). After stirring overnight at room temperature, the mixture was diluted with $Et_2O$. The obtained diluted product was washed with $H_2O$ and brine, dried over $Na_2SO_4$, and concentrated under reduced pressure to give an oily residue, which was purified by column chromatography over silica gel with n-hexane-EtOAc (3:1) to give compound (203D-133) as a yellow oil (24.4 mg, 94% yield). Analysis results of LRMS spectrum and reaction scheme are shown below. LRMS(ESI-QTOF) calcd $C_{91}H_{125}N_3O_{13}S$, $(M+Na)^+$, 1523.89; found: $(M+Na)^+$, 1523.92.

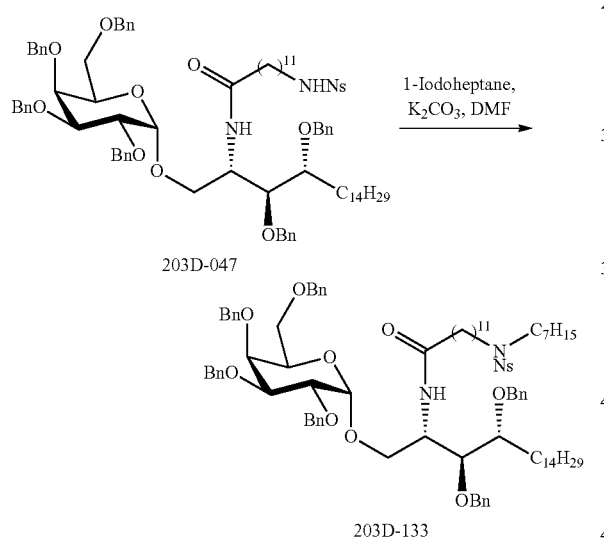

Synthesis Example 61

Synthesis of N-[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]-12-(heptylamino)dodecanamide (Compound (203D-151))

To a stirred solution of compound (203D-133) (6.9 mg, 4.59 µmol) in DMF (229 µL) were added $LiOH \cdot H_2O$ (9.6 mg, 0.230 mmol) and thioglycolic acid (3.1 µL, 0.0458 mmol). After stirring at room temperature for 6 hr, the mixture was diluted with n-hexane-EtOAc (1:10). The obtained diluted product was washed with saturated aqueous $NH_4Cl$, saturated aqueous $NaHCO_3$ and brine, dried over $Na_2SO_4$, and concentrated under reduced pressure to give an oily residue. In the same manner as the synthesis method of compound (1-23) from compound (13-a), the obtained residue was converted to compound (203D-151) as a white solid (3.6 mg, quant.). Analysis results of LRMS spectrum and reaction scheme are shown below.

LRMS(ESI-QTOF) calcd $C_{43}H_{86}N_2O_9$:$(M+H)^+$, 775.64; found: $(M+Na)^+$, 775.66.

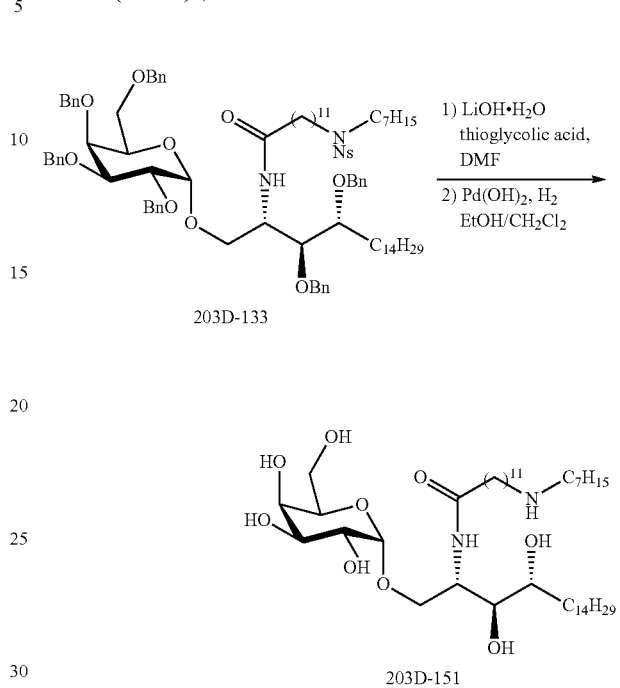

Synthesis Example 62

Synthesis of 4-[(12-{[(2S,3S,4R)-3,4-bis(benzyloxy)-1-({(2S,3R,4S,5S,6R)-3,4,5-tris(benzyloxy)-6-[(benzyloxy)methyl]tetrahydro-2H-pyran-2-yl}oxy)octadecan-2-yl]amino}-12-oxododecyl)(tridecyl)amino]-3-nitrobenzenesulfonic acid (Compound (203D-097))

In the same manner as the synthesis method of compound (203D-133) from compound (203D-047), compound (203D-047) (20.5 mg, 0.0146 mmol) was converted to compound (203D-097) as a yellow oil (17.9 mg, 77% yield). Analysis results of LRMS spectrum and reaction scheme are shown below.

LRMS(ESI-QTOF) calcd $C_{97}H_{137}N_3O_{13}S$: $(M+Na)^+$, 1607.98; found: $(M+Na)^+$, 1608.01.

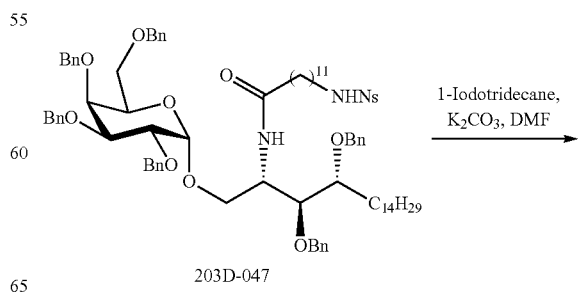

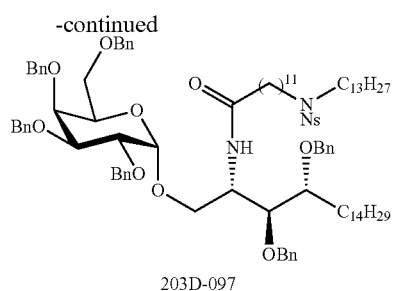

Synthesis Example 63

Synthesis of N-[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]-12-(tridecylamino)dodecanamide (Compound (203D-145))

In the same manner as the synthesis method of compound (203D-151) from compound (203D-133), compound (203D-097) (14.9 mg, 9.37 µmol) was converted to compound (203D-145) as a yellow oil (8.1 mg, quant.). Analysis results of LRMS spectrum and reaction scheme are shown below. LRMS(ESI-QTOF) calcd $C_{49}H_{98}N_2O_9$:(M+H)$^+$, 859.73; found: (M+Na)$^+$, 859.74.

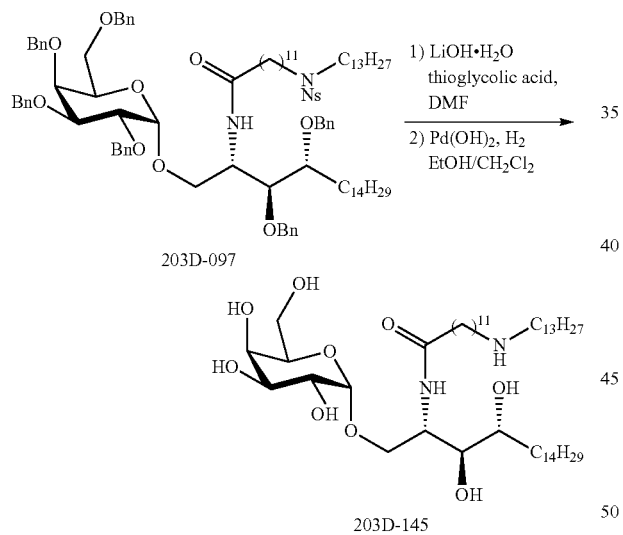

Synthesis Example 64

Synthesis of N-[(2S,3S,4R)-3,4-bis(benzyloxy)-1-({(2S,3R,4S,5S,6R)-3,4,5-tris(benzyloxy)-6-[(benzyloxy)methyl]tetrahydro-2H-pyran-2-yl}oxy)octadecan-2-yl]-14-oxoicosanamide (Compound (203D-127))

To a stirred solution of compound (203D-012) (15.9 mg, 0.0152 mmol) in benzene (760 µL) and H$_2$O (30.4 µL) was added PPh$_3$ (9.96 mg, 0.0380 mmol). After stirring overnight at 50° C., the obtained mixture was concentrated under reduced pressure, and azeotroped three times with toluene to give a crude residue. The obtained residue was dissolved in CH$_2$Cl$_2$ (304 µL). A carboxylic acid (29.8 mg, 0.0912 mmol), HOBt (12.3 mg, 0.0912 mmol), WSC·HCl (17.5 mg, 0.0912 mmol) and DIPEA (19.1 µL, 0.109 mmol) were added to the stirred mixture at 0° C. After stirring overnight at room temperature, the obtained mixture was diluted with CH$_2$Cl$_2$. The obtained diluted product was washed with saturated aqueous NaHCO$_3$, H$_2$O and brine, dried over Na$_2$SO$_4$, and concentrated under reduced pressure to give an oily residue, which was purified by column chromatography over silica gel with n-hexane-EtOAc (5:1) to give compound (203D-127) as a colorless oil (2.8 mg, 14% yield). Analysis results of LRMS spectrum and reaction scheme are shown below.

LRMS(ESI-QTOF) calcd $C_{86}H_{121}NO_{10}$: (M+Na)$^+$, 1350.89; found:(M+Na)$^+$, 1350.92.

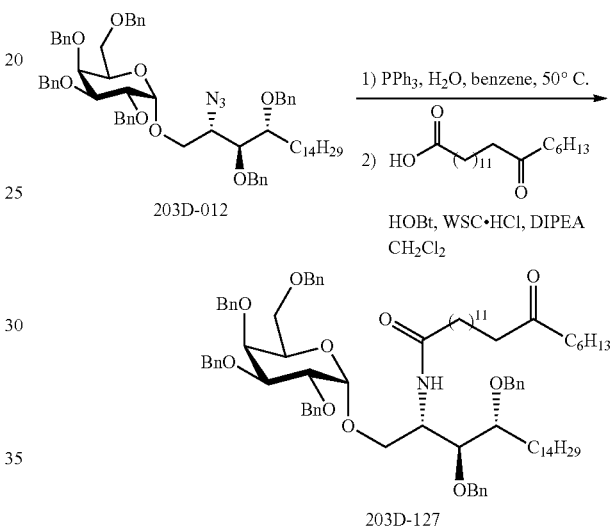

Synthesis Example 65

Synthesis of N-[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]-14-oxoicosanamide (Compound (203D-152))

In the same manner as the synthesis method of compound (1-23) from compound (13-a), compound (203D-127) (2.4 mg, 1.81 µmol) was converted to compound (203D-152) as a white solid (1.4 mg, quant.). Analysis results of LRMS spectrum and reaction scheme are shown below.

LRMS(ESI-QTOF) calcd $C_{44}H_{85}NO_{10}$:(M+Na)$^+$, 810.61; found: (M+Na)$^+$, 810.63.

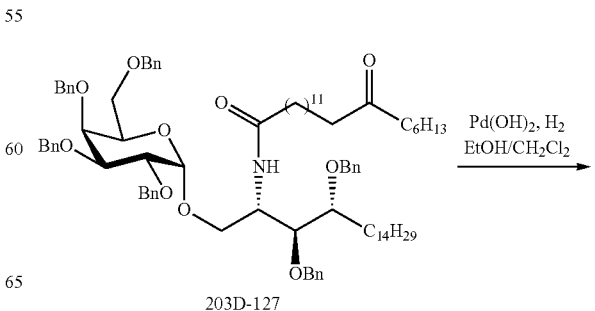

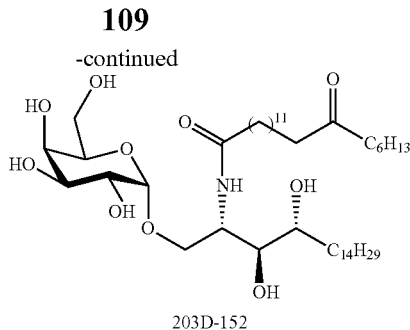

Synthesis Example 66

Synthesis of N-[(2S,3S,4R)-3,4-bis(benzyloxy)-1-({(2S,3R,4S,5S,6R)-3,4,5-tris(benzyloxy)-6-[(benzyloxy)methyl]tetrahydro-2H-pyran-2-yl}oxy)octadecan-2-yl]-14-oxohexacosanamide (Compound (203D-150))

In the same manner as the synthesis method of compound (203D-127) from compound (203D-012), compound (203D-012) (25.2 mg, 0.0241 mmol) was converted to compound (203D-150) as a colorless oil (17.4 mg, 51% yield). Analysis results of LRMS spectrum and reaction scheme are shown below.

LRMS(ESI-QTOF) calcd $C_{92}H_{133}NO_{10}$:(M+Na)$^+$, 1435.99; found: (M+Na)$^+$, 1436.01.

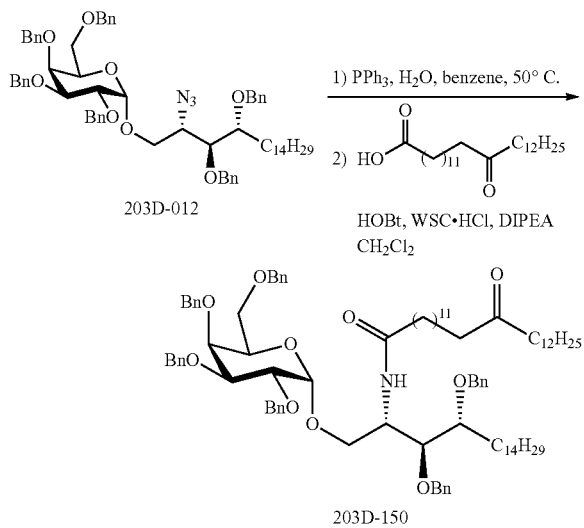

Synthesis Example 67

Synthesis of N-[(2S,3S,4R)-3,4-dihydroxy-1-{[(2S,3R,4S,5R,6R)-3,4,5-trihydroxy-6-(hydroxymethyl)tetrahydro-2H-pyran-2-yl]oxy}octadecan-2-yl]-14-oxohexacosanamide (Compound (203D-153))

In the same manner as the synthesis method of compound (1-23) from compound (13-a), compound (203D-150) (9.1 mg, 6.44 μmol) was converted to compound (203D-153) as a white solid (3.2 mg, 57% yield). Analysis results of LRMS spectrum and reaction scheme are shown below.

LRMS(ESI-QTOF) calcd $C_{50}H_{97}NO_{10}$: (M+Na)$^+$, 894.70; found: (M+Na)$^+$, 894.72.

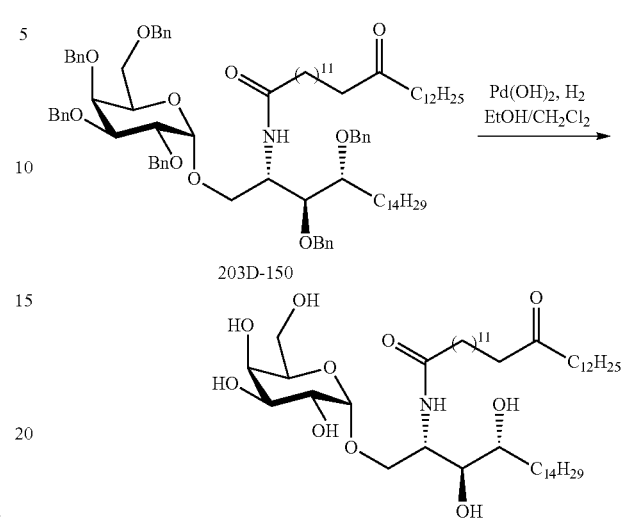

Evaluation

Using the respective compounds obtained and a control compound, the respective compounds were evaluated for their capacity to induce a cytokine (IL-2, IL-4, or IFN-γ) from a cell according to the following procedure.

Experiment 1: Experiment Using a Hybridoma

[Cell Culture]

RBL-CD1d cells which are cells forcibly expressing mouse CD1d, and NKT hybridoma 2E10 cells were cultured in RPMI-1640 (manufactured by Nacalai Tesque, Inc.) supplemented with 10% fetal bovine serum (FBS, manufactured by Biowest) and 1% penicillin-streptomycin (manufactured by Gibco). See Sagiv, Y.; Bai, L.; Wei, D. G.; Agami, R.; Savage, P. B.; Teyton, L.; Bendelac, A. J. Exp. Med. 2007, 204, 921-928 for details of RBL-CD1d cells. See Nyambayar, D.; Iwabuchi, K.; Shirai, K.; Iwabuchi, C.; Hedlund, E.; Kon, Y. Yanagawa, Y.; Onoe, K. J. Clin. Exp. Hematop. 2007, 47, 1-8 for details of NKT hybridoma 2E10 cells.

[Hybridoma Stimulation Assay]

Figure 2:
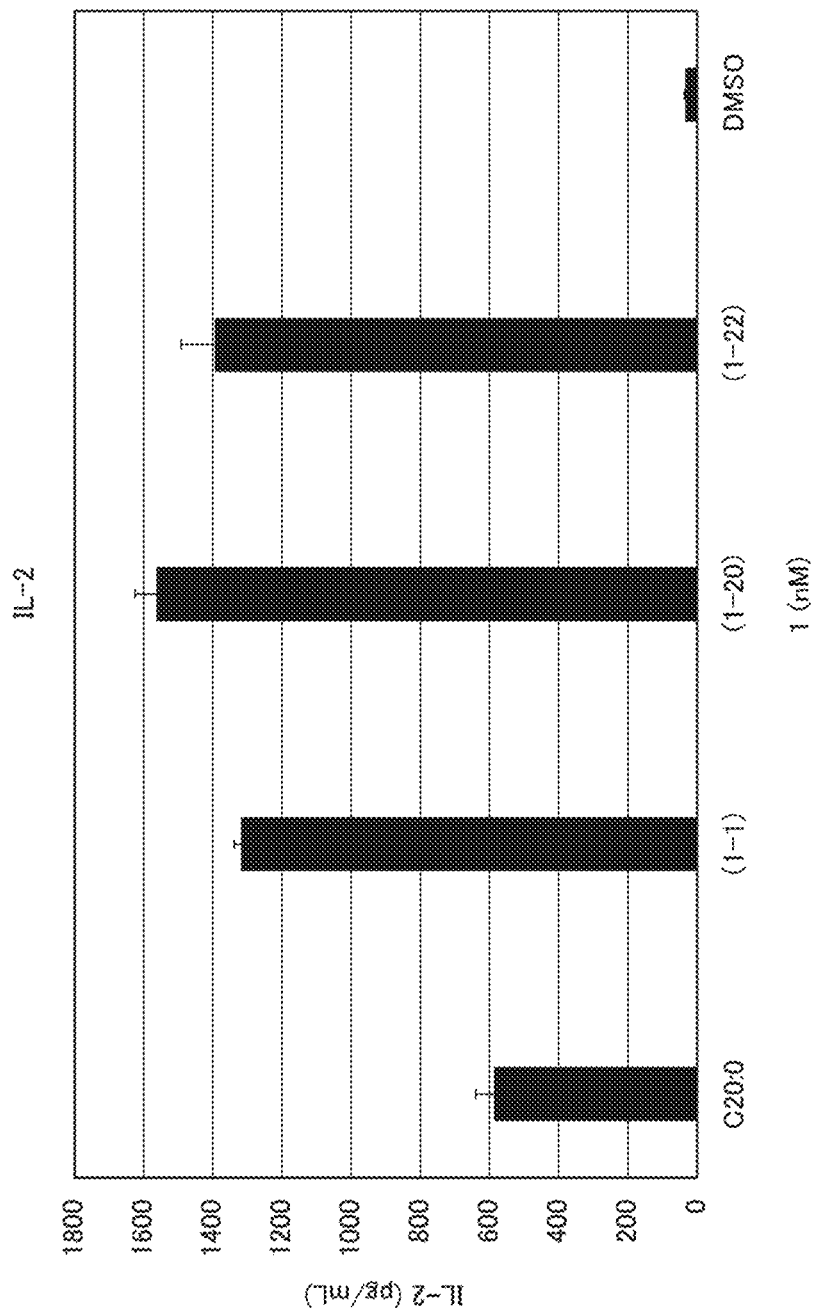
FIG. 2 is a graph illustrating the amount of IL-2 production in the experiment using hybridoma for the Example compounds and a control compound.
Figure 3:
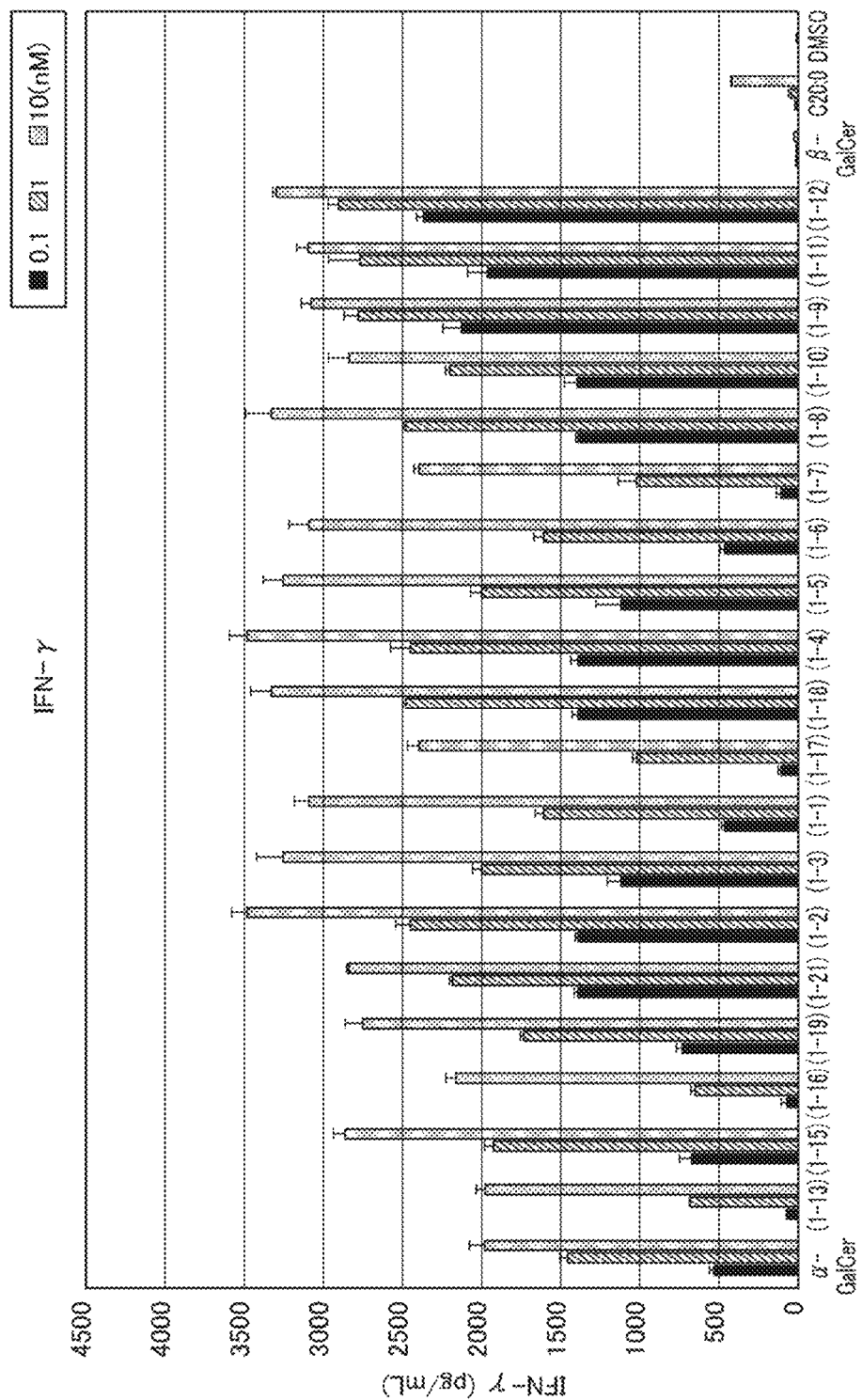
FIG. 3 is a graph illustrating the amount of IFN-γ production in the experiment using hybridoma for the Example compounds and a control compound.
Figure 5:
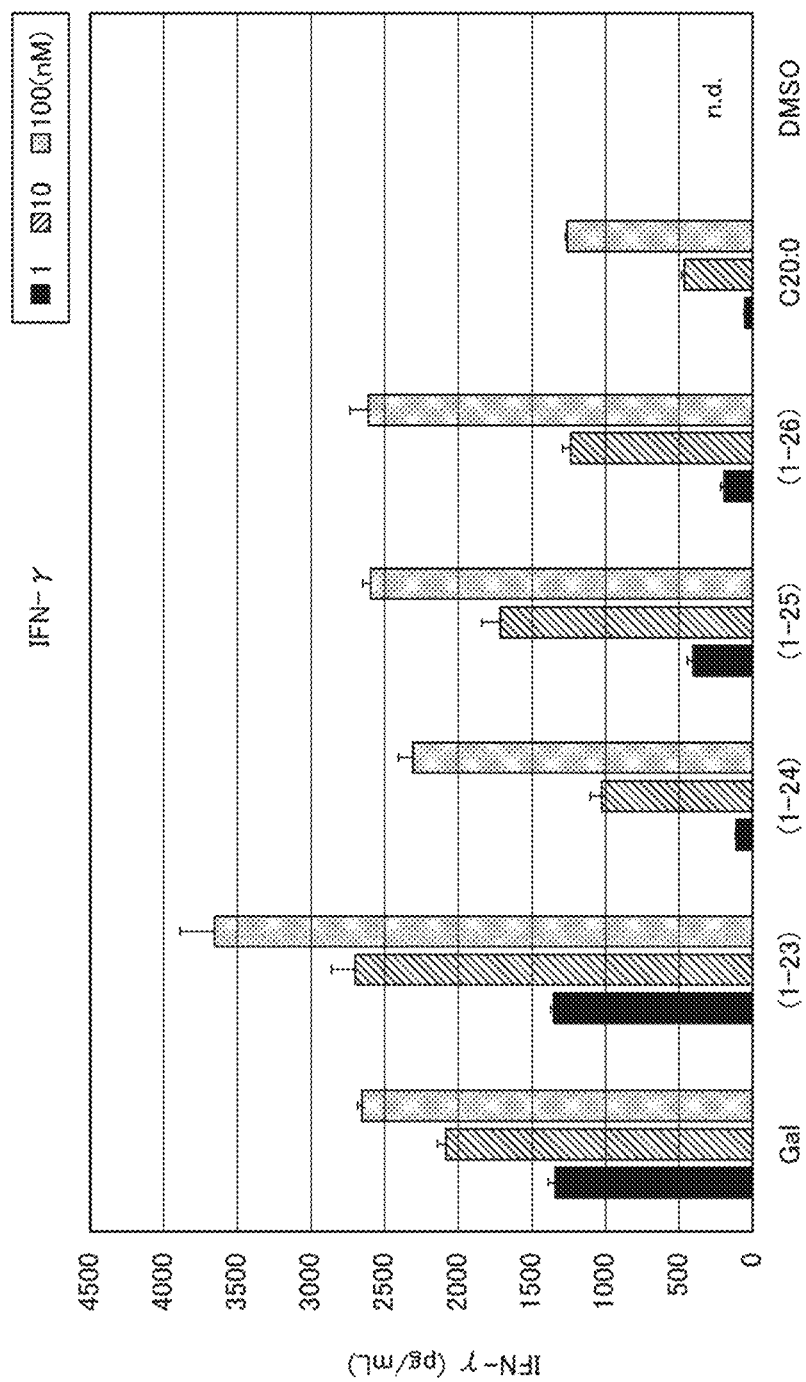
FIG. 5 is a graph illustrating the amount of IFN-γ production in the experiment using hybridoma for the Example compounds and a control compound.
Figure 6:
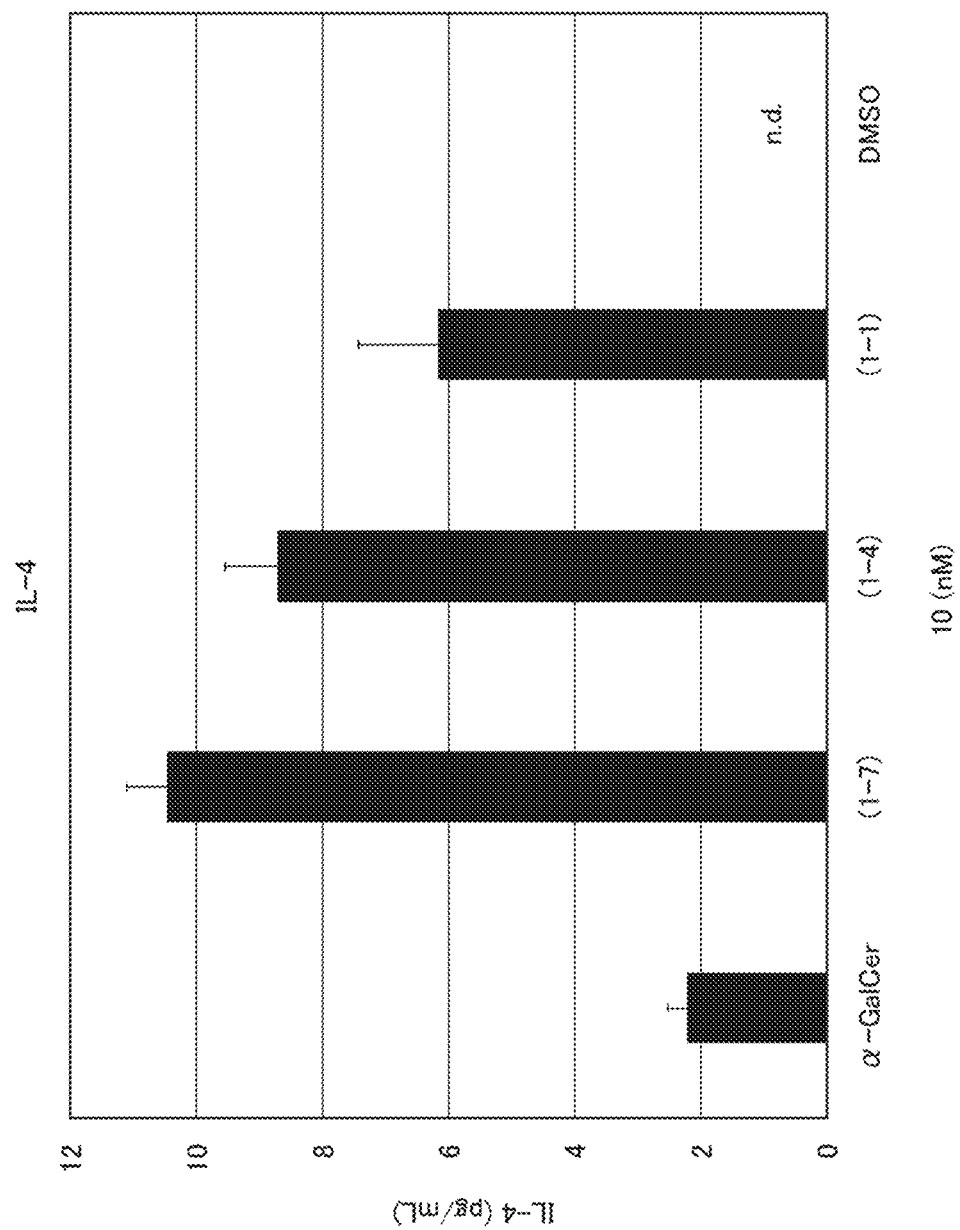
FIG. 6 is a graph illustrating the amount of IL-4 production in the experiment using hybridoma for the Example compounds and a control compound.

RBL-CD1d (adjusted to $1.8 \times 10^4$ cells per 96-well microplate) and NKT hybridoma 2E10 cells (adjusted to $1.8 \times 10^4$ cells per 96-well microplate) were cocultured for 48 hr in the presence of each compound at various concentrations (1, 10 or 100 nM for IL-2 and IFN-γ measurement, and 0.1, 1, 10 or 100 nM for IL-4 measurement). The culture supernatant was collected and the amount of IL-2, IL-4 and IFN-γ released from cells was measured by ELISA (a kit manufactured by Affymetrix was used). The results are shown in FIGS. 1 to 2 for IL-2, FIGS. 3 to 5 for IFN-γ, and FIG. 6 for IL-4.

The details of the compounds shown in FIGS. 1 to 6 are as follows.

DMSO: dimethyl sulfoxide

Each compound with a number in parentheses ((1-13), (1-15) or the like): the compound of the present invention β-GalCer: GalCer in which a sugar at position-1 is beta-bonded, and the structure excluding the binding site has the same structure as α-GalCer.

α-GalCer (20:0): a compound in which the carbon number of the acyl group in α-GalCer is shortened from 26 to 20 (the structure of the compound is shown below).

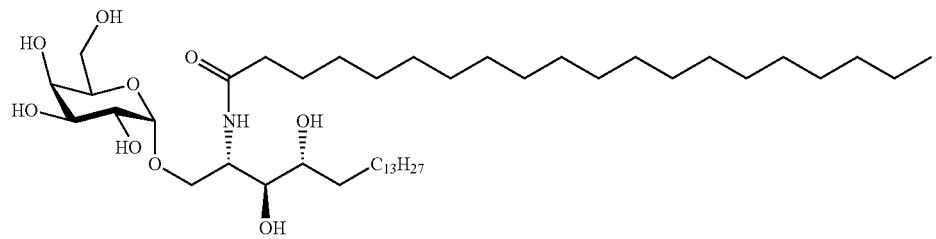

As understood from FIGS. 1 to 5, the compounds of the present invention exhibited higher cytokine-inducing capacity than β-GalCer and C19. Furthermore, even compared with α-GalCer, which had been previously known to have cytokine-inducing capacity higher than β-GalCer and C19, the compounds of the present invention exhibited cytokine-inducing capacity equivalent to or higher than that of α-GalCer. A similar tendency can be also understood from FIG. 6.

Experiment 2: Experiment Using Splenocytes

An experiment similar to Experiment 1 was carried out by using mouse splenocytes instead of RBL-CD1d cells and NKT hybridoma 2E10 cells. In the experiment using splenocytes, the effect of each compound can be evaluated under a condition containing cells other than NKT cells, so that the effect of each compound under a condition closer to the living body can be elucidated.

Figure 4:
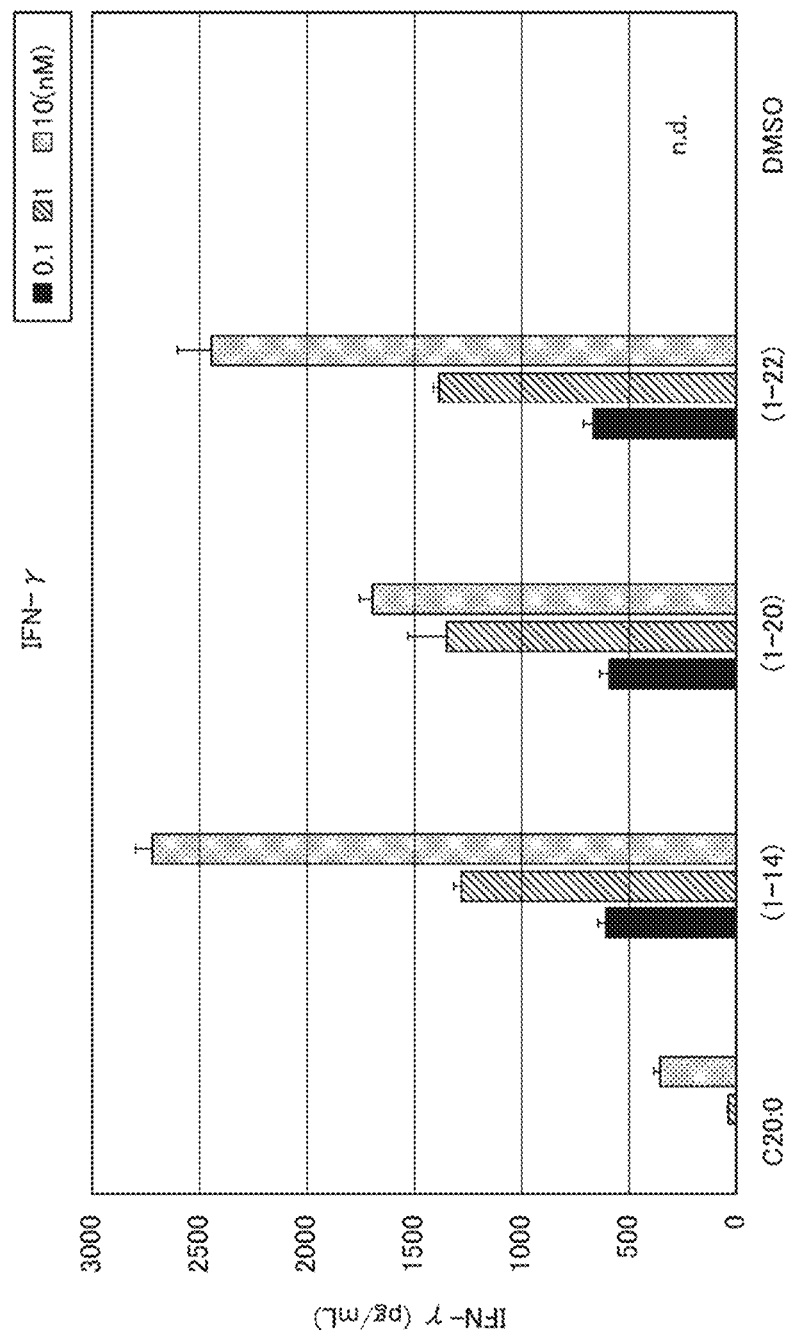
FIG. 4 is a graph illustrating the amount of IFN-γ production in the experiment using hybridoma for the Example compounds and a control compound.

First, seven-week-old female C57BL/6 NCrSlc mice were acclimated for 8 days, then euthanized by cervical dislocation, and the spleen was separated. Splenocytes were prepared from the spleen and seeded at $3 \times 10^5$ cells/well in a 96-well plate. Each of the compound of the present invention and the control compound (α-GalCer) was added at three concentrations in triplicate and culturing was conducted for 48 hours at 37° C. in a 5% $CO_2$ incubator. The culture supernatant after the culturing was harvested and measured for IFN-γ and IL-4 using an ELISA kit. The results are shown in FIG. 4 for IFN-γ and FIG. 5 for IL-4.

Figure 7:
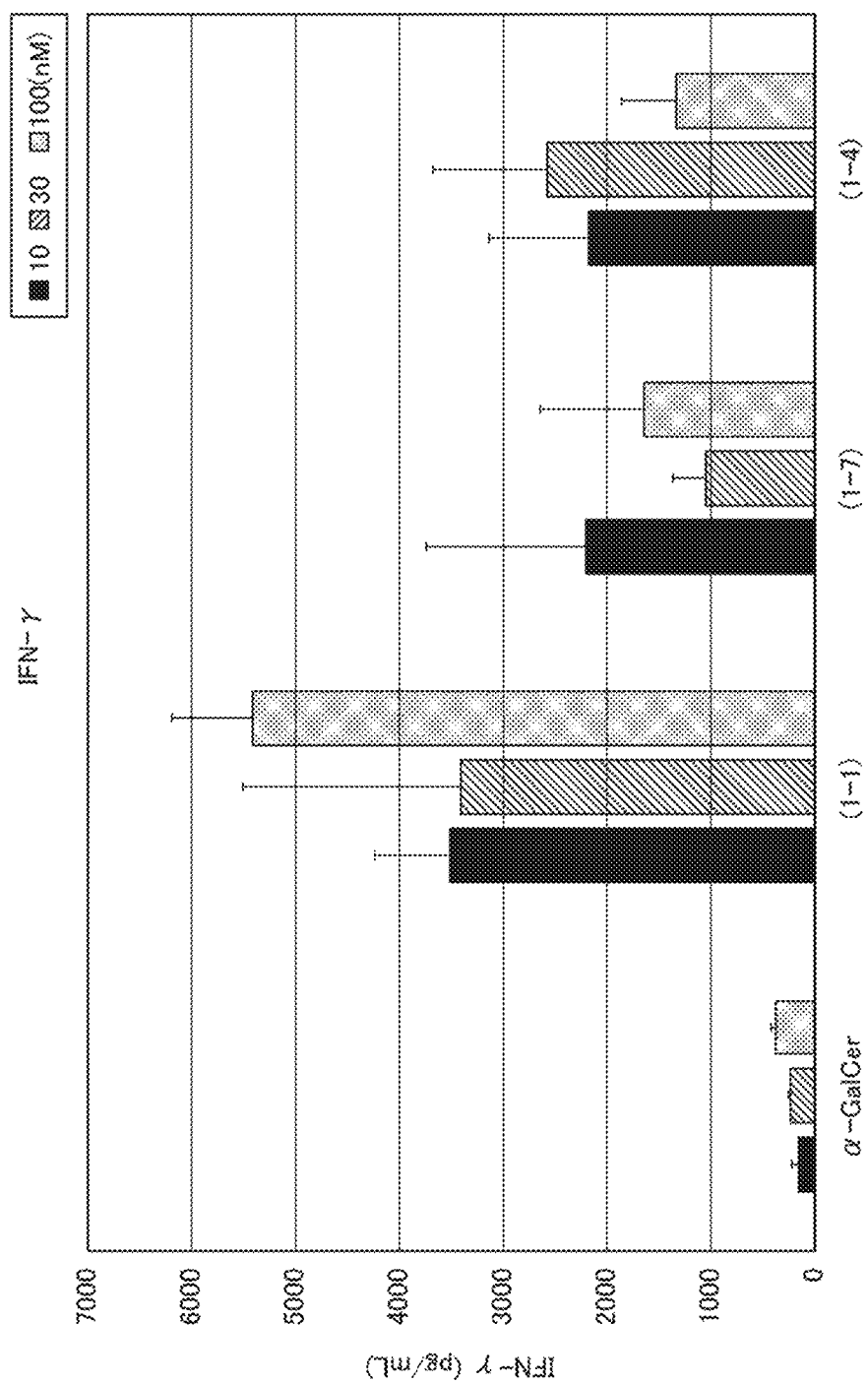
FIG. 7 is a graph illustrating the amount of IFN-γ production in the experiment using mouse splenocytes for the Example compounds and a control compound.
Figure 8:
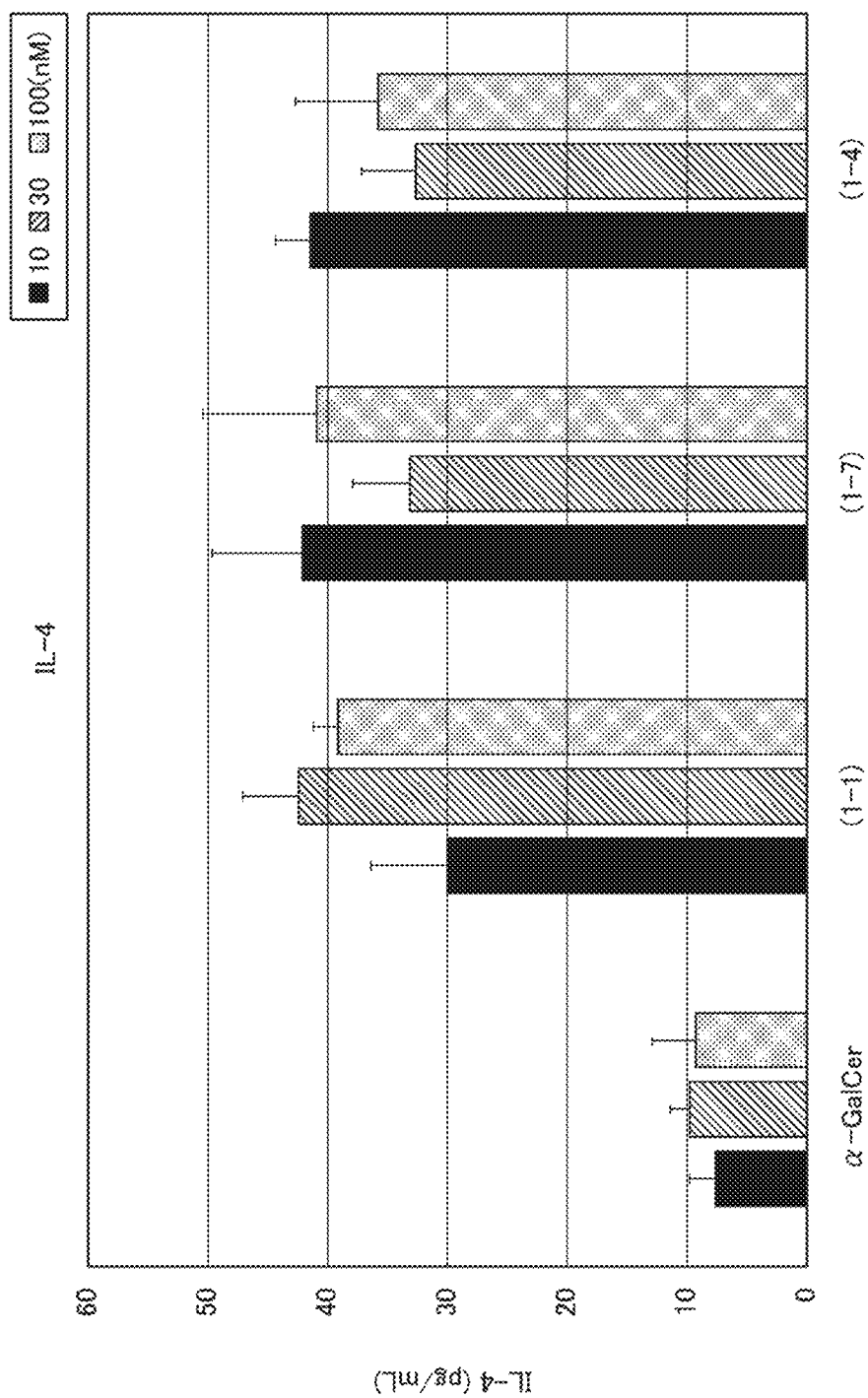
FIG. 8 is a graph illustrating the amount of IL-4 production in the experiment using mouse splenocytes for the Example compounds and a control compound.

The details of the compounds shown in FIGS. 7 and 8 follow those of FIGS. 1 to 6.

As understood from FIGS. 7 and 8, the compounds of the present invention exhibited cytokine-inducing capacity equivalent to or higher than α-GalCer, which had been previously known to have high cytokine-inducing capacity.

Experiment 3: Cell-Free Assay

Solution of mouse CD1d:IgG fusion protein (manufactured by BD Bioscience) in PBS (0.25 μg/well) was added to a 96 well plate and left standing at 37° C. for 24 hr. After washing with PBS, a solution of each compound of the present invention and the control compound (α-GalCer) in PBS (1% DMSO, 0.005% Triton X-100) were added at three concentrations in triplicate, and left standing at 37° C. for 24 hr. After washing with PBS, 2E10 NKT hybridoma cells ($2.5 \times 10^5$ cells/well) were plated in each well, and cultured for at 37° C., for 48 hr in a $CO_2$ incubator. Culture supernatant after the culter was harvested and measured for IL-2 by an ELISA kit. The results are shown in FIGS. 9 to 11.

Figure 9:
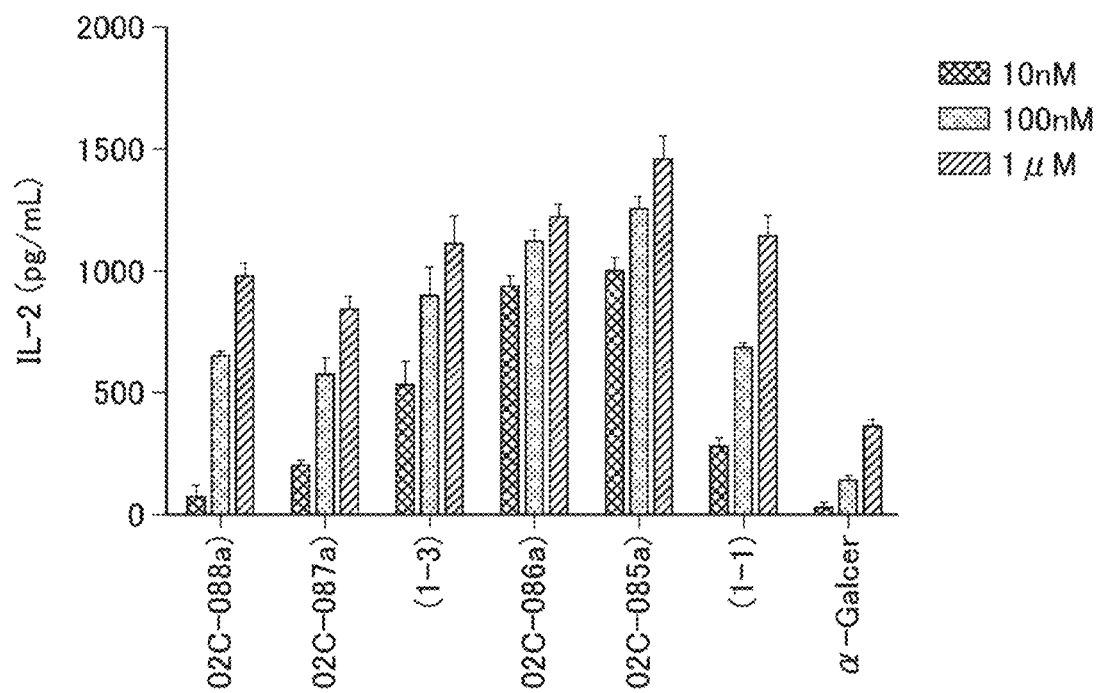
FIG. 9 is a graph illustrating the amount of IL-2 production in the cell-free assay for the Example compounds and a control compound.
Figure 10:
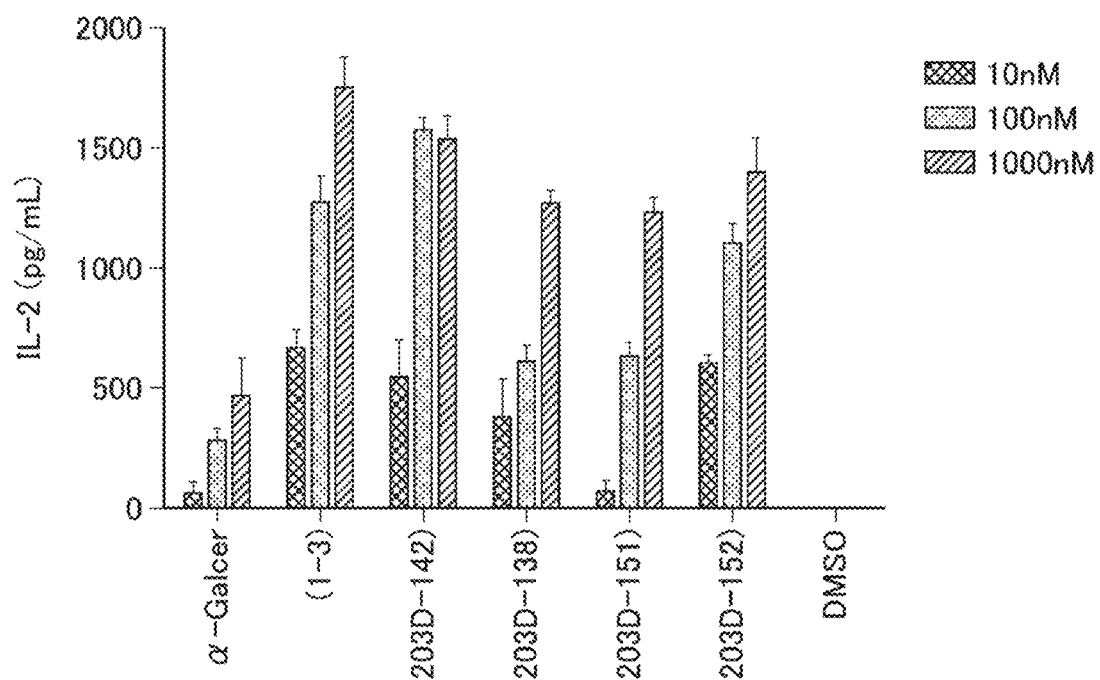
FIG. 10 is a graph illustrating the amount of IL-2 production in the cell-free assay for the Example compounds and a control compound.
Figure 11:
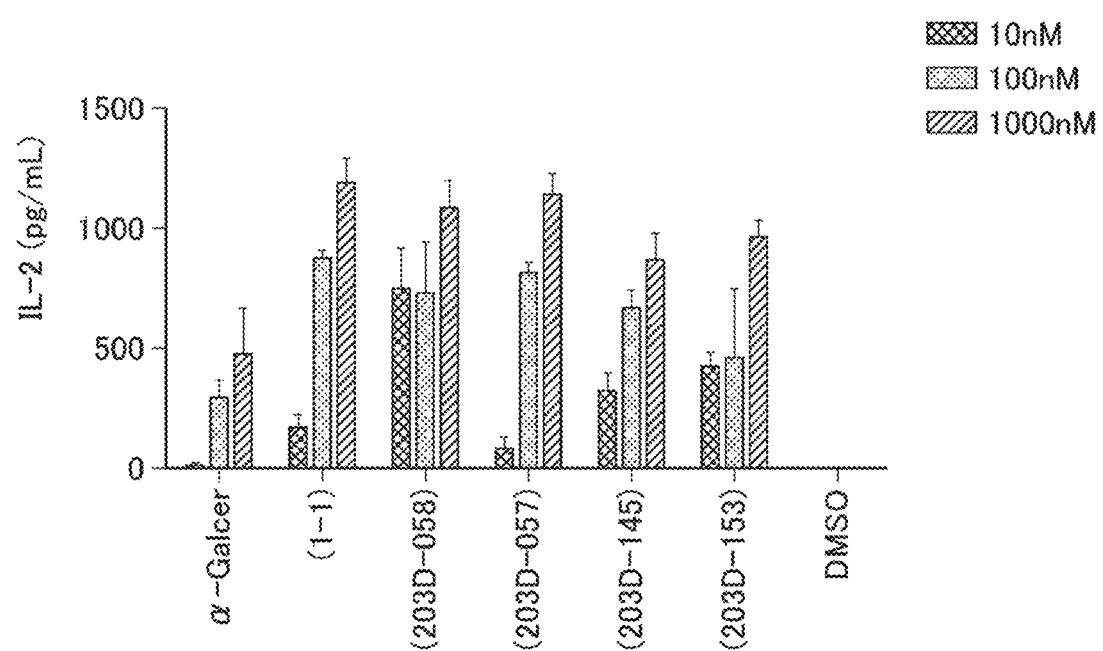
FIG. 11 is a graph illustrating the amount of IL-2 production in the cell-free assay for the Example compounds and a control compound.

The details of the compounds shown in FIGS. 9 to 11 follow those of FIGS. 1 to 6.

As understood from FIGS. 9 to 11, the compounds of the present invention exhibited cytokine-inducing capacity equivalent to or higher than α-GalCer, which had been previously known to have high cytokine-inducing capacity.

The invention claimed is:

1. A compound represented by formula (1):

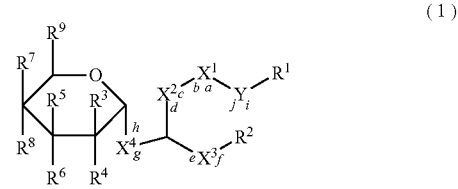

(1)

or a salt thereof,
wherein
Y is a group represented by any of formulae (A) to (E)

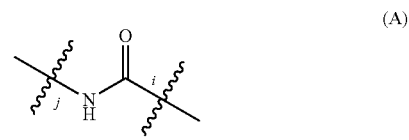

(A)

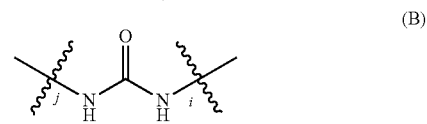

(B)

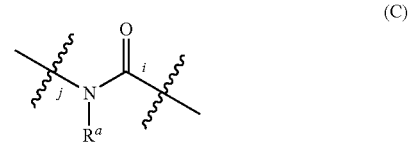

(C)

(D)

(E)

R¹ is a $C_{2-45}$ monovalent aliphatic group or a $C_{2-45}$ monovalent aryl group, each of which is optionally substituted with a halogen atom, an optionally substituted alkoxy group, a group derived from a heterocycle, or a group represented by formula (XIII)

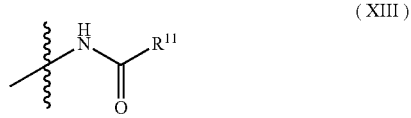
(XIII)

R¹¹ is an alkyl group or an alkenyl group,
R² is a monovalent hydrocarbon group optionally having a substituent,
$R^a$ is a monovalent hydrocarbon group having a carbon number of 1 to 5,
X¹ is a divalent hydrocarbon group,
X² is —NHCO—, —NMeCO—, —O—, or —OCO—, wherein Me represents a methyl group,
X³ is —CH₂—, —CHOH—, or —CHNH₂—,
X⁴ is —OCH₂—, —CH₂—CH₂—, —CH=CH—, —SCH₂—, or —NHCH₂—, and
either
(A) R³, R⁶, and R⁸ are hydrogen atoms,
R⁴ is hydrogen atom, hydroxy group, —NH₂ or —NHCOCH₃,
R⁵ is hydroxy group, an alkoxy group, an arylalkoxy group, or —OSO₃Na,
R⁷ is hydroxy group, an alkoxy group, an arylalkoxy group, or —OSO₃Na, and
R⁹ is hydrogen atom, hydroxymethyl group, methyl group, an alkoxymethyl group, an arylalkoxymethyl group, —CH₂SO₃Na, a group represented by formula (VII), or a group represented by formula (VIII),

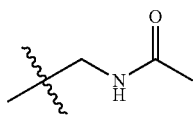
(VII)

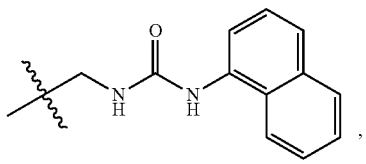
(VIII), or
(B) R³, R⁶, and R⁷ are hydrogen atoms,
R⁴ is hydrogen atom, hydroxy group, —NH₂ or —NHCOCH₃,
R⁵ is hydroxy group, an alkoxy group, an arylalkoxy group, or —OSO₃Na,
R⁸ is hydroxy group, an alkoxy group, an arylalkoxy group, or —OSO₃Na, and
R⁹ is hydrogen atom, hydroxymethyl group, methyl group, an alkoxymethyl group, an arylalkoxymethyl group, —CH₂OSO₃Na, a group represented by formula (VII), or a group represented by formula (VIII).

2. The compound or a salt thereof according to claim 1, wherein a total carbon number of carbon(s) in the monovalent hydrocarbon group excluding a substituent in R¹ and carbon(s) in the divalent hydrocarbon group in X¹ is 5 to 50.

3. The compound or a salt thereof according to claim 2, wherein the monovalent hydrocarbon group in R¹ comprises a linear carbon chain having a primary carbon atom, and the primary carbon atom is substituted.

4. The compound or a salt thereof according to claim 1, wherein the monovalent hydrocarbon group in R¹ comprises a linear carbon chain having a primary carbon atom, and the primary carbon atom is substituted.

5. The compound or a salt thereof according to claim 1, wherein R¹ is (a) a $C_{2-45}$ monovalent aliphatic group substituted with a halogen atom, an epoxy group, or a group represented by formula (XIII)

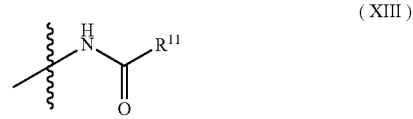
(XIII)

wherein R¹¹ is an alkyl group or an alkenyl group, or (b) a $C_{2-45}$ monovalent aryl group substituted with a halogen atom or an alkoxy group.

6. The compound or a salt thereof according to claim 1, wherein R¹ is a $C_{2-45}$ monovalent aliphatic group optionally substituted with a halogen atom, an epoxy group, or a group represented by formula (XIII)

(XIII)

wherein R¹¹ is an alkyl group or an alkenyl group.

7. The compound or a salt thereof according to claim 1, wherein R¹ is a $C_{2-45}$ monovalent aryl group optionally substituted with a halogen atom or an alkoxy group.

8. The compound or a salt thereof according to claim 1, wherein
R² is a group represented by formula (XIV)

(XIV)

X⁵ is —CR¹³R¹⁴—,
R¹³ and R¹⁴ are independently hydrogen atom or hydroxy group,
R¹² is an alkyl group optionally having a substituent,
X¹ is an alkylene group,
X² is —NHCO—,
X³ is —CHOH—,
X⁴ is —OCH₂—,
R³, R⁶, and R⁸ are hydrogen atoms,
R⁴ is hydroxy group,
R⁵ is hydroxy group,
R⁷ is hydroxy group, and
R⁹ is hydroxymethyl group.

9. The compound or a salt thereof according to claim 1, wherein the compound is represented by formula (1-c):
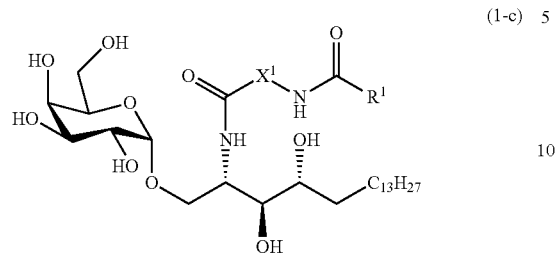
or a salt thereof, where R and $X^1$ are as defined in claim 1.
10. The compound or a salt thereof according to claim 1, wherein the compound is represented by formula
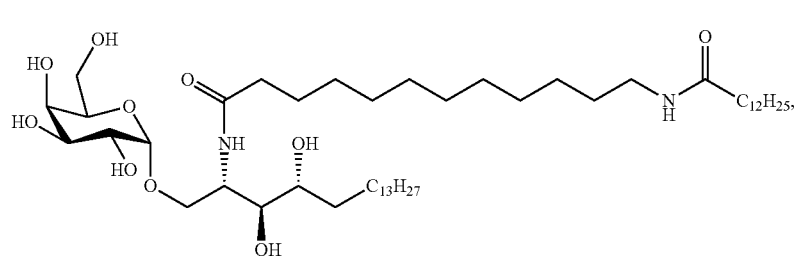
(A)
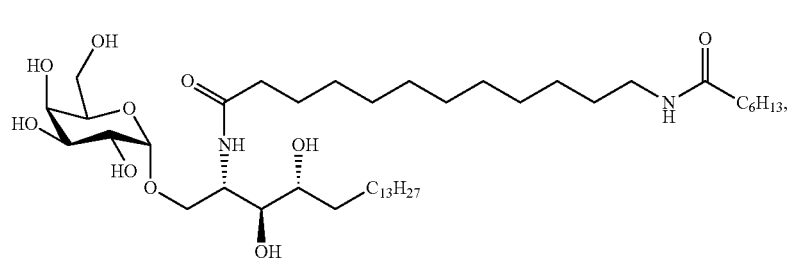
(B)
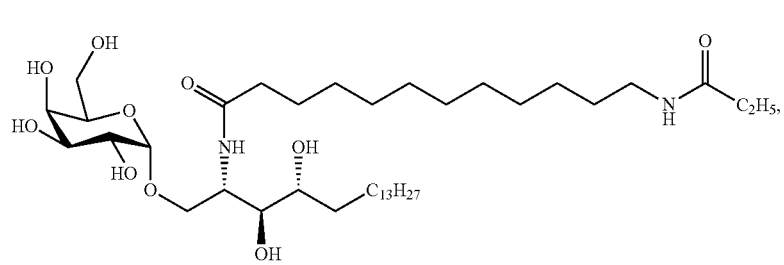
(C)
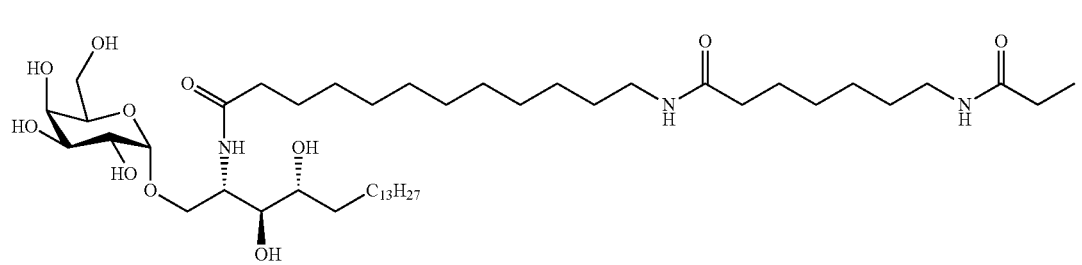
(D)

-continued (E), (F), (G), (H), (I), (J) [chemical structures]

or a salt thereof, wherein Ph represents a phenyl group and Me represents a methyl group.

11. The compound or a salt thereof according to claim 1, wherein the compound is represented by formula (C):

(C) [chemical structure]

or a salt thereof.

12. The compound or a salt thereof according to claim 1, wherein the compound is represented by formula (F):

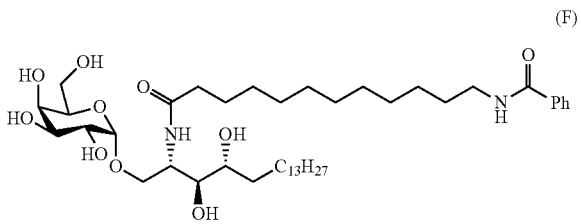

or a salt thereof.

13. A pharmaceutical composition which contains a compound according to claim 1 or a pharmacologically acceptable salt thereof.

14. A pharmaceutical composition comprising a compound according to claim 10 or a pharmacologically acceptable salt thereof.

15. A pharmaceutical composition comprising a compound according to claim 11 or a pharmacologically acceptable salt thereof.

16. A pharmaceutical composition comprising a compound according to claim 12 or a pharmacologically acceptable salt thereof.

17. A method of activating a natural killer T cell, which comprises contacting a natural killer T cell with a compound or a salt thereof according to claim 1.

18. A method of activating a natural killer T cell, which comprises contacting a natural killer T cell with a compound or a salt thereof according to claim 10.

19. A method of activating a natural killer T cell, which comprises contacting a natural killer T cell with a compound or a salt thereof according to claim 11.

20. A method of activating a natural killer T cell, which comprises contacting a natural killer T cell with a compound or a salt thereof according to claim 12.

* * * * *